US006177404B1

(12) United States Patent
DeFeo-Jones et al.

(10) Patent No.: US 6,177,404 B1
(45) Date of Patent: Jan. 23, 2001

(54) CONJUGATES USEFUL IN THE TREATMENT OF BENIGN PROSTATIC HYPERPLASIA

(75) Inventors: Deborah DeFeo-Jones; Raymond E. Jones, both of Lansdale; Allen I. Oliff, Gwynedd Valley; Edward M. Scolnick, Wynnewood; Victor M. Garsky, Blue Bell, all of PA (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/051,759
(22) PCT Filed: Oct. 15, 1996
(86) PCT No.: PCT/US96/16490
§ 371 Date: Aug. 3, 1998
§ 102(e) Date: Aug. 3, 1998
(87) PCT Pub. No.: WO97/14416
PCT Pub. Date: Apr. 24, 1997

(51) Int. Cl.$^7$ ..................................................... A61K 38/16
(52) U.S. Cl. .................. 514/8; 514/13; 514/25; 514/34; 530/300; 530/322; 536/6.4
(58) Field of Search ............................. 536/6.4; 530/322, 530/300; 514/25, 24, 8, 13

(56) References Cited

U.S. PATENT DOCUMENTS

| 5,116,615 | 5/1992 | Gokeen et al. . |
| 5,227,471 | 7/1993 | Wright, Jr. . |
| 5,332,669 | 7/1994 | Deuel . |
| 5,349,066 | 9/1994 | Kaneko et al. . |
| 5,391,723 | 2/1995 | Priest . |
| 5,599,686 | 2/1997 | DeFeo-Jones, et al. . |

FOREIGN PATENT DOCUMENTS

| 0 285 383 A2 | 10/1988 | (EP) . |
| 0 547 691 A1 | 6/1993 | (EP) . |
| WO 92/01936 | 2/1992 | (WO) . |
| WO 96/00503 | 1/1996 | (WO) . |

OTHER PUBLICATIONS

J. Clin. Invest., vol. 76, pp. 1899–1903 (1985), by H. Lilja.
Executive Briefing, vol. 15, pp. 5–9 (Aug. 1994).
Geriatrics, vol. 49, No. 7, pp. 24–31 (Jul. 1994), by R. G. Roberts.
TEM, vol. 6, No. 4, pp. 128–132 (1995), by A. C. Levine.
Urologic Clincs of No. America, vol. 22, No. 2, pp. 333–344 (May 1995), by M. Tchetgen, et al.
Drugs of Today, vol. 29, No. 5 pp. 335–342 (1993), by J. T. Isaacs.
Urology, vol. 43, No. 4, pp. 427–434 (Apr. 1994), by T. Bjork, et al.
World J Urol, vol. 11, pp. 227–232 (1993), by H. C. Ruckle, et al.
Disease Markers, vol. 11, pp. 3–10 (1993), by J. H. Howanitz.
Int. J. Cancer, vol. 55, pp. 590–597 (1993), by L. Hakalahti, et al.
Drugs, vol. 47(1), pp. 66–81 (1994), by M. Jonler, et al.

*Primary Examiner*—Elli Peselev
(74) *Attorney, Agent, or Firm*—David A. Muthard; Mark R. Daniel

(57) ABSTRACT

Novel pharmaceutical compositions useful for the treatment of benign prostatic hyperplasia which comprises novel oligopeptides, which are selectively cleaved by enzymatically active PSA, in conjugation with a cytotoxic agent are described. Methods of treating benign prostate hypertrophy are also disclosed.

23 Claims, 11 Drawing Sheets

1: MetLysProAsnIleIlePheValLeuSerLeuLeuLeuIleLeuGluLysGlnAlaAla –

21: ValMetGlyGlnLysGlyGlySerLysGlyArgLeuProSerGluPheSerGlnPhePro –

41: HisGlyGlnLysGlyGlnHisTyrSerGlyGlnLysGlyLysGlnGlnThrGluSerLys –

61: GlySerPheSerIleGlnTyrThrTyrHisValAspAlaAsnAspHisAspGlnSerArg –

81: LysSerGlnGlnTyrAspLeuAsnAlaLeuHisLysThrThrLysSerGlnArgHisLeu –

101: GlyGlySerGlnGlnLeuLeuHisAsnLysGlnGluGlyArgAspHisAspLysSerLys –

121: GlyHisPheHisArgValValIleHisHisLysGlyGlyLysAlaHisArgGlyThrGln –

141: AsnProSerGlnAspGlnGlyAsnSerProSerGlyLysGlyIleSerSerGlnTyr|Ser –
                                                                                                     CS#5

161: AsnThrGluGluArgLeuTrpValHisGlyLeuSerLysGlnGlnThrSerValSerGly –

181: AlaGlnLysGlyArgLysGlnGlyGlySerGlnSerSerTyrValLeuGlnThrGluGlu –

201: LeuValAlaAsnLysGlnGlnArgGluThrLysAsnSerHisGlnAsnLysGlyHisTyr –

221: GlnAsnValValGluValArgGluGluHisSerSerLysValGlnThrSerLeuCysPro –

241: AlaHisGlnAspLysLeuGlnHisGlySerLysAspIlePheSerThrGlnAspGluLeu –

261: LeuValTyrAsnLysAsnGlnHisGlnThrLysAsnLeuAsnGlnAspGlnHisGly –

CS#3

281: ArgLysAlaAsnLysIleSerTyrGln|SerSerSerThrGluGluArgArgLeuHisTyr –
                                                                                       CS#4

301: GlyGluAsnGlyValGlnLysAspValSerGlnSerSerIleTyrSer|GlnThrGluGlu –

321: LysAlaGlnGlyLysSerGlnLysGlnIleThrIleProSerGlnGluGlnGluHisSer –
                                                         CS#1

341: GlnLysAlaAsnLysIleSerTyrGln|SerSerSerThrGluGluArgArgLeuHisTyr –
                                                                             CS#2

361: GlyGluAsnGlyValGlnLysAspValSerGlnArgSerIleTyrSer|GlnThrGluLys –

381: LeuValAlaGlyLysSerGlnIleGlnAlaProAsnProLysGlnGluProTrpHisGly –

401: GluAsnAlaLysGlyGluSerGlyGlnSerThrAsnArgGluGlnAspLeuLeuSerHis –

421: GluGlnLysGlyArgHisGlnHisGlySerHisGlyGlyLeuAspIleValIleIleGlu –

441: GlnGluAspAspSerAspArgHisLeuAlaGlnHisLeuAsnAsnAspArgAsnProLeu –

461: PheThr –

FIG. 1

| | PEPTIDE | PERCENT PEPTIDE HYDROLYSIS TIME OF INCUBATION (HOURS) | | | | | |
|---|---|---|---|---|---|---|---|
| | | 0.5 | 1 | 2 | 3 | 4 | 20 |
| 1. | SYQSSSTE | ND | 0 | ND | 0 | ND | 0 |
| 2. | ISYQSSSTE | ND | 0 | ND | 0 | ND | 0 |
| 3. | KISYQSSSTE | ND | 10 | ND | 30 | ND | 90 |
| 4. | NKISYQSSSTE | ND | 30 | ND | 70 | ND | 100 |
| 5. | NKISYQSSST | ND | 20 | 30 | ND | ND | 100 |
| 6. | ANKISYQSSSTE | 15 | 25 | ND | ND | 80 | 100 |
| 7. | ANKISYQSSS | 4 | 6 | 16 | 30 | 45 | ND |
| 8. | NKISYQSSS | 2 | 6 | 22 | 44 | 55 | ND |
| 9. | ANKISYQSS | 1 | ND | 12 | ND | 39 | ND |
| 10. | GRKANKISYQS-SSTEERRLHYGENG | 20 | 50 | ND | ND | 90 | 100 |

ND = NOT DETERMINED

FIG.2

| PEPTIDE | SALT | SEQ.ID.NO | % PEPTIDE CLEAVED AT 4 HRS BY YORK PSA |
|---|---|---|---|
| SEMENOGELIN (463 aa) | | | 100 (30 MIN) |
| GRKANKISYQ-SSSTEERRLHYGENG | TFA | 6 | 100 (2 HRS) |
| SQKANKISYQ-SSSTEERRLHYGENG | TFA | 67 | 100 (3 HRS) |
| ANKISYQ-SSSTE | TFA | 11 | 98 |
| ISYQ-SSST | TFA | 68 | 0 |
| NKISYQ-SSST | TFA | 10 | 62 |
| NKISYQ-SSSTE | TFA | 3 | 90 |
| KISYQ-SSSTE | TFA | 9 | 49 |
| SYQ-SSSTE | TFA | 7 | 0 (3 HRS) |
| ISYQ-SSSTE | TFA | 8 | 0 |
| NKISYQ-SSS | TFA | 17 | 55 |
| ANKISYQ-SSS | TFA | 18 | 45 |
| ANKISYQ-SS | TFA | 69 | 39 |
| ANKISYQ-SSSSTE-amide | TFA | 11 | 43 |
| Ac-ANKISYQ-SSSTL | TFA | 70 | 57 |
| Ac-ANKISYQ-SSSTE-amide | TFA | 11 | 40 |
| Ac-ANKISYQ-SSSTL-amide | TFA | 70 | 46 |
| Ac-ANGISYQ-SSSTE-amide | | 71 | 0 |
| Ac-ANPISYQ-SSSTE-amide | | 72 | 0 |
| Ac-ANKISYQ-SASTE-amide | TFA | 73 | 66 |
| Ac-ANKISYQ-SSKTE-amide | TFA | 74 | 80 |
| Ac-ANKISYQ-SSTE-amide | TFA | 75 | 44 |
| Ac-ANKI(dS)YQ-SSSTE-amide | TFA | 76 | 9 |
| Ac-ANK(dI)SYQ-SSSTE-amide | TFA | 77 | 0 |
| Ac-ANKISYQ-SSQTE-amide | TFA | 78 | 55 |
| Ac-ANKISYQ-SAKTE-amide | TFA | 79 | 80 |
| Ac-AN(dK)ISYQ-SSSTE-amide | TFA | 80 | 3 |
| Ac-ANKISYQ-STE-amide | TFA | 81 | 28 |
| Ac-ANKIYQ-SSTE-amide | TFA | 82 | 0 |
| Ac-ANKSYQ-SSTE-amide | TFA | 83 | 10 |
| Ac-ANKASYQ-SASTE-amide | TFA | 84 | 98 |
| Ac-ANEISYQ-SASTE-amide | | 85 | 10 |
| Ac-NKISYQ-SS-amide | TFA | 16 | 30 |
| Ac-KISYQ-SS-amide | TFA | 86 | 15 |
| Ac-SYQ-SSTE-amide | | 87 | 65 |
| Ac-SYQ-SSTL-acid | | 88 | 83 |
| Ac-ASYQ-SSTE-amide | | 89 | 68 |
| Ac-EISYQ-SSSTE-amide | | 90 | 0 |
| Ac-ANEISYQ-SSSTE-amide | | 91 | 0 |

FIG.3

| PEPTIDE | SALT | SEQ.ID.NO | % PEPTIDE CLEAVED AT 4 HRS BY YORK PSA |
|---|---|---|---|
| Ac-ANKISYY-SSSTE-amide | TFA | 92 | 73 |
| Ac-ANKISYY-SASTE-amide | TFA | 93 | 91 |
| Ac-ASYQ-SSL-acid | | 94 | 71 |
| Ac-ANSYQ-SSSTE-amide | | 95 | 28 |
| Ac-ASYQ-SSSTE-amide | | 96 | 64 |
| Ac-SYQ-SSSTE-amide | | 97 | 50 |
| Ac-ANKASYQ-SASTC-amide | TFA | 98 | 78 |
| Ac-Q-SSTE-amide | | 99 | 0 |
| Ac-YQ-SSTE-amide | | 100 | 0 |
| Ac-SQ-SSTE-amide | | 101 | 0 |
| Ac-ANKISQ-SSTE-amide | TFA | 102 | 0 |
| Ac-AN(ORN)ISYQ-SSTE-amide | TFA | 103 | 34 |
| Ac-S(3 PAL)Q-SSTE-amide | | 104 | 4 |
| Ac-S(3,4-C12F)Q-SSTE-amide | | 105 | 6 |
| Ac-SKQ-SSTE-amide | TFA | 106 | 0 |
| Ac-SYQ-SSTL-acid | | 88 | 81 |
| Ac-SYQ-SSSL-acid | | 107 | 98 |
| (e-ACA)-YQ-SSSL-amide | AA | 108 | 0 |
| ANK(N-Me-I)SYQ-SSTE-amide | TFA | 109 | 0 |
| SYQ-SSTE-amide | | 110 | 0 |
| HO(CH2)2CO-YQ-SSTE-amide | | 111 | 0 |
| Ac-SYK-SSTE-amide | TFA | 112 | 5 |
| Ac-SYY-SSTE-amide | | 113 | 93 |
| Ac-SYQ-SSL-NHNH2 | | 114 | 32 |
| Ac-SYQ-SSL-acid | | 115 | 72 |
| DAP-YQ-SSSL-amide | AA | 116 | 0 |

FIG.3A

| PEPTIDE | SALT | SEQ. ID. NO. | TIME TO CLEAVE 50% OF SUBSTRATE BY YORK PSA |
|---|---|---|---|
| SEMONOGELIN (463 aa) | | | 100% AT 30 MIN |
| Ac-hR(Cha)Q-SNNle-acid | TFA | 149 | 4 HR = 0% (PS) |
| Ac-hR(Cha)Q-SNle-acid | TFA | 147 | 200 (PS) |
| Ac-hRhYQ-SSNle-acid | TFA | 148 | 95 (PS) |
| Ac-ANKASYQ-SS-Cha-NHNH2 | TFA | 150 | >240 (4 HR = 31%) |
| Ac-hRYQ-SSP-acid | TFA | 151 | 30 |
| hRYQ-SSH-acid | TFA | 152 | >240 (4 HR = 0%) |
| Ac-hRYQ-SSH-acid | TFA | 152 | 60 |
| hRYQ-SP-acid | TFA | 177 | >240 (4 HR = 0%) |
| Ac-hRYQ-SP-acid | TFA | 177 | >240 (4 HR = 0%) |
| Ac-hRYQ-SN-acid | TFA | 153 | 90 |
| Ac-hRYQ-S-acid | TFA | 187 | >240 (4 HR = 0%) |
| Ac-hRYQ-SSSNle-acid | | 154 | 40 |
| Ac-(Amf)YQ-SSSNle-acid | | 155 | 50 |
| NH2CO-hRYQ-SSSL-acid | TFA | 156 | 60 |
| Ac-ANKAKYQ-SS(Cha)-NHNH2 | TFA | 157 | 240 |
| Ac-(DPL)YQ-SSSNle-acid | TFA | 158 | 120 |
| Ac-(imidazolyl)KYQ-SSL-acid | TFA | 159 | 25 |
| Ac-ANKA(hR)YQ-SSL-acid | TFA | 160 | 105 |
| Ac-(p-NH2-Cha)YQ-SSSNle-acid | TFA | 161 | 140 |
| Ac-(imidazoyl)KYQSSSNle-acid | TFA | 162 | 25 |
| Ac-hR(Cha)Q-SSSNle-acid | TFA | 163 | 120 |
| Ac-hRYQ-SSShR-acid | TFA | 164 | 70 |
| Ac-hRYQ-SSS(MeL) | TFA | 188 | 90 |
| Ac-hRYQ-SSS(Ethylester-L) | | 156 | 85 |
| Ac-ANKA(imidazolyl)KYQ-SSNle-acid | TFA | 165 | 95 |
| Ac-hR(3-Iodo-Y)Q-SSSNle-acid | TFA | 166 | 55 |
| Ac-hR(Me2PO3-Y)Q-SSSNle-acid | TFA | 167 | 4 HR = 0% |
| Ac-hRYQ-SSD-acid | TFA | 168 | 25 |
| Ac-hR(O-Me-Y)Q-SSSNle-acid | TFA | 169 | 4 HR = 0% |
| Ac-ANKAKYQ-SSNle-acid | TFA | 170 | 80 |
| Ac-hR(Cha)Q-SSS(ethylester-L) | | 171 | 4 HR = 36% |
| Ac-(imidazolyl)K(Cha)Q-SSSNle-acid | TFA | 172 | 180 (PS) |
| Ac-hR(TIC)Q-SSSNle-acid | TFA | 179 | 4 HR = 0% |
| Ac-Q-SSSNle-acid | TFA | 189 | 4 HR = 0% |
| Ac-hR(Cha)Q-SSS-acid | TFA | 173 | 120 |
| Ac-hR(Cha)Q-SSNle-acid | TFA | 174 | 60 (PS) |
| Ac-hR(Cha)Q-SPNle-acid | TFA | 175 | 4 HR = 12% |
| Ac-hR(m-fluoro-Y)Q-SSSNle-acid | TFA | 176 | 100 |
| Ac-(7-HO-TIC)Q-SSSNle-acid | TFA | 190 | 4 HR = 0% |

FIG.3B

| DOXORUBICIN-COGENER | SALT | SEQ.ID.NO. | % PEPTIDE CLEAVED AT 4 HOURS BY YORK PSA |
|---|---|---|---|
| Ac-ANKISYQ-SSST-DOX (3') | TFA | 117 | 20 (1 HR) NO SAMPLE LEFT |
| Ac-ANKISYQ-SSSTL-DOX (3') | TFA | 70 | 87 |
| Ac-ANKASYQ-SASTL-DOX (3') | AA | 118 | NA |
| Ac-ANKASYQ-SASL-DOX (3') | AA | 119 | 100 (3 HR) |
| Ac-ANKASYQ-SSSL-DOX (3') | AA | 120 | 100 (3 HR) |
| Ac-ANKASYQ-SSL-DOX (3') | AA | 121 | 91 |
| Ac-SYQ-SST(dL)-DOX (3') |  | 122 | 17 |
| Ac-SYQ-SSSL-DOX (3') |  | 107 | 95 (PS) |
| Ac-ANKASYA-SSSL-DOX (3') | AA | 123 | 0 |
| Ac-KYQ-SSSL-DOX (3') | AA | 124 | 98 (PS) |
| Ac-SYQ-SSKL-DOX (3') | AA | 125 | 88 |
| Ac-SYQ-SSK(dL)-DOX (3') | AA | 126 | 87 |

FIG.5

| DOXORUBICIN-COGENER | SALT | SEQ.ID.NO. | TIME TO CLEAVE 50% OF SUBSTRATE BY YORK PSA |
|---|---|---|---|
| Ac-(ORN)YQ-SSSNle-DOX (3') | AA | 181 | 4 HR = 20% |
| Ac-KAASSSL-DOX (3') | AA | 182 | 10X [ENZ] 20 HR = 11% |
| Ac-hRh(Cha)Q-SSNle-DOX (3') | AA | 149 | 4 HR = 30% |
| Ac-hRYQ-SSP-DOX (3') | | 151 | 45 |
| Ac-hRYQ-SP-DOX (3') | | 177 | >240 (4 HR = 0%) |
| Ac-hRYQ-SSSNle-DOX (3') | | 154 | 190 (PS) |
| Ac-AmfYQ-SSSNle-DOX (3') | | 155 | 110 (PS) |
| NH2CO-hRYQ-SSSL-DOX (3') | | 156 | 105 |
| Ac-KYQ-SSNle-DOX (3') | AA | 146 | >240 (4 HR = 36%) (PS) |
| Ac-KYQ-SKNle-DOX (3') | AA | 178 | >240 (4 HR = 20%) (NO PROD) |
| Ac-(cis-p-NH2Cha)YQSSSNleDOX(3') | | 161 | 240 (PS) |
| Ac-ANKA(hR)YQ-SSL-DOX (3') | | 160 | 60 |
| Ac-hRYQ-SN-DOX (3') | AA | 153 | 90 (PS) |
| Ac-hRYQ-SSH-DOX (3') | AA | 152 | 110 |
| Ac-(imidazolyl)KYQ-SSL-DOX (3') | | 159 | 150 |
| Ac-(imidazolyl)KYQSSSNle-DOX (3') | | 162 | 60 |
| Ac-hR(Cha)Q-SSSNle-DOX (3') | | 163 | 130 |
| Ac-hR(Me2PO3Y)Q-SSSNle-DOX (3') | | 167 | 4 HR = 0% |
| Ac-hRYQ-SSShR-DOX (3') | | 164 | 50 |
| Ac-hR(3-Iodo-Y)Q-SSSNle-DOX (3') | | 166 | 4 HR = 0% (PS) |
| Ac-hR(O-Me-Y)Q-SSSNIE-DOX (3') | | 169 | 4 HR = 20% (PS) |
| Ac-hR(p-NH2-F)Q-SSSNle-DOX (3') | | 179 | 90 (PS) |
| Ac-hR(Cha)Q-SSNle-DOX (3') | | 174 | 120 |
| Ac-hR(Cha)Q-SPNle-DOX (3') | | 175 | 4 HR = 0% |
| Ac(imidazolyl)K(Cha)QSSSNleDOX(3') | | 172 | 180 |
| Ac-hR(TIC)Q-SSSNle-DOX (3') | | 180 | 4 HR = 14% |
| Ac-hR(3-Fluoro)YQSSSNleDOX (3') | | 176 | 4 HR = 26% |
| desAc-vinblastine-LNKASYQ-SSL-DOX | AA | 184 | 70 (PS) |
| Ac-ANKASYQ-SL-DOX (3') | TFA | 193 | 90 |
| Ac-(ORN)YQ-SSSNle-DOX (3') | TFA | 194 | 120 |

FIG.5A

| DOXORUBICIN-CONGENER | SALT | SEQ.ID.NO. | % PEPTIDE CLEAVED/ LNCaP MEDIA 4 HR | % PEPTIDE CLEAVED/ DuPRO MEDIA 4 HR |
|---|---|---|---|---|
| Ac-ANKASYQ-SASL-DOX (3') | AA | 119 | 92 | 13 |
| Ac-ANKASYQ-SSSL-DOX (3') | AA | 121 | 98 | 13 |
| Ac-ANKASYQ-SSL-DOX (3') | | 122 | 95 | 27 |
| Ac-SYQ-SSSL-DOX (3') | | 107 | 63 | 0 |

FIG.6

| CYTOTOXIC AGENT-COGENER | SALT | SEQ.ID.NO | LNCoP CELL KILL EC50 (μM) |
|---|---|---|---|
| Ac-ANKISYQ-SSST-DOX(3') | TFA | 117 | >100 |
| Ac-ANKISYQ-SSSTL-DOX(3') | TFA | 70 | 8.4 |
| Ac-ANKASYQ-SASTL-DOX(3') | AA | 118 | 31 |
| Ac-ANKASYQ-SASL-DOX(3') | AA | 119 | 16 (DuPRO > 100) |
| Ac-ANKASYQ-SSSL-DOX(3') | AA | 120 | 15 |
| Ac-ANKASYQ-SSL-DOX(3') | AA | 121 | 6.5 (DuPRO = 117) |
| Ac-SYQ-SSSL-DOX(3') |  | 144 | 20 (DuPRO > 100)(PS) |
| Ac-ANKASYA-SSSL-DOX(3') | AA | 191 | >100 |
| Ac-KYQ-SSSL-DOX(3') | AA | 124 | 6.5 (DuPRO>100)(PS) |
| Ac-SYQ-SSKL-DOX(3') | AA | 192 | 11.8 (DuPRO>100) |
| Ac-SYQ-SSK(dL)-DOX(3') | AA |  | >100 (DuPRO>100) |
| Ac-hRYQ-SSSL-DOX(3') | AA | 145 | 6.4 (DuPRO>100) |
| Ac-KYQ-SSSNle-DOX(3') | AA | 183 | 4.4 (DuPRO>100) |
| Ac-(ORN)YQ-SSSNle-DOX(3') | AA | 181 | 3.3 (DuPRO = 65) |
| Ac-hRh(Cha)Q-SSSNle-DOX(3') | AA | 149 |  |
| a-Me-A-DX(3') | AA |  | 7.0 (DuPRO = 20.8) |
| M-DOX(3') | AA |  | 6.0 (DuPRO = 13.8) |
|  |  |  | {4.9(DuPRO = 33.3)} |
| G-DOX(3') | AA |  | >100 (DuPRO>100) |
| N-methyl-G-DOX(3') | AA |  | 39.0 (DuPRO = 58.8) |
| NH2(CH2)5-CO-DOX(3') | AA |  | 59.2 (DuPRO > 100) |
| Ac-hRYQ-SSP-DOX(3') |  | 151 | {33.3(DuPR=100)} |
| Ac-hRYQ-SP-DOX(3') |  | 177 | 25.2 (DuPRO = 44.5) |
| Ac-hRYQ-SSSNle-DOX(3') |  | 154 | 4.4(DuPRO = 41.0)(PS) |
| Ac-AmfYQ-SSSNle-DOX(3') |  | 155 | 7.6(DuPRO>100)(PS) |
| NH2CO-hRYQ-SSSL-DOX(3') |  | 156 | 35.7 (DuPRO>100) |
| Ac-KYQ-SSNle-DOX(3') | AA | 146 | 4.6(DuPRO = 76.9)(PS) |
| Ac-KYQ-SKNle-DOX(3') | AA | 178 | 5.7(DuPRO>>100){3.6} |
| Ac-(cis-p-NH2Cha)YQSSNleDOX(3') |  | 161 | 9.8(DuPRO = 47.1)(PS) |
| Ac-ANKA(hR)YQ-SSL-DOX(3') |  | 160 | 7.3(DuPRO>>100) |
| AchRYQ-SN-DOX(3') | AA | 153 | 70.4(DuPRO = 75.0) |
| Ac-hRYQ-SSH-DOX(3') | AA | 152 | 25.4 (DuPRO = 35.7) |
| Ac-(imidazolyl)KYQ-SSL-DOX(3') | AA | 159 | 6.3(DuPRO = 12.8)(PS) |
| Ac-(imidazolyl)KYQSSSNle-DOX(3') |  | 162 | 3.2 (DuPRO = 23) |
|  |  |  | (PS AT 50 mM) |
| Ac-hR(Cha)Q-SSSNle-DOX(3') |  | 163 | 2.3 (DuPRO >>100) |
| Ac-hR(Me2PO3Y)Q-SSSNle-DOX(3') |  | 167 | 8.0 (DuPRO>100) |
| Ac-hRYQ-SSShR-DOX(3') |  | 164 | 32 (DuPRO>100) |
| Ac-hR(3-Iodo-Y)Q-SSSNle-DOX(3') |  | 166 | 12.8 (DuPRO = 60.8) |
| Ac-hR(O-Me-Y)Q-SSSNle-DOX(3') |  | 169 | 7.4 (DuPRO = 13.5) |

FIG.7

| CYTOTOXIC AGENT-COGENER | SALT | SEQ.ID.NO | LNCaP CELL KILL EC50 (μM) |
|---|---|---|---|
| Ac-hR(p-NH2-F)Q-SSSNle-DOX(3') | | 179 | 7.5 (DuPRO>100) |
| Ac-hR(Cha)Q-SSNle-DOX(3') | | 174 | 3.4 (DuPRO>100) |
| Ac-hR(Cha)Q-SPNle-DOX(3') | | 175 | 12.3 (DuPRO>100) |
| Ac-ANKASYQ-SL-DOX(3') | TFA | 193 | 10 (DuPRO>100) |
| Ac-(ORN)YQ-SSSNle-DOX(3') | TFA | 194 | 7.0 (DuPRO>100) |
| Ac-(imidazolyl)K(Cha)QSSSNleDOX(3') | | 172 | 4.0 (DuPRO>100)(PS) |
| Ac-hR(TIC)Q-SSSNle-DOX(3') | | 180 | .3.2(DuPRO = 50.9) |
| Ac-hR(3-Fluoro)YQSSSNleDOX(3') | | 176 | 3.2(DuPRO = 58.8) |
| | | | |
| vinblastine | | | 0.5(DuPRO = 85) |
| DAP-desAc-vinblastine | TFA | | 150 (DuPRO>>100) |
| Ac-KYQ-SSSNle-DAP-desAc-vinblastine | TFA | 183 | 14.7(DuPRO>>100){4.8} |
| Nle-DAP-desAc-vinblastine | TFA | | 5.9(DuPRO>100) |
| desAc-vinblastine-LNKASYQ-SSSL-amide | AA | 184 | 1.6(DuPRO>>100) |

FIG.7A

CONJUGATES USEFUL IN THE TREATMENT OF BENIGN PROSTATIC HYPERPLASIA

BACKGROUND OF THE INVENTION

Benign prostate hyperplasia (or "prostatism") can be seen in almost 100 percent of all men over the age of 80, and changes in the prostate can be discovered in about 50 percent of men by the time they reach the age of 60. Many men with benign prostate hyperplasia (BPH) remain without symptoms, others show slow progression, while others remain stable. However, some 400,000 men a year have symptoms severe enough to require surgery. The most common surgery, transurethral resection, is effective in relieving the symptoms of BPH, although side-effects, including morbidity from the operation itself, mild to severe urinary incontinence and some degree of erectile or ejaculatory dysfunction, have been reported in a limited number of patients.

Normally the prostate remains stable until after the age of 45, when the tissue begins to change, growing and causing the size of the prostate to increase. The enlarging prostate squeezes the urethra, producing the symptoms that characterize BPH. These include difficulty in starting urination (hesitancy), a weak urinary stream, dribbling after urination, and increased frequency or urgency to urinate during the sleep period. Sometimes urination may be painful. The symptoms of obstruction of the urethra can often become more severe if a urinary infection develops one of the common complications of BPH.

Prostate specific Antigen (PSA) is a single chain 33 kDa glycoprotein that is produced almost exclusively by the human prostate epithelium and occurs at levels of 0.5 to 2.0 mg/ml in human seminal fluid (Nadji, M., Taber, S. Z., Castro, A., et al. (1981) Cancer 48:1229; Papsidero, L., Kuriyama, M., Wang, M., et al. (1981). JNCI 66:37; Qui, S. D., Young, C. Y. F., Bihartz, D. L., et al. (1990), J. Urol. 144:1550; Wang, M. C., Valenzuela, L. A., Murphy, G. P., et al. (1979). Invest. Urol. 17:159). The single carbohydrate unit is attached at asparagine residue number 45 and accounts for 2 to 3 kDa of the total molecular mass. PSA is a protease with chymotrypsin-like specificity (Christensson, A., Laurell, C. B., Lilja, H. (1990). Eur. J. Biochem. 194:755–763). It has been shown that PSA is mainly responsible for dissolution of the gel structure formed at ejaculation by proteolysis of the major proteins in the sperm entrapping gel, Semenogelin I and Semenogelin II, and fibronectin (Lilja, H. (1985). J. Clin. Invest. 76:1899; Lilja, H., Oldbring, J., Rannevik, G., et al. (1987). J. Clin. Invest. 80:281; McGee, R. S., Herr, J. C. (1988). Biol. Reprod. 39:499). The PSA mediated proteolysis of the gel-forming proteins generates several soluble Semenogelin I and Semenogelin II fragments and soluble fibronectin fragments with liquefaction of the ejaculate and release of progressively motile spermatoza (Lilja, H., Laurell, C. B. (1984). Scand. J. Clin. Lab. Invest. 44:447; McGee, R. S., Herr, J. C. (1987). Biol. Reprod. 37:431). Furthermore, PSA may proteolytically degrade IGFBP-3 (insulin-like growth factor binding protein 3) allowing IGF to stimulate specifically the growth of PSA secreting cells (Cohen et al., (1992) J. Clin. Endo. & Meta. 75:1046–1053).

PSA complexed to alpha 1-antichymotrypsin is the predominant molecular form of serum PSA and may account for up to 95% of the detected serum PSA (Christensson, A., Björk, T., Nilsson, O., et al. (1993). J. Urol. 150:100–105; Lilja, H., Christensson, A., Dahlén, U. (1991). Clin. Chem. 37:1618–1625; Stenman, U. H., Leinoven, J., Alfthan, H., et al. (1991). Cancer Res. 51:222–226). The prostatic tissue (normal, benign hyperplastic, or malignant tissue) is implicated to predominantly release the mature, enzymatically active form of PSA, as this form is required for complex formation with alpha 1-antichymotrypsin (Mast, A. E., Enghild, J. J., Pizzo, S. V., et al. (1991). Biochemistry 30:1723–1730; Perlmutter, D. H., Glover, G. I., Rivetna, M., et al. (1990). Proc. Natl. Acad. Sci. USA 87:3753–3757). Therefore, in the microenvironment of prostatic PSA secreting cells, the PSA is believed to be processed and secreted in its mature enzymatically active form not complexed to any inhibitory molecule. PSA also forms stable complexes with alpha 2-macroglobulin, but as this results in encapsulation of PSA and complete loss of the PSA epitopes, the in vivo significance of this complex formation is unclear. A free, noncomplexed form of PSA constitutes a minor fraction of the serum PSA (Christensson, A., A., Björk, T., Nilsson, O., et al. (1993). J. Urol. 150:100–105; Lilja, H., Christensson, A., Dahlén, U. (1991). Clin. Chem. 37:1618–1625). The size of this form of serum PSA is similar to that of PSA in seminal fluid (Lilja, H., Christensson, A., Dahlén, U. (1991). Clin. Chem. 37:1618–1625) but it is yet unknown as to whether the free form of serum PSA may be a zymogen; an internally cleaved, inactive form of mature PSA; or PSA manifesting enzyme activity. However, it seems unlikely that the free form of serum PSA manifests enzyme activity, since there is considerable (100 to 1000 fold) molar excess of both unreacted alpha 1-antichymotrypsin and alpha 2-macroglobulin in serum as compared with the detected serum levels of the free 33 kDa form of PSA (Christensson, A., Björk, T., Nilsson, O., et al. (1993). J. Urol. 150:100–105; Lilja, H., Christensson, A., Dahlén, U. (1991). Clin. Chem. 37:1618–1625).

Serum measurements of PSA are useful for monitoring the treatment of adenocarcinoma of the prostate (Duffy, M. S. (1989). Ann. Clin. Biochem. 26:379–387; Brawer, M. K. and Lange, P. H. (1989). Urol. Suppl. 5:11–16; Hara, M. and Kimura, H. (1989). J. Lab. Clin. Med. 113:541–548). Above normal serum concentrations of PSA have also been reported in benign prostatic hyperplasia and subsequent to surgical trauma of the prostate (Lilja, H., Christensson, A., Dahlén, U. (1991). Clin. Chem. 37:1618–1625). Therefore, a cytotoxic compound that could be activated by the proteolytic activity of PSA should be prostate cell specific as well as specific for PSA secreting prostate metastases. Such a specific agent may be effective against BPH without causing the side-effects associated with other therapies.

Accordingly, it is the object of this invention to provide a novel pharmaceutical composition useful for the treatment of benign prostatic hyperplasia which comprises novel oligopeptides, which are selectively cleaved by enzymatically active PSA, in conjugation with a cytotoxic agent.

Another object of this invention is to provide a method of treating benign prostatic hyperplasia which comprises administration of the novel pharmaceutical composition.

SUMMARY OF THE INVENTION

Novel pharmaceutical compositions useful for the treatment of adverse conditions of the prostate, in particular benign prostatic hyperplasia, which comprise novel oligopeptides, which are selectively cleaved by enzymatically active PSA, in conjugation with a pharmaceutical agent are described. Methods of treating such conditions of the prostate are also disclosed.

BRIEF DESCRIPTION OF THE FIGURES

FIGS. 1 and 1A: Primary Amino Acid Sequence of Semenogelin I: The primary amino acid sequence of Semenogelin I is shown. (SEQ.ID.NO.: 1) The PSA proteolytic cleavage sites ("CS") are shown (numbered in order of the relative affinity of a site towards PSA hydrolysis) and the protein fragments are numbered sequentially starting at the amino terminus.

FIG. 2: Cleavage Affinity of Synthetic Oligopeptides: A nested set of synthetic oligopeptides was prepared and the oligopeptides were digested with enzymatically active free PSA for various times. The results are shown in Table 2. All of the oligopeptides were tested as trifluoroacetate salts.

FIGS. 3, 3A and 3B: Cleavage Affinity of Synthetic Oligopeptides: Synthetic oligopeptides were prepared and the oligopeptides were digested with enzymatically active free PSA for four (4) hours. The percentage of the oligopeptide that is cleaved in this period of time is listed. The results are shown in Table 4. Table 4a shows the amount of time (in minutes) required for 50% cleavage of the noted oligopeptides with enzymatically active free PSA. If no salt is indicated for an oligopeptide, the free base was tested.

FIGS. 5 and 5A: Cleavage Affinity of Oligopeptides in Conjugation with Doxorubicin by Free PSA In Vitro: Oligopeptides-doxorubicin conjugates were prepared and the conjugates were digested with enzymatically active free PSA for four (4) hours. The percentage conjugate that is enzymatically cleaved in the oligopeptide in this period of time is listed. The results are shown in Table 5. Table 5a shows the amount of time (in minutes) required for 50% cleavage of the noted oligopeptide-cytotoxic agent conjugates with enzymatically active free PSA. If no salt is indicated for the conjugate, the free conjugate was tested.

FIG. 6: Cleavage Affinity of Oligopeptides in Conjugation with Doxorubicin in Cell Conditioned Media: Oligopeptides-doxorubicin conjugates were reacted for four (4) hours with cell culture media that had been conditioned by exposure to LNCaP cells (which are known to secrete free PSA) or DuPRO cell (which do not secrete free PSA). The percentage conjugate that is enzymatically cleaved in the oligopeptide in this period of time is listed. The results are shown in Table 6.

FIG. 7: Cytotoxicity Data of Cleavable Oligopeptide-Doxorubicin Conjugates: The data in Table 7 shows cytotoxicity (as $EC_{50}$) of conjugates of doxorubicin covalently bound to an oligopeptide that contain a free PSA proteolytic cleavage site against a cancer cell line that is known to secrete free PSA. Also shown for selected conjugates is the cytotoxicity of the conjugate against a cell line (DuPRO) which does not secrete free PSA. If no salt is indicated for the conjugate, the free conjugate was tested.

DETAILED DESCRIPTION OF THE INVENTION

Figure 4:
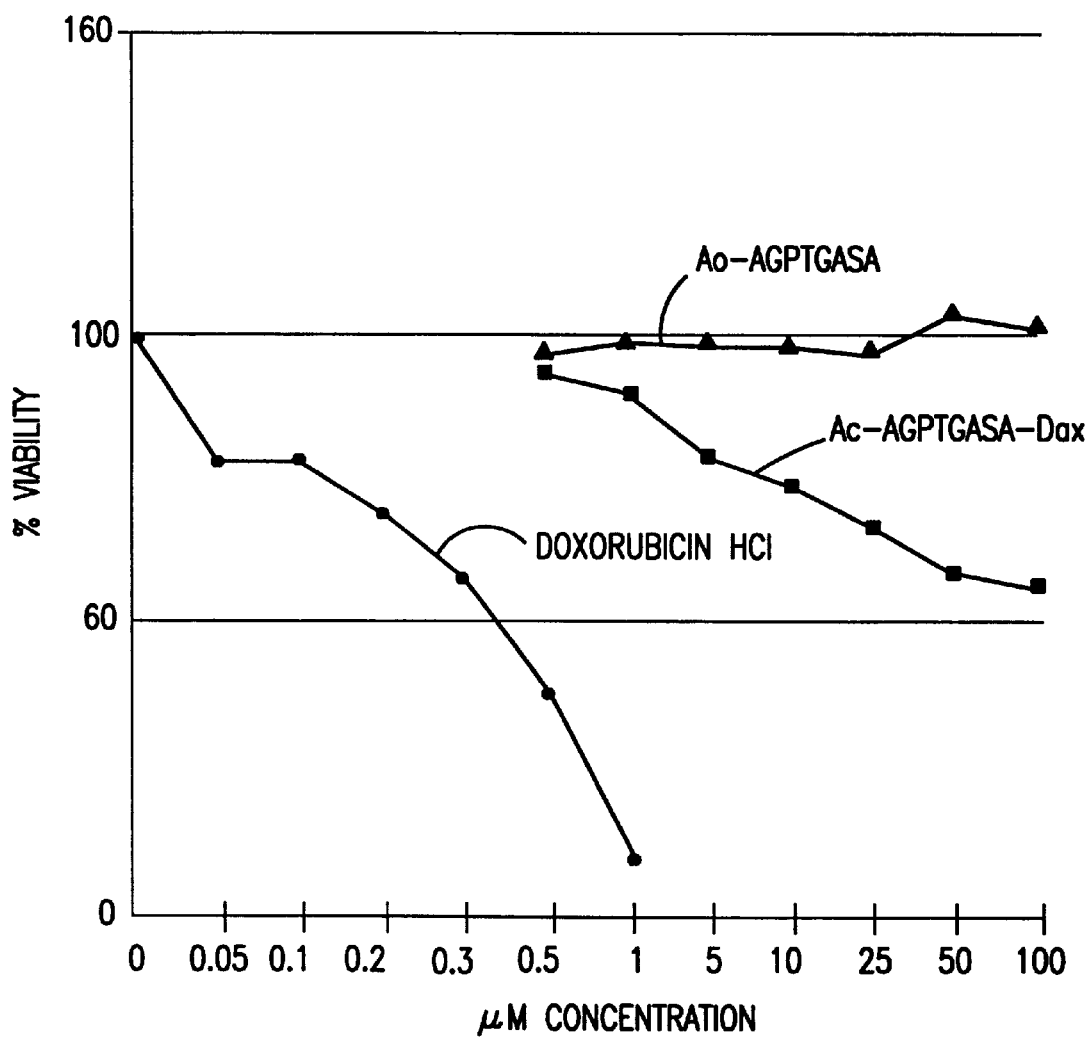
FIG. 4: Cytotoxicity Data of Non-cleavable Oligopeptide-Doxorubicin Conjugates: The data of the figure shows comparative cytotoxicity of doxorubicin and a conjugate of doxorubicin covalently bound to an oligopeptide (Compound 12d) that does not contain the free PSA proteolytic cleavage site. The $EC_{50}$ for doxorubicin is 0.3 $\mu$M, while the acetylated oligopeptide modified doxorubicin has an $EC_{50}$ that has been reduced by greater than 300 fold. This conjugate had no HPLC detectable contamination with unmodified doxorubicin. The oligopeptide alone had no detectable cell killing activity.

The present invention relates to pharmaceutical compositions that comprise conjugates that contain oligopeptides, which are specifically recognized by the free prostate specific antigen (PSA) and are capable of being proteolytically cleaved by the enzymatic activity of the free prostate specific antigen, and pharmaceutical agents covalently linked to such oligopeptides directly or through a linker unit, or pharmaceutically acceptable salts thereof. In particular, this invention is directed to such conjugates wherein the pharmaceutical agent is a cytotoxic agent. The present invention also relates to a novel method of treating adverse conditions of the prostate, in particular benign prostatic hyperplasia, which utilizes these compositions.

Such oligopeptides include oligomers that comprise an amino acid sequence selected from:

a) AsnLysIleSerTyrGln|Ser (SEQ.ID.NO.: 13),
b) LysIleSerTyrGln|Ser (SEQ.ID.NO.: 14),
c) GlyGluAsnGlyValGlnLysAspValSerGlnXaaSerIleTyr|SerGlnThrGlu (SEQ.ID.NO.: 15),
d) GlyLysGlyIleSerSerGlnTyr|SerAsnThrGluGluArgLeu (SEQ.ID.NO.: 2),
e) AsnLysIleSerTyrTyr|Ser (SEQ.ID.NO.: 127),
f) AsnLysAlaSerTyrGln|Ser (SEQ.ID.NO.: 128),
g) SerTyrGln|SerSer (SEQ.ID.NO.: 129);
h) LysTyrGln|SerSer (SEQ.ID.NO.: 140);
i) hArgTyrGln|SerSer (SEQ.ID.NO.: 141);
j) hArgChaGln|SerSer (SEQ.ID.NO.: 185); and
k) TyrGln|SerSer (SEQ.ID.NO.: 186);

wherein hArg is homoarginine, Cha is cyclohexylalanine and Xaa is any natural amino acid.

In an embodiment of the instant invention, the oligopeptides include oligomers that comprise an amino acid sequence that is selected from:

a) AsnLysIleSerTyrGln|SerSer (SEQ.ID.NO.: 16),
b) AsnLysIleSerTyrGln|SerAla (SEQ.ID.NO.: 130),
c) AsnLysIleSerTyrGln|SerSerSer (SEQ.ID.NO.: 17),
d) AlaAsnLysIleSerTyrGln|SerSerSer (SEQ.ID.NO.: 18),
e) LysIleSerTyrGln|SerSerSerThrGlu (SEQ.ID.NO.: 19),
f) GlyGluAsnGlyValGlnLysAspValSerGlnArgSerIleTyr|SerGlnThrGlu (SEQ.ID.NO.: 4),
g) GlyGluAsnGlyValGlnLysAspValSerGlnSerSerleTyr|SerGlnThrGlu (SEQ.ID.NO.: 5),
h) AlaAsnLysIleSerTyrTyr|Ser (SEQ.ID.NO.: 131),
i) AlaAsnLysAlaSerTyrGln|Ser (SEQ.ID.NO.: 132),
j) SerTyrGln|SerSerThr (SEQ.ID.NO.: 133),
k) SerTyrGln|SerSerSer (SEQ.ID.NO.: 134),
l) LysTyrGln|SerSerSer (SEQ.ID.NO.: 142),
m) hArgTyrGln|SerSerSer (SEQ.ID.NO.: 143), and
n) SerTyrGln|SerSerLeu (SEQ.ID.NO.: 135);

or the pharmaceutically acceptable salt thereof.

In a more preferred embodiment of the instant invention, the oligopeptides include oligomers that comprise an amino acid sequence that is selected from:

a) AsnLysIleSerTyrGln|SerSerSerThr (SEQ.ID.NO.: 10),
b) AlaAsnLysIleSerTyrGln|SerAla (SEQ.ID.NO.: 136),
c) AsnLysIleSerTyrGln|SerSerSerThrGlu (SEQ.ID.NO.: 3),
d) AlaAsnLysIleSerTyrGln|SerSerSerThrGlu (SEQ.ID.NO.: 11),
e) GlyGluAsnGlyValGlnLysAspValSerGlnArgSerIleTyr|SerGlnThrGlu (SEQ.ID.NO.: 4),
f) AlaAsnLysIleSerTyrTyr|SerSer (SEQ.ID.NO.: 137),
g) AlaAsnLysIleSerTyrTyr|SerAla (SEQ.ID.NO.: 138),
h) AlaAsnLysAlaSerTyrGln|SerAla (SEQ.ID.NO.: 139),
i) AlaSerTyrGln|SerSerLeu (SEQ.ID.NO.: 94);

or the pharmaceutically acceptable salt thereof.

In a further embodiment of the instant invention, the oligopeptides include oligomers that comprise an amino acid sequence that is selected from:
a) GlyArgLysAlaAsnLysIleSerTyrGln|SerSerSerThrGluGlu ArgArg LeuHisTyr GlyGluAsnGly (SEQ.ID.NO.: 6).

The phrase "oligomers that comprise an amino acid sequence" as used hereinabove, and elsewhere in the Detailed Description of the Invention, describes oligomers of from about 6 to about 100 amino acids residues which include in their amino acid sequence the specific amino acid sequence decribed and which are therefore proteolytically cleaved within the amino acid sequence described by free PSA. Thus, for example, the following oligomer: GlnLeuAspAsnLysIleSerTyrGln|SerSerSerThrHisGlnSerSer (SEQ.ID.NO.: 20) comprises the amino acid sequence: AsnLysIleSerTyrGln|SerSerSerThr (SEQ.ID.NO.: 10) and would therefore come within the instant invention. It is understood that such oligomers do not include semenogelin I and semenogelin II.

It is also understood that the instant invention includes oligomers wherein the N-terminus amino acid or the C-terminus amino acid, or both terminus amino acids are modified. Such modifications include, but are not limited to, acylation of the amine group at the N-terminus and formation of an amide to replace the carboxylic acid at the C-terminus. Addition of such moieties may be performed during solid-phase synthesis of the oligomer; thus, attachment of the C-terminus amino acid to a solid phase resin may be through an amine which results in an amide moiety upon acidic cleavage of the oligomer from the resin. Thus the following compounds are considered "oligomers that comprise an amino acid sequence" as used hereinabove and are meant to be illustrative and are not limiting:

AlaAsnLysIleSerTyrGln|SerSerSerThrGlu-amide (SEQ.ID.NO.: 11)
Ac-AlaAsnLysIleSerTyrGln|SerSerSerThrLeu (SEQ.ID.NO.: 70)
Ac-AlaAsnLysIleSerTyrGln|SerSerSerThrGlu-amide (SEQ.ID.NO.: 11)
Ac-AlaAsnLysIleSerTyrGln|SerSerSerThrLeu-amide (SEQ.ID.NO.: 70)
Ac-AlaAsnLysIleSerTyrGln|SerAlaSerThrGlu-amide (SEQ.ID.NO.: 73)
Ac-AlaAsnLysIleSerTyrGln|SerSerLysThrGlu-amide (SEQ.ID.NO.: 74)
Ac-AlaAsnLysIleSerTyrGln|SerSerThrGlu-amide (SEQ.ID.NO.: 75)
Ac-AlaAsnLysIleSerTyrGln|SerSerGlnThrGlu-amide (SEQ.ID.NO.: 78)
Ac-AlaAsnLysIleSerTyrGln|SerAlaLysThrGlu-amide (SEQ.ID.NO.: 79)
Ac-AlaAsnLysIleSerTyrGln|SerThrGlu-amide (SEQ.ID.NO.: 81)
Ac-AlaAsnLysSerTyrGln|SerThrGlu-amide (SEQ.ID.NO.: 82)
Ac-AlaAsnLysAlaSerTyrGln|SerAlaSerThrGlu-amide (SEQ.ID.NO.: 84)
Ac-AlaAsnGluIleSerTyrGln|SerAlaSerThrGlu-amide (SEQ.ID.NO.: 85)
Ac-AsnLysIleSerTyrGln|SerSer-amide (SEQ.ID.NO.: 16)
Ac-LysIleSerTyrGln|SerSer-amide (SEQ.ID.NO.: 86)
Ac-SerTyrGln|SerSerThrGlu-amide (SEQ.ID.NO.: 87)
Ac-AlaSerTyrGln|SerSerThrGlu-amide (SEQ.ID.NO.: 89)
Ac-AlaAsnLysIleSerTyrTyr|SerSerSerThrGlu-amide (SEQ.ID.NO.: 92)
Ac-AlaAsnLysIleSerTyrTyr|SerAlaSerThrGlu-amide (SEQ.ID.NO.: 93)
Ac-AlaSerTyrGln|SerSerLeu-amide (SEQ.ID.NO.: 94)
Ac-AlaAsnSerTyrGln|SerSerSerThrGlu-amide (SEQ.ID.NO.: 95)
Ac-AlaSerTyrGln|SerSerSerThrGlu-amide (SEQ.ID.NO.: 96)
Ac-SerTyrGln|SerSerSerThrGlu-amide (SEQ.ID.NO.: 97)
Ac-AlaAsnLysAlaSerTyrGln|SerAlaSerCys-amide (SEQ.ID.NO.: 98)
Ac-hArg(Cha)Gln|SerNle-Acid (SEQ.ID.NO.: 147)
Ac-hArghTyrGln|SerSerNle-Acid (SEQ.ID.NO.: 148)
Ac-hArgh(Cha)Gln|SerSerNle-Acid (SEQ.ID.NO.: 149)
Ac-AlaAspLysAlaSerTyrGln|SerSer-Cha-NHNH$_2$ (SEQ.ID.NO.: 150)
Ac-hArgTyrGln|SerSerPro-Acid (SEQ.ID.NO.: 151)
Ac-hArgTyrGln|SerSerHis-Acid (SEQ.ID.NO.: 152)
Ac-hArgTyrGln|SerAsn-Acid (SEQ.ID.NO.: 153)
Ac-hArgTyrGln|SerSerNle-Acid (SEQ.ID.NO.: 154)
Ac-(Amf)TyrGln|SerSerSerNle-Acid (SEQ.ID.NO.: 155)
H$_2$NCO-hArgTyrGln|SerSerSerLeu-Acid (SEQ.ID.NO.: 156)
Ac-AlaAspLysAlaLysTyrGln|SerSer(Cha)-NHNH2 (SEQ.ID.NO.: 157)
Ac-(DPL)TyrGln|SerSerSerNle-Acid (SEQ.ID.NO.: 158)
Ac-(imidazole)LysTyrGln|SerSerLeu-Acid (SEQ.ID.NO.: 159)
Ac-AlaAspLysAla(hArg)TyrGln|SerSerLeu-Acid (SEQ.ID.NO.: 160)
Ac-(p-NH2-Cha)TyrGln|SerSerSerNle-Acid (SEQ.ID.NO.: 161)
Ac(imidazolyl)LysTyrGln|SerSerSerNle-Acid (SEQ.ID.NO.: 162)
Ac-hArg(Cha)Gln|SerSerSerNle-Acid (SEQ.ID.NO.: 163)
Ac-hArgTyrGln|SerSerSerhArg-Acid (SEQ.ID.NO.: 164)
Ac-hArgTyrGln|SerSerSer(MeLeu) (SEQ.ID.NO.: 188)
Ac-hArgTyrGln|SerSerSer(Ethylester-Leu) (SEQ.ID.NO.: 156)
Ac-AlaAspLysAla(imidazoleLys)TyrGln|SerSerNle-Acid (SEQ.ID.NO.: 165)
Ac-hArg(3-Iodo-Tyr)Gln|SerSerSerNle-Acid (SEQ.ID.NO.: 166)
Ac-hArg(Me$_2$PO$_3$-Tyr)Gln|SerSerSerNle-Acid (SEQ.ID.NO.: 167)
Ac-hArgTyrGln|SerSerAsp-Acid (SEQ.ID.NO.: 168)
Ac-hArg(O-Me-Tyr)Gln|SerSerSerNle-Acid (SEQ.ID.NO.: 169)
Ac-AlaAspLysAlaLysTyrGln|SerSerNle-Acid (SEQ.ID.NO.: 170)
Ac-hArg(Cha)Gln|SerSerSer(ethylester-Leu) (SEQ.ID.NO.: 171)
Ac-(imidazolyl)Lys(Cha)Gln|SerSerSerNle-Acid (SEQ.ID.NO.: 172)
Ac-hArg(Cha)Gln|SerSerSer-Acid (SEQ.ID.NO.: 173)
Ac-hArg(Cha)Gln|SerSerNle-Acid (SEQ.ID.NO.: 174)
Ac-hArg(Cha)Gln|SerProNle-Acid (SEQ.ID.NO.: 175) and
Ac-hArg(m-fluoro-Tyr)Gln|SerSerSerNle-Acid (SEQ.ID.NO.: 176),
or the pharmaceutically acceptable salt thereof.

A person of ordinary skill in the peptide chemistry art would readily appreciate that certain amino acids in a biologically active oligopeptide may be replaced by other homologous, isosteric and/or isoelectronic amino acids wherein the biological activity of the original oligopeptide has been conserved in the modified oligopeptide. Certain unnatural and modified natural amino acids may also be utilized to replace the corresponding natural amino acid in the oligopeptides of the instant invention. Thus, for example, tyrosine may be replaced by 3-iodotyrosine, 2-methyltyrosine, 3-fluorotyrosine, 3-methyltyrosine and the like. Further for example, lysine may be replaced with N'-(2-imidazolyl)lysine and the like. The following list of amino acid replacements is meant to be illustrative and is not limiting:

| Original Amino Acid | Replacement Amino Acid(s) |
|---|---|
| Ala | Gly |
| Arg | Lys, Ornithine |
| Asn | Gln |
| Asp | Glu |
| Glu | Asp |
| Gln | Asn |
| Gly | Ala |
| Ile | Val, Leu, Met, Nle |
| Leu | Ile, Val, Met, Nle |
| Lys | Arg, Ornithine |
| Met | Leu, Ile, Nle, Val |
| Ornithine | Lys, Arg |
| Phe | Tyr, Trp |
| Ser | Thr |
| Thr | Ser |
| Trp | Phe, Tyr |
| Tyr | Phe, Trp |
| Val | Leu, Ile, Met, Nle |

Thus, for example, the following oligopeptides may be synthesized by techniques well known to persons of ordinary skill in the art and would be expected to be proteolytically cleaved by free PSA:
AsnArgIleSerTyrGln|Ser (SEQ.ID.NO.: 21)
AsnLysValSerTyrGln|Ser (SEQ.ID.NO.: 22)
AsnLysMetSerTyrGln|SerSer (SEQ.ID.NO.: 23)
AsnLysLeuSerTyrGln |SerSer (SEQ.ID.NO.: 24)
AsnLysIleThrTyrGln|SerSerSer (SEQ.ID.NO.: 25)
AsnLysIleSerPheGln|SerSerSer (SEQ.ID.NO.: 26)
AsnLysIleSerTrpGln|SerSerSerThr (SEQ.ID.NO.: 27)
AsnLysIleSerTyrAsn|SerSerSerThr (SEQ.ID.NO.: 28)
AsnLysIleSerTyrGln|ThrSerSerThr (SEQ.ID.NO.: 29)
AsnLysIleSerTyrGln|Ser (SEQ.ID.NO.: 30)
GlnLysIleSerTyrGln|SerSer (SEQ.ID.NO.: 31)
AsnArgIleThrTyrGln|SerSerSer (SEQ.ID.NO.: 32)
AsnArgIleSerPheGln|SerSerSerThr (SEQ.ID.NO.: 33)
AsnArgIleSerTrpGln|SerSerSerThr (SEQ.ID.NO.: 35)
AsnArgIleSerTyrGln|ThrSerSerThr (SEQ.ID.NO.: 36)
AsnLysIleThrTyrGln|ThrSerSerThr (SEQ.ID.NO.: 37)
AsnLysLeuSerTyrGln|ThrSerSerThr (SEQ.ID.NO.: 38)
GlnLysLeuSerTyrGln|SerSerSerThr (SEQ.ID.NO.: 39)
AsnArgLeuSerTyrGln|ThrSerSerThr (SEQ.ID.NO.: 40)
AsnLysValSerPheGln|SerSerSerThr (SEQ.ID.NO.: 41)
AsnArgValSerTrpGln|SerSerSerThr (SEQ.ID.NO.: 42)
GlnLysValSerTyrGln|SerSerSerThr (SEQ.ID.NO.: 43)
GlnLysIleSerTyrGln|ThrSerSerThr (SEQ.ID.NO.: 34)
AsnLysIleSerTyrGln|SerSerSerThr (SEQ.ID.NO.: 44);
or the pharmaceutically acceptable salt thereof.

Similarly, the following oligopeptides may be synthesized by techniques well known to persons of ordinary skill in the art and would be expected to be proteolytically cleaved by free PSA:
GlyGluGlnGlyValGlnLysAspValSerGlnSerSerIleTyr|SerGln ThrGlu (SEQ.ID.NO.: 45),
GlyGluAsnGlyLeuGlnLysAspValSerGlnSerSerIleTyr|Ser GlnThrGlu (SEQ.ID.NO.: 47),
GlyGluAsnGlyValAsnLysAspValSerGlnSerSerIleTyr|Ser GlnThrGlu (SEQ.ID.NO.: 48),
GlyGluAsnGlyValGlnArgAspValSerGlnArgSerIleTyr|Ser GlnThrGlu (SEQ.ID.NO.: 49),
GlyGluAsnGlyValGlnLysAspValSerGlnLysSerIleTyr|Ser GlnThrGlu (SEQ.ID.NO.: 50),
GlyGluAsnGlyValGlnLysAspLeuSerGlnThrSerIleTyr|Ser GlnThrGlu (SEQ.ID.NO.: 51),
GlyGluAsnGlyValGlnLysAspValSerGlnSerSerIlePhe|Ser GlnThrGlu (SEQ.ID.NO.: 52),
GlyGluAsnGlyValGlnLysAspMetSerGlnSerSerIleTyr|Thr GlnThrGlu (SEQ.ID.NO.: 53),
GlyGluAsnGlyValGlnLysAspValSerGlnArgSerIleTyr|Thr GlnThrGlu (SEQ.ID.NO.: 54),
GlyGluAsnGlyValGlnLysAspValSerGinSerSerIleTyr|Ser GlnSerGlu (SEQ.ID.NO.: 55),
GlyGluAsnGlyValGlnLysAspValSerGlnArgSerIleTyr|Ser AsnThrGlu (SEQ.ID.NO.: 56),
GlyLysAlaIleSerSerGlnTyr|SerAsnThrGluGluArgLeu (SEQ.ID.NO.: 57),
GlyArgGlyIleSerSerGlnTyr|SerAsnThrGluGluArgLeu (SEQ.ID.NO.: 59),
GlyLysGlyIleThrSerGlnTyr|SerAsnThrGluGluArgLeu (SEQ.ID.NO.: 60),
GlyLysGlyIleSerThrGlnTyr|SerAsnThrGluGluArgLeu (SEQ.ID.NO.: 61),
GlyLysGlyIleSerSerAsnTyr|SerAsnThrGluGluArgLeu (SEQ.ID.NO.: 62),
AlaLysGlyIleSerSerGlnTyr|SerAsnThrGluGluArgLeu (SEQ.ID.NO.: 63),
GlyLysGlyIleSerSerGlnPhe|SerAsnThrGluGluArgLeu (SEQ.ID.NO.: 64),
GlyLysGlyIleSerSerGlnTyr|ThrAsnThrGluGluArgLeu (SEQ.ID.NO.: 65),
GlyLysGlyIleSerSerGlnTyr|SerAsnSerGluGluArgLeu (SEQ.ID.NO.: 58), and
GlyLysGlyIleSerSerGlnTyr|SerAsnThrAspGluArgLeu (SEQ.ID.NO.: 46);
and the like.

The inclusion of the symbol "|" within an amino acid sequence indicates the point within that sequence where the oligopeptide is proteolytically cleaved by free PSA.

The compounds of the present invention may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration The following abbreviations are utilized in the specification and figures to denote the indicated amino acids and moieties:

| | |
|---|---|
| hR or hArg: | homoarginine |
| hY or hTyr: | homotyrosine |
| Cha: | cyclohexylalanine |
| Amf: | 4-aminomethylphenylalanine |
| DPL: | 2-(4,6-dimethylpyrimidinyl)lysine |
| (imidazolyl)K: | N'-(2-imidazolyl)lysine |
| Me$_2$PO$_3$—Y: | O-dimethylphosphotyrosine |
| O—Me—Y: | O-methyltyrosine |
| TIC: | tetrahydro-3-isoquinoline carboxylic acid |
| MeL: | 2-keto-3-amino-5-methylhexane |
| DAP: | 1,3-diaminopropane |
| TFA: | trifluoroacetic acid |
| AA: | acetic acid |

The method of treatment of the instant invention utilizes pharmaceutical compositions whose pharmaceutical activity is specific for cells that secrete enzymatically active PSA. Such compositions comprise the oligopeptides described herein above covalently bonded directly, or through a linker unit, to a pharmaceutical agent. Such a combination of an oligopeptide and pharmaceutical agent may be termed a conjugate. The pharmaceutical agent component of the conjugate may be selected from known compounds useful for treating conditions of the prostate, whose site of biological activity or the desired target of the biological activity is within the prostate or in close proximity to the prostate. Such pharmaceutical agents include, but are not limited to cytotoxic agents.

In a preferred embodiment, the method of treatment of the instant invention utilizes cytotoxic compositions whose cytotoxicity is specific for cells that secrete enzymatically active PSA. Such compositions comprise the oligopeptides, described herein above, covalently bonded directly, or through a linker unit, to a cytotoxic agent. Ideally, the cytotoxic activity of the cytotoxic agent is greatly reduced or absent when the oligopeptide containing the PSA proteolytic cleavage site is bonded directly, or through a chemical linker, to the cytotoxic agent and is intact. Also ideally, the cytotoxic activity of the cytotoxic agent increases significantly or returns to the activity of the unmodified cytotoxic agent upon proteolytic cleavage of the attached oligopeptide at the cleavage site. While it is not necessary for practicing this aspect of the invention, a preferred embodiment of this aspect of the invention is a conjugate wherein the oligopeptide, and the linker unit if present, are detached from the cytotoxic agent by the proteolytic activity of the free PSA and any other native proteolytic enzymes present in the tissue proximity, thereby releasing unmodified cytotoxic agent into the physiological environment at the place of proteolytic cleavage. Pharmaceutically acceptable salts of the conjugates are also included.

It is understood that the oligopeptide of the instant invention that is conjugated to the cytotoxic agent, whether through a direct covalent bond or through a linker unit, does not need to be the oligopeptide that has the greatest recognition by free PSA and is most readily proteolytically cleaved by free PSA. Thus, the oligopeptide that is selected for incorporation in such an anti-BPH composition will be chosen both for its selective, proteolytic cleavage by free PSA and for the cytotoxic activity of the cytotoxic agent-proteolytic residue conjugate (or, in what is felt to be an ideal situation, the unmodified cytotoxic agent) which results from such a cleavage.

Because the conjugates utilized in the instant invention can be used for modifying a given biological response, cytotoxic agent is not to be construed as limited to classical chemical therapeutic agents. For example, the cytotoxic agent may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

The preferred cytotoxic agents include, in general, alkylating agents, antiproliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, the taxanes and the podophyllotoxins. Particularly useful members of those classes include, for example, doxorubicin, carminomycin, daunorubicin, aminopterin, methotrexate, methopterin, dichloro-methotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine, taxol and the like. Other useful cytotoxic agents include estramustine, cisplatin and cyclophosphamide. One skilled in the art may make chemical modifications to the desired cytotoxic agent in order to make reactions of that compound more convenient for purposes of preparing conjugates of the invention.

A highly preferred group of cytotoxic agents for the present invention include drugs of the following formulae:

THE METHOTREXATE GROUP OF FORMULA (1):

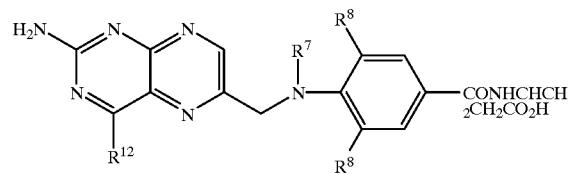

(1)

in which $R^{12}$ is amino or hydroxy;

$R^7$ is hydrogen or methyl;

$R^8$ is hydrogen, fluoro, chloro, bromo or iodo;

$R^9$ is hydroxy or a moiety which completes a salt of the carboxylic acid;

THE MITOMYCIN GROUP OF FORMULA (2):

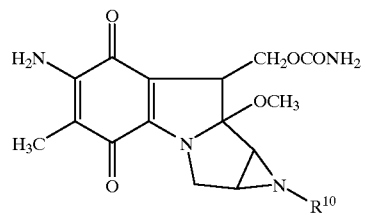

(2)

in which $R^{10}$ is hydrogen or methyl;

THE BLEOMYCIN GROUP OF FORMULA (3)
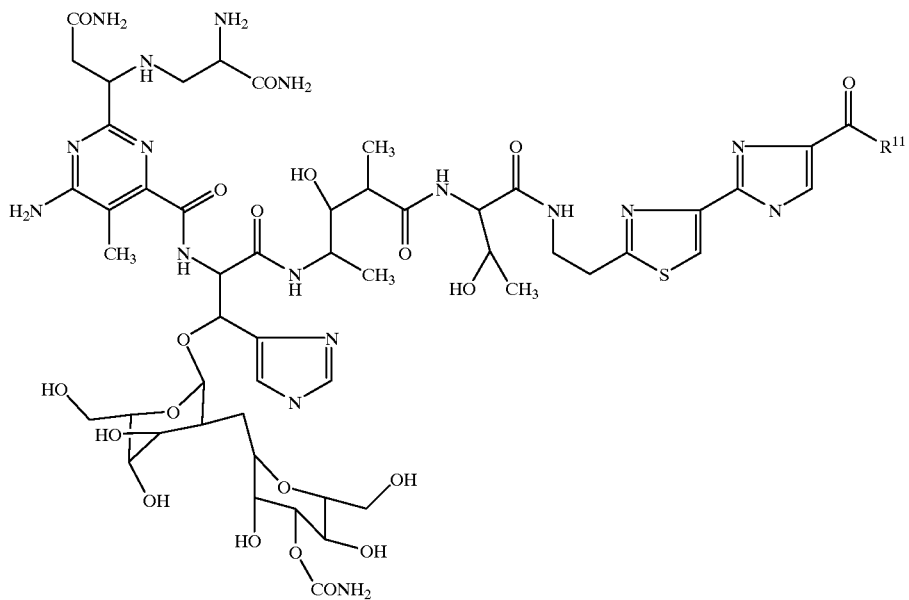
(3)
in which $R^{11}$ is hydroxy, amino, $C_1$–$C_3$ alkylamino, di($C_1$–$C_3$ alkyl)amino, $C_4$–$C_6$ polymethylene amino,
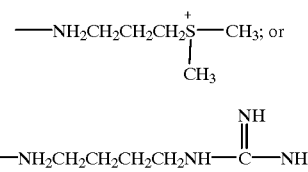
MELPHALEN OF FORMULA (4):
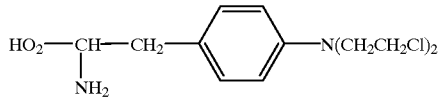
(4)
6-MERCAPTOPURINE OF FORMULA (5):
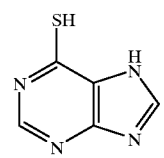
(5)
A CYTOSINE ARABINOSIDE OF FORMULA (6):
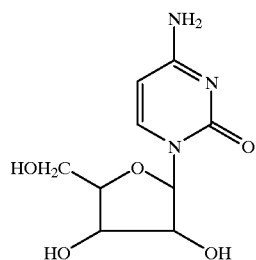
(6)
THE PODOPHYLLOTOXINS OF FORMULA (7):
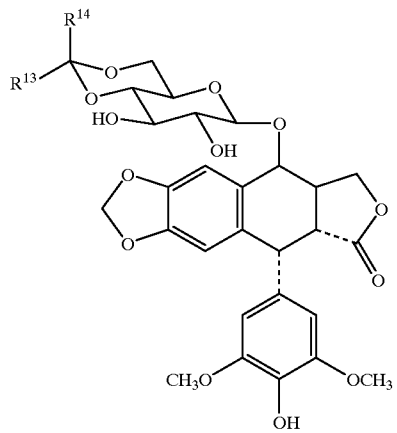
(7)
in which
$R^{13}$ is hydrogen or methyl;
$R^{14}$ is methyl or thienyl;
or a phosphate salt thereof;

THE VINCA ALKALOID GROUP PF DRUGS OF FORMULA (8):

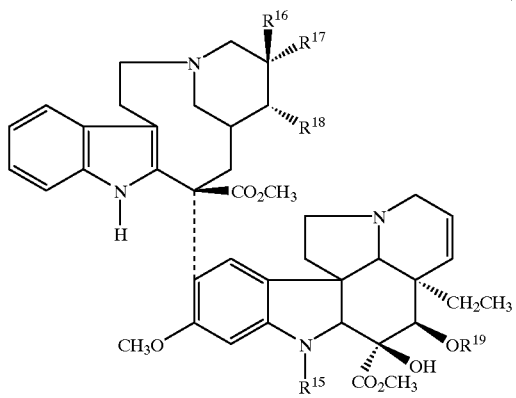

(8)

in which

R$^{15}$ is H, CH$_3$ or CHO; when R$^{17}$ and R$^{18}$ are taken singly;

R$^{18}$ is H, and one of R$^{16}$ and R$^{17}$ is ethyl and the other is H or OH; when R$^{17}$ and R$^{18}$ are taken together with the carbons to which they are attached, they form an oxirane ring in which case R$^{16}$ is ethyl;

R$^{19}$ is hydrogen, (C$_1$–C$_3$ alkyl)-CO, or chlorosubstituted (C$_1$–C$_3$ alkyl)-CO;

DIFLUORONUCLEOSIDES OF FORMULA (9):

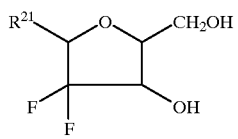

(9)

in which

R$^{21}$ is a base of one of the formulae:

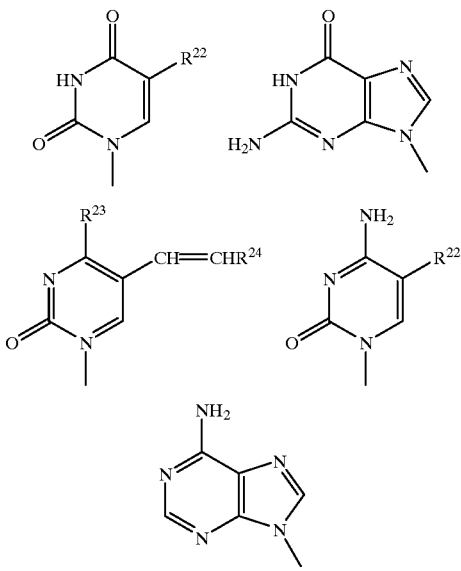

in which

R$^{22}$ is hydrogen, methyl, bromo, fluoro, chloro or iodo;

R$^{23}$ is —OH or —NH$_2$;

R$^{24}$ is hydrogen, bromo, chloro or iodo; or,

THE ANTHRACYCLINES ANTIBIOTICS OF FORMULA (10):

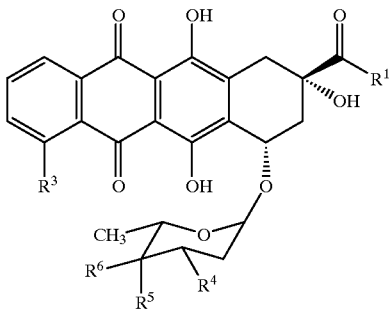

(10)

wherein

R$^{1}$ is —CH$_3$, —CH$_2$OH, —CH$_2$OCO(CH$_2$)$_3$CH$_3$, or —CH$_2$OCOCH(OC$_2$H$_5$)$_2$;

R$^{3}$ is —OCH$_3$, —OH or —H;

R$^{4}$ is —NH$_2$, —NHCOCF$_3$, 4-morpholinyl, 3-cyano-4-morpholinyl, 1-piperidinyl, 4-methoxy-1-piperidinyl, benzylamine, dibenzylamine, cyanomethylamine, or 1-cyano-2-methoxyethyl amine;

R$^{5}$ is —OH —OTHP or —H; and

R$^{6}$ is —OH or —H provided that R$^{6}$ is not —OH when R$^{5}$ is —OH or —OTHP.

ESTRAMUSTINE (11)

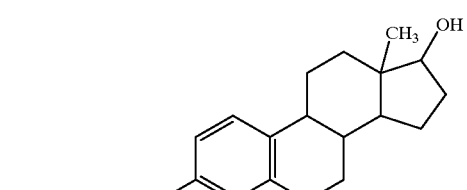

(11)

CYCLOPHOSPHAMIDE (12)

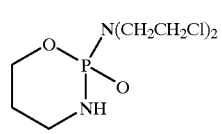

(12)

The most highly preferred drugs are the anthracycline antiobiotic agents of Formula (10), described previously. One skilled in the art understands that this structural formula includes compounds which are drugs, or are derivatives of drugs, which have acquired in the art different generic or trivial names. Table 1, which follows, represents a number of anthracycline drugs and their generic or trivial names and which are especially preferred for use in the present invention.

TABLE 1

(11)

| Compound | $R^a$ | $R^b$ | $R^c$ | $R_5$ | $R_6$ |
|---|---|---|---|---|---|
| daunorubicin[a] | $CH_3$ | $OCH_3$ | $NH_2$ | OH | H |
| doxorubicin[b] | $CH_2OH$ | $OCH_3$ | $NH_2$ | OH | H |
| detorubicin | $CH_2OCOCH(OC_2H_5)_2$ | $OCH_3$ | $NH_2$ | OH | H |
| carminomycin | $CH_3$ | OH | $NH_2$ | OH | H |
| idarubicin | $CH_3$ | H | $NH_2$ | OH | H |
| epirubicin | $CH_2OH$ | $OCH_3$ | $NH_2$ | OH | OH |
| esorubicin | $CH_2OH$ | $OCH_3$ | $NH_2$ | H | H |
| THP | $CH_2OH$ | $OCH_3$ | $NH_2$ | OTHP | H |
| AD-32 | $CH_2OCO(CH_2)_3CH_3$ | $OCH_3$ | $NHCOCF_3$ | OH | H |

[a]"daunomycin" is an alternative name for daunorubicin
[b]"adriamycin" is an alternative name for doxorubicin Of the compounds shown in Table 1, the most highly preferred cytotoxic agents are doxorubicin, vinblastine and desacetylvinblastine. Doxorubicin (also referred to herein as "DOX") is that anthracycline of Formula (10) in which $R_1$ is —$CH_2OH$, $R_3$ is —$OCH_3$, $R_4$ is —$NH_2$, $R_5$ is —OH, and $R_6$ is —H.

The oligopeptides, peptide subunits and peptide derivatives (also termed "peptides") incorporated in the conjugates utilized in the method of treatment of the present invention can be synthesized from their constituent amino acids by conventional peptide synthesis techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965; Bodansky et al., "Peptide Synthesis", Interscience Publishers, 1966; McOmie (ed.) "Protective Groups in Organic Chemistry", Plenum Press, 1973; Barany et al., "The Peptides: Analysis, Synthesis, Biology" 2, Chapter 1, Academic Press, 1980, and Stewart et al., "*Solid Phase Peptide Synthesis*", Second Edition, Pierce Chemical Company, 1984. The teachings of these works are hereby incorporated by reference.

The pharmaceutically acceptable salts of the compounds incorporated in the conjugates utilized in the method of treatment of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The conjugates utilized in the method of treatment of the instant invention which comprise the oligopeptide containing the PSA cleavage site and a cytotoxic agent may similarly be synthesized by techniques well known in the medicinal chemistry art. For example, a free amine moiety on the cytotoxic agent may be covalently attached to the oligopeptide at the carboxyl terminus such that an amide bond is formed. Similarly, an amide bond may be formed by covalently coupling an amine moiety of the oligopeptide and a carboxyl moiety of the cytotoxic agent. For these purposes a reagent such as 2-(1H-benzotriazol-1-yl)-1,3,3-tetramethyluronium hexafluorophosphate (known as HBTU) and 1-hyroxybenzotriazole hydrate (known as HOBT), dicyclohexyl-carbodiimide (DCC), N-ethyl-N-(3-dimethylaminopropyl)-carbodiimide (EDC), diphenylphosphorylazide (DPPA), benzotriazol-1-yl-oxy-tris-(dimethylamino)phosphonium hexafluorophosphate (BOP) and the like, used in combination or singularly, may be utilized.

Furthermore, the instant conjugate may be formed by a nonpeptidyl bond between the PSA cleavage site and a cytotoxic agent. For example, the cytotoxic agent may be covalently attached to the carboxyl terminus of the oligopeptide via a hydroxyl moiety on the cytotoxic agent, thereby forming an ester linkage. For this purpose a reagent such as a combination of HBTU and HOBT, a combination of BOP and imidazole, a combination of DCC and DMAP, and the like may be utilized. The carboxylic acid may also be activated by forming the nitrophenyl ester or the like and reacted in the presence of DBU (1,8-diazabicyclo[5,4,0] undec-7-ene.

The instant conjugate may also be formed by attachment of the oligopeptide to the cytotoxic agent via a linker unit. Such linker units include, for example, a biscarbonyl alkyl diradical whereby an amine moiety on the cytotoxic agent is connected with the linker unit to form an amide bond and the amino terminus of the oligopeptide is connected with the other end of the linker unit also forming an amide bond.

Conversely, a diaminoalkyl diradical linker unit, whereby a carbonyl moiety on the cyctotoxic agent is covalently attacted to one of the amines of the linker unit while the other amine of the linker unit is covalently attached to the C terminus of the oligopeptide, may also be useful. Other such linker units which are stable to the physiological environment when not in the presence of free PSA, but are cleavable upon the cleavage of the PSA proteolytic cleavage site, are also envisioned. Furthermore, linker units may be utilized that, upon cleavage of the PSA proteolytic cleavage site, remain attached to the cytotoxic agent but do not significantly decrease the cytotoxic activity of such a post-cleavage cytotoxic agent derivative when compared with an unmodified cytotoxic agent.

One skilled in the art understands that in the synthesis of conjugates utilized in the method of treatment of the invention, one may need to protect or block various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to *Protective Groups in Organic Chemistry*, McOmie, ed., Plenum Press, N.Y., N.Y. (1973); and, *Protective Groups in Organic Synthesis*, Greene, ed., John Wiley & Sons, N.Y., N.Y. (1981) for the teaching of protective groups which may be useful in the preparation of compounds of the present invention.

By way of example only, useful amino-protecting groups may include, for example, $C_1-C_{10}$ alkanoyl groups such as formyl, acetyl, dichloroacetyl, propionyl, hexanoyl, 3,3-diethylhexanoyl, γ-chlorobutryl, and the like; $C_1-C_{10}$ alkoxycarbonyl and $C_5-C_{15}$ aryloxycarbonyl groups such as tert-butoxycarbonyl, benzyloxycarbonyl, allyloxycarbonyl, 4-nitrobenzyloxycarbonyl, fluorenylmethyloxycarbonyl and cinnamoyloxycarbonyl; halo-$(C_1-C_{10})$-alkoxycarbonyl such as 2,2,2-trichloroethoxycarbonyl; and $C_1-C_{15}$ arylalkyl and alkenyl group such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1-C_{10}$ alkyl groups such as methyl, tert-butyl, decyl; halo-$C_1-C_{10}$ alkyl such as 2,2,2-trichloroethyl, and 2-iodoethyl; $C_5-C_{15}$ arylalkyl such as benzyl, 4-methoxybenzyl, 4-nitrobenzyl, triphenylmethyl, diphenylmethyl; $C_1-C_{10}$ alkanoyloxymethyl such as acetoxymethyl, propionoxymethyl and the like; and groups such as phenacyl, 4-halophenacyl, allyl, dimethylallyl, tri-$(C_1-C_3$ alkyl)silyl, such as trimethylsilyl, β-p-toluenesulfonylethyl, β-p-nitrophenyl-thioethyl, 2,4,6-trimethylbenzyl, β-methylthioethyl, phthalimidomethyl, 2,4-dinitrophenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

With respect to the preferred embodiment of the instant method of treatment in which an oligopeptide is combined with the anthracycline antibiotic doxorubicin, the following Reaction Schemes illustrate the synthesis of the conjugates of the instant invention.

REACTION SCHEME I

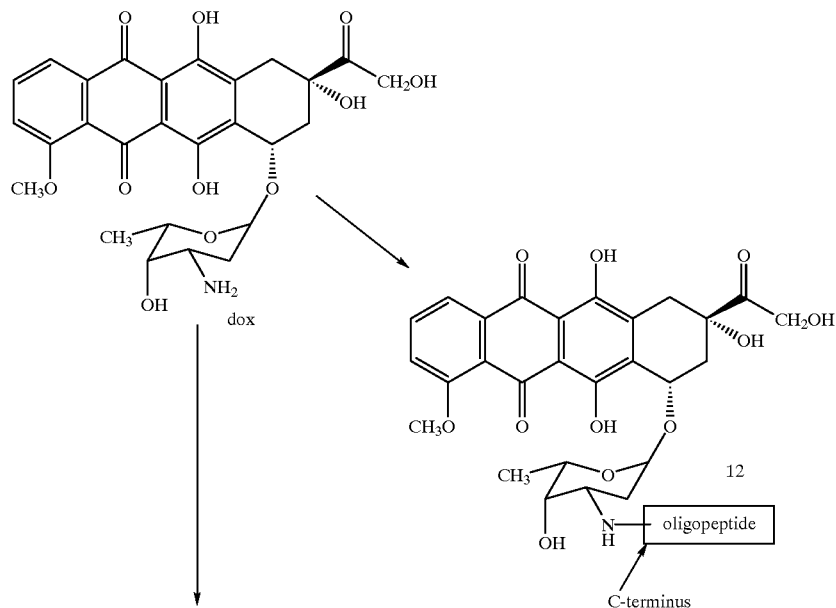

-continued
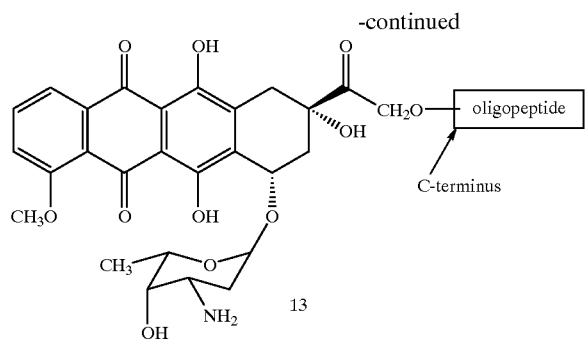
13
REACTION SCHEME II
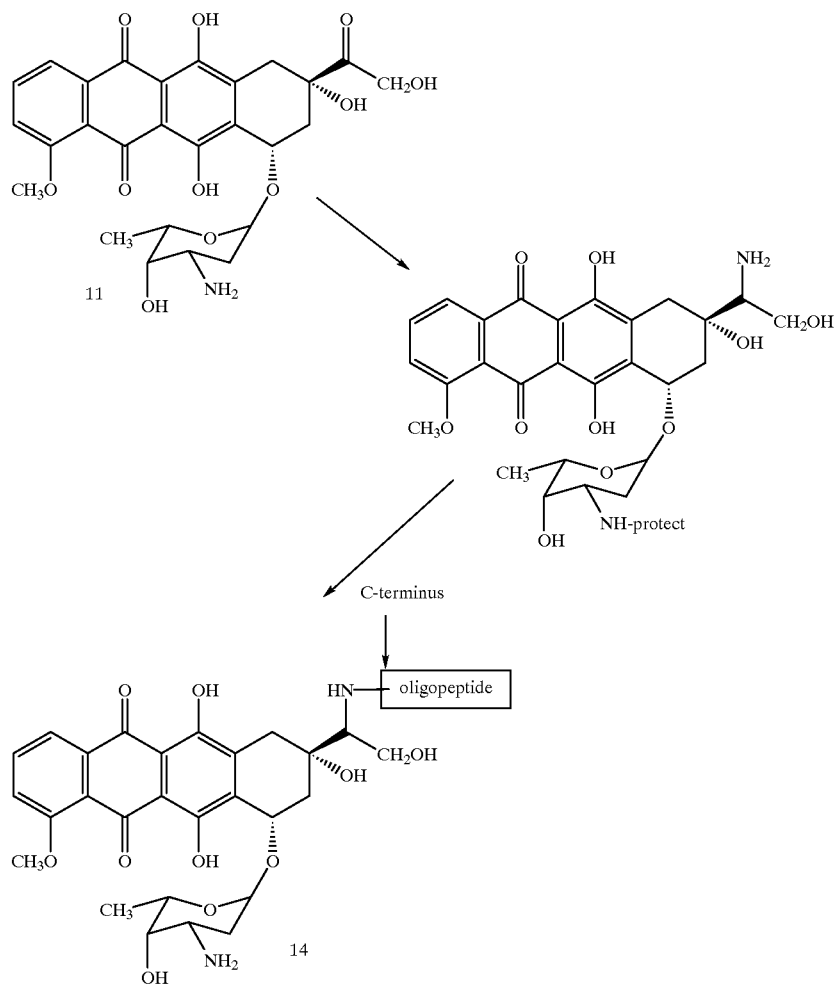

REACTION SCHEME III
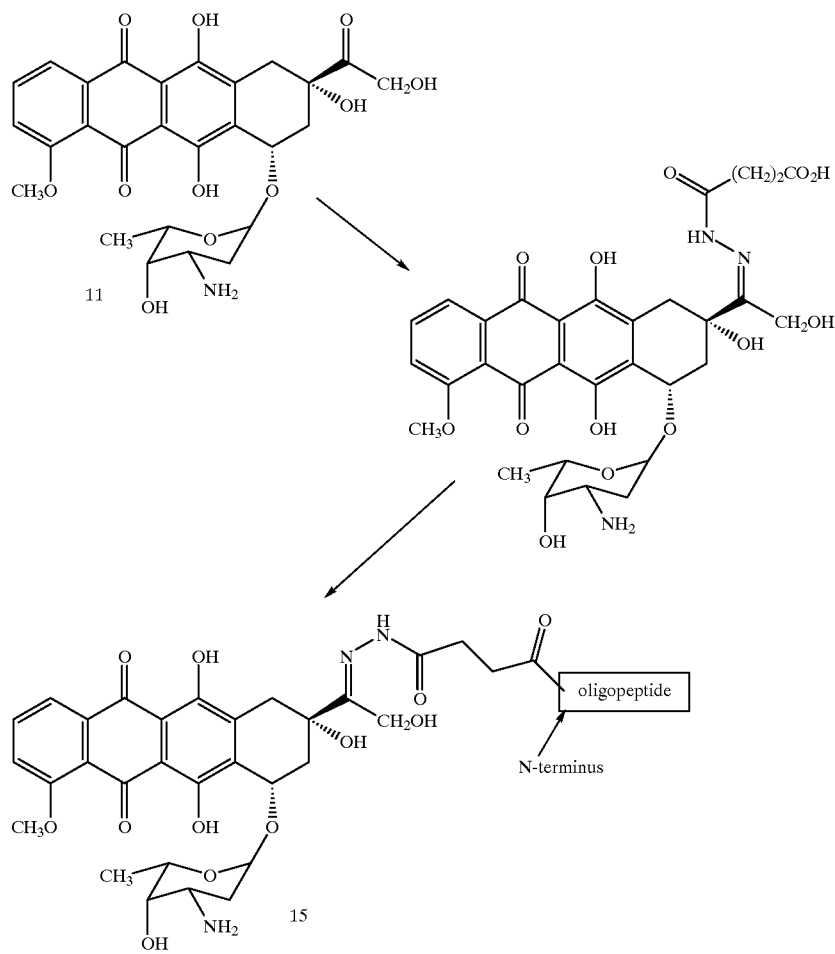
REACTION SCHEME IV
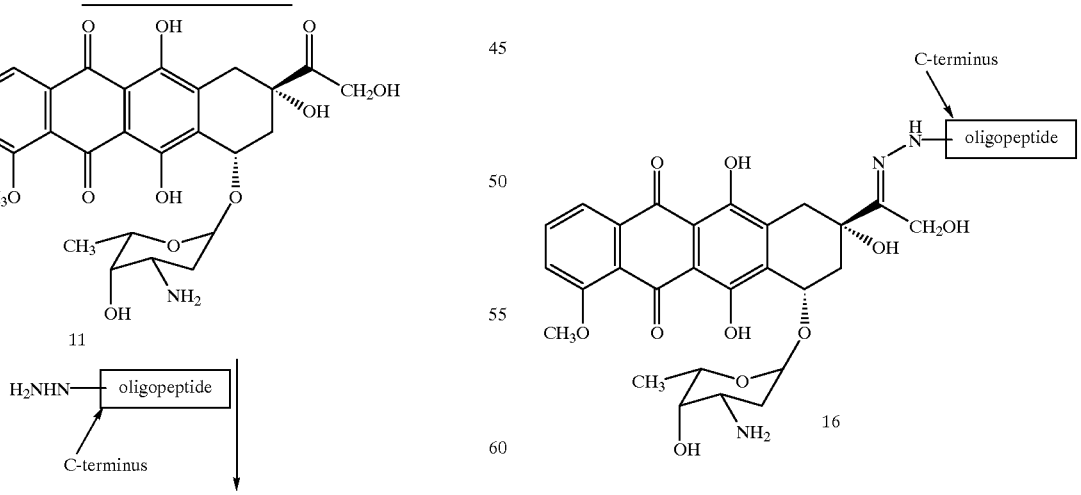

REACTION SCHEME V

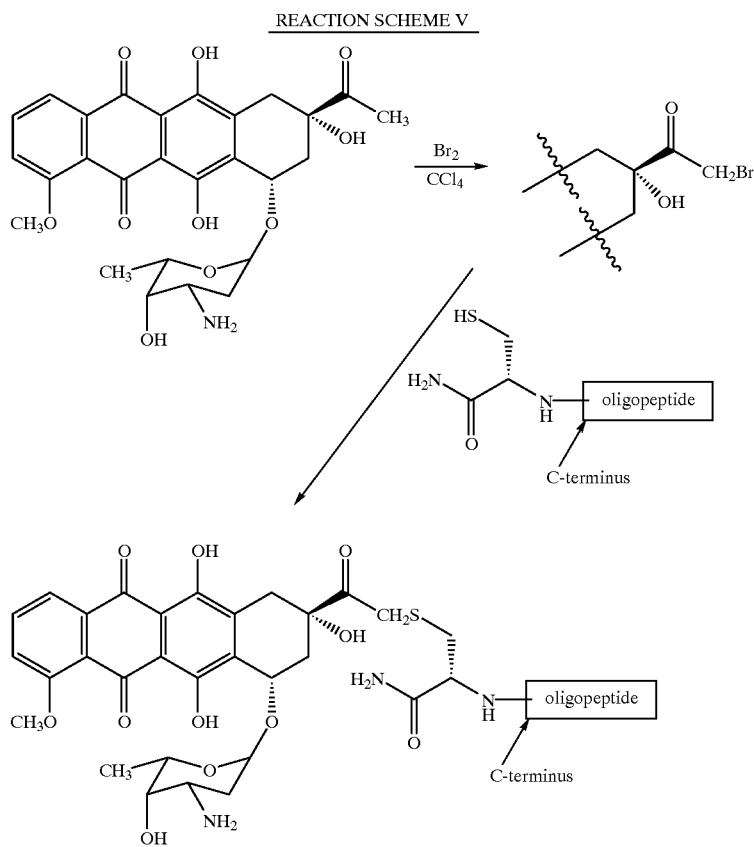

Reaction Scheme VI illustrates preparation of conjugates utilized in the instant method of treatment wherein the oligopeptides are combined with the vinca alkaloid cytotoxic agent vinblastine. Attachment of the N-terminus of the oligopeptide to vinblastine is illustrated (S. P. Kandukuri et al. J. Med. Chem. 28:1079–1088 (1985)).

Reaction Scheme VII illustrates preparation of conjugates utilized in the instant method of treatment wherein the oligopeptides are combined with the vinca alkaloid cytotoxic agent vinblastine wherein the attachment of vinblastine is at the C-terminus of the oligopeptide. The use of the 1,3-diaminopropane linker is illustrative only; other spacer units between the carbonyl of vinblastine and the C-terminus of the oligopeptide are also envisioned. Furthermore, Scheme VII illustrates a synthesis of conjugates wherein the C-4-position hydroxy moiety is reacetylated following the addition of the linker unit. Applicants have discovered that the desacetyl vinblastine conjugate is also efficacious and may be prepared by eliminating the steps shown in Reaction Scheme VII of protecting the primary amine of the linker and reacting the intermediate with acetic anhydride, followed by deprotection of the amine. Conjugation of the oligopeptide at other positions and functional groups of vinblastine may be readily accomplished by one of ordinary skill in the art and is also expected to provide compounds useful in the treatment of benign prostatic hyperplasia.

It is also understood that conjugates may be prepared wherein the N-terminus of the oligopeptide utilized in the instant method of treatment is combined with one cytotoxic agent, such as vinblastine, while the C-terminus is simultaneously attached to another cytotoxic agent, which is the same or different cytotoxic agent, such as doxorubicin. Reaction Scheme VIII illustrates the synthesis of such a polycytotoxic agent conjugate. Such a polycytotoxic conjugate may offer advantages over a conjugate containing only one cytotoxic agent.

REACTION SCHEME VI

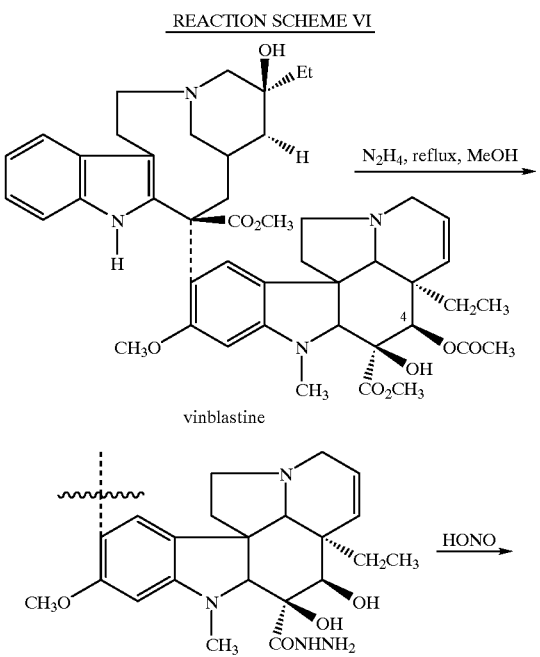

25
-continued
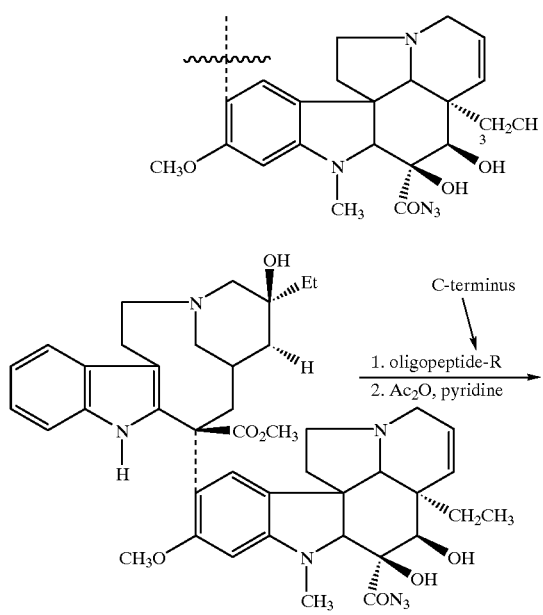
26
-continued
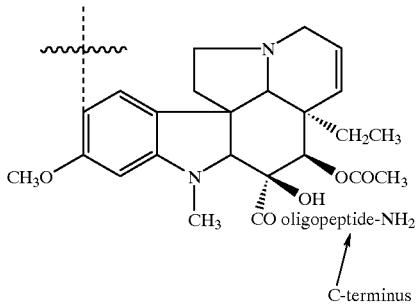
where R is —NH₂, —O-alkyl and the like
REACTION SCHEME VII
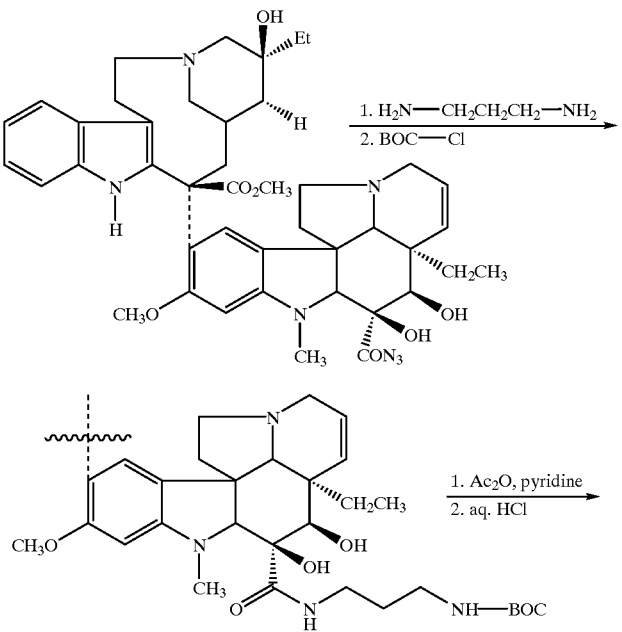

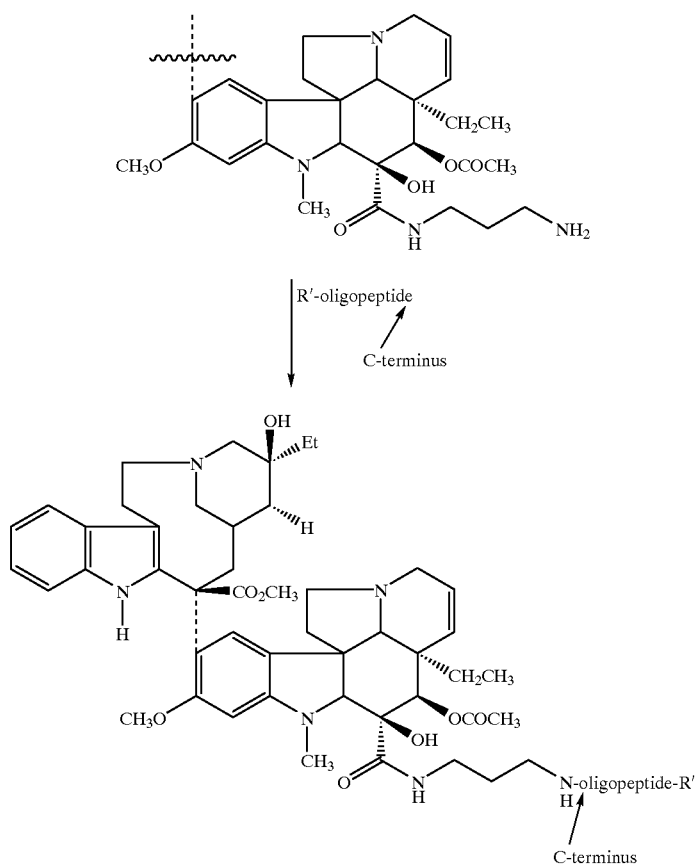
wherein R' is acetyl, alkyl, hydrogen or the like
REACTION SCHEME VIII
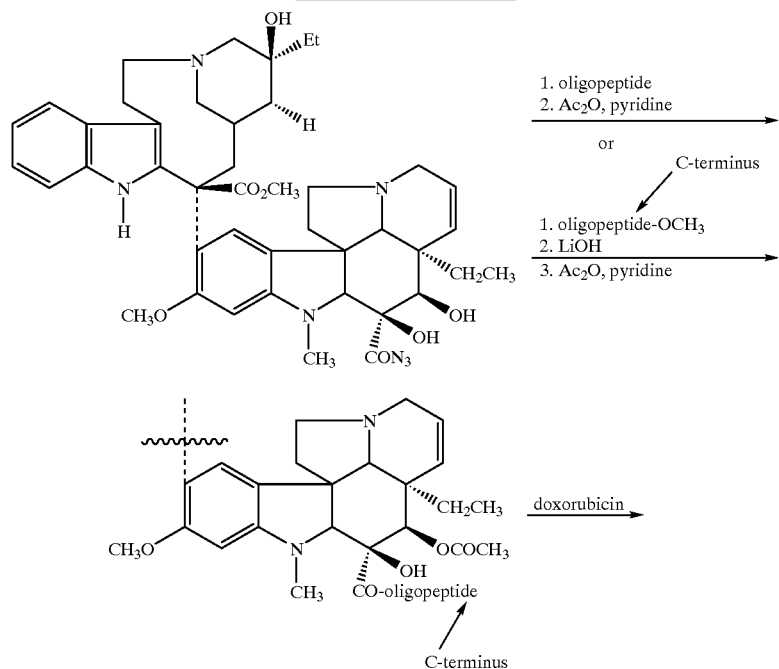

-continued

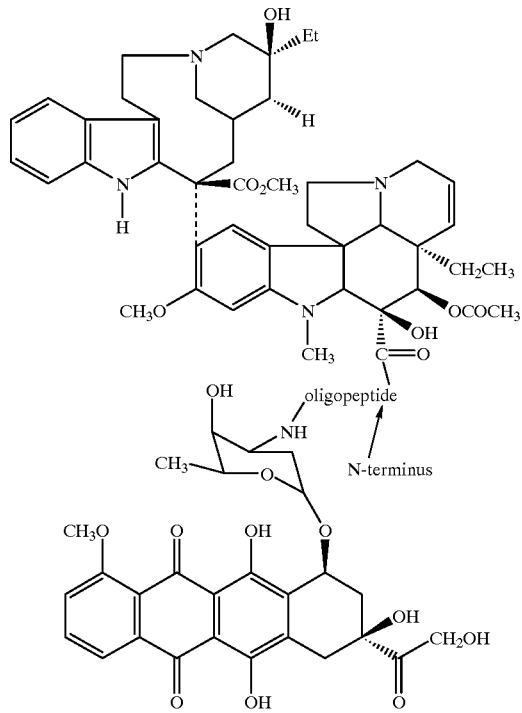

The oligopeptide-cytotoxic agent conjugate utilized in the method of treatment of the instant invention wherein the cytotoxic agent is the preferred cytotoxic agent doxorubicin may be described by the general formula I below:

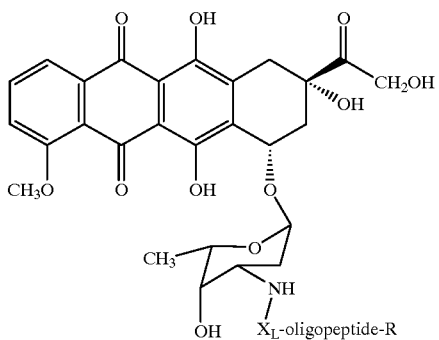

wherein:
oligopeptide is an oligopeptide which is specifically recognized by the free prostate specific antigen (PSA) and is capable of being proteolytically cleaved by the enzymatic activity of the free prostate specific antigen;
$X_L$ is absent or is an amino acid selected from:
  a) phenylalanine,
  b) leucine,
  c) valine,
  d) isoleucine,
  e) (2-naphthyl)alanine,
  f) cyclohexylalanine,
  g) diphenylalanine,
  h) norvaline,
  i) norleucine, and
  j) 1,2,3,4-tetrahydroiso quinoline-3-carboxylic acid;

R is hydrogen or —(C=O)$R^1$; and
$R^1$ is $C_1$–$C_6$-alkyl or aryl,
or the pharmaceutically acceptable salt thereof.

In a preferred embodiment of the instant method of treatment of BPH:
oligopeptide is an oligomer that comprises an amino acid sequence selected from:
  a) AsnLysIleSerTyrGln|Ser (SEQ.ID.NO.: 13),
  b) LysIleSerTyrGln|Ser (SEQ.ID.NO.: 14),
  c) GlyGluAsnGlyValGlnLysAspValSerGlnXaaSerIle Tyr|SerGlnThrGlu (SEQ.ID.NO.: 15),
  d) GlyLysGlyIleSerSerGlnTyr|SerAsnThrGluGluArgLeu (SEQ.ID.NO.: 2),
  e) AsnLysIleSerTyrTyr|Ser (SEQ.ID.NO.: 127),
  f) AsnLysAlaSerTyrGln|Ser (SEQ.ID.NO.: 128),
  g) SerTyrGln|SerSer (SEQ.ID.NO.: 129),
  h) LysTyrGln|SerSer (SEQ.ID.NO.: 140);
  i) hArgTyrGln|SerSer (SEQ.ID.NO.: 141);
  j) hArgChaGln|SerSer (SEQ.ID.NO.: 185); and
  k) TyrGln|SerSer (SEQ.ID.NO.: 186);
wherein Xaa is any natural amino acid;

$X_L$ is absent or is an amino acid selected from:
  a) leucine,
  b) isoleucine,
  c) norleucine, and
  d) valine; and R is acetyl, pivaloyl or benzoyl,
or the pharmaceutically acceptable salt thereof.

The following compounds are specific examples of the oligopeptide-cytotoxic agent conjugate utilized in the method of treatment of the instant invention:

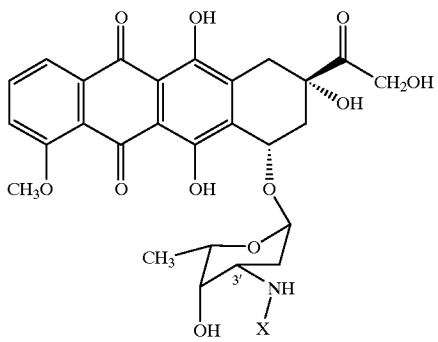

wherein X is:
AsnLysIleSerTyrGlnSer- (SEQ.ID.NO.: 13),
AsnLysIleSerTyrGlnSerSer- (SEQ.ID.NO.: 16),
AsnLysIleSerTyrGlnSerSer- (SEQ.ID.NO.: 17),
AsnLysIleSerTyrGlnSerSerThr- (SEQ.ID.NO.: 10),
AsnLysIleSerTyrGlnSerSerThrGlu- (SEQ.ID.NO.: 3), AlaAsnLysIleSerTyrGlnSerSerThrGlu- (SEQ.ID.NO.: 11),
/
N-terminus Ac-AlaAsnLysIleSerTyrGlnSerSerSerThr- (SEQ.ID.NO.: 117),
Ac-AlaAsnLysIleSerTyrGlnSerSerSerThrLeu- (SEQ.ID.NO.: 70),
Ac-AlaAsnLysAlaSerTyrGlnSerAlaSerThrLeu- (SEQ.ID.NO.: 118),
Ac-AlaAsnLysAlaSerTyrGlnSerAlaSerLeu- (SEQ.ID.NO.: 119),
Ac-AlaAsnLysAlaSerTyrGlnSerSerSerLeu- (SEQ.ID.NO.: 120),
Ac-AlaAsnLysAlaSerTyrGlnSerSerLeu- (SEQ.ID.NO.: 121).
Ac-SerTyrGlnSerSerSerLeu- (SEQ.ID.NO.: 144),
Ac-hArgTyrGlnSerSerSerLeu- (SEQ.ID.NO.: 145).
Ac-LysTyrGlnSerSerSerLeu- (SEQ.ID.NO.: 124), or (Compound 4)

Ac-LysTyrGlnSerSerNle- (SEQ.ID.NO.: 146).
/
N-terminus or the pharmaceutically acceptable salt thereof.
Further examples of conjugates of an oligopeptide and doxorubicin wherein the N-terminus of the oligopeptide is acylated and the C-terminus of the oligopeptide is attached to the doxorubicin at the 3'-amine are as follows:
Ac-hArgTyrGln-SerSerPro-dox(3') (SEQ.ID.NO.: 151)
Ac-hArgTyrGln-SerPro-dox(3') (SEQ.ID.NO.: 177)
Ac-hArgTyrGln-SerSerSerNle-dox(3') (SEQ.ID.NO.: 154)
Ac-AmfTyrGln-SerSerSerNle-dox(3') (SEQ.ID.NO.: 155)
$H_2NCO$-hArgTyrGln-SerSerSerLeu-dox(3') (SEQ.ID.NO.: 156)
Ac-LysTyrGln-SerSerNle-dox(3') (SEQ.ID.NO.: 146)
Ac-LysTyrGln-SerLysNle-dox(3') (SEQ.ID.NO.: 178)
Ac(cis-p-$NH_2$Cha)TyrGlnSerSerNledox(3') (SEQ.ID.NO.: 161)
Ac-AlaAspLysAla(hArg)TyrGln-SerSerLeu-dox(3') (SEQ.ID.NO.: 160)
Ac-hArgTyrGln-SerAsn-dox(3') (SEQ.ID.NO.: 153)
Ac-hArgTyrGln-SerSerHis-dox(3') (SEQ.ID.NO.: 152)
Ac-(imidazolyl)LysTyrGln-SerSerLeu-dox(3') (SEQ.ID.NO.: 159)
Ac-(imidazolyl)LysTyrGlnSerSerSerNle-dox(3') (SEQ.ID.NO.: 162)
Ac-hArg(Cha)Gln-SerSerSerNle-dox(3') (SEQ.ID.NO.: 163)
Ac-hArg($Me_2PO_3$Tyr)Gln-SerSerSerNle-dox(3') (SEQ.ID.NO.: 167)
Ac-hArgTyrGln-SerSerSerhArg-dox(3') (SEQ.ID.NO.: 164)
Ac-hArg(3-Iodo-Tyr)Gln-SerSerSerNle-dox(3') (SEQ.ID.NO.: 166)
Ac-hArg(O-Me-Tyr)Gln-SerSerSerNle-dox(3') (SEQ.ID.NO.: 169)
Ac-hArg(p-$NH_2$-Phe)Gln-SerSerSerNle-dox(3') (SEQ.ID.NO.: 179)
Ac-hArg(Cha)Gln-SerSerNle-dox(3') (SEQ.ID.NO.: 174)
Ac-hArg(Cha)Gln-SerProNle-dox(3') (SEQ.ID.NO.: 175)
Ac(imidazolyl)Lys(Cha)GlnSerSerSerNle-dox(3') (SEQ.ID.NO.: 172)
Ac-hArg(7-HO-TIC)Gln-SerSerSerNle-dox(3') (SEQ.ID.NO.: 180)
Ac-hArg(3-Fluoro)TyrGlnSerSerSerNle-dox(3') (SEQ.ID.NO.: 176)
Ac-(ornithine)TyrGln-SerSerSerNle-dox(3') (SEQ.ID.NO.: 181)
Ac-LysAlaAlaSerSerSerLeu-dox(3') (SEQ.ID.NO.: 183)
Ac-hArgh(Cha)Gln-SerSerNle-dox(3') (SEQ.ID.NO.: 149)
Ac-AlaArgLysAlaSerTyrGln-SerLeu-dox(3') (SEQ.ID.NO.: 193) and
Ac-(Orn)TyrGln-SerSerSerLeu-dox(3') (SEQ.ID.NO.: 194)
or the pharmaceutically acceptable salt thereof.

The oligopeptide-cytotoxic agent conjugate utilized in the method of treatment of the instant invention wherein the cytotoxic agent is the preferred cytotoxic agent vinblastine or desacetylvinblastine may be described by the general formula I below:

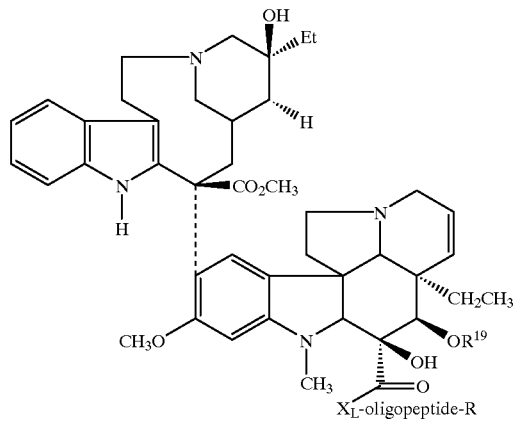

wherein:
oligopeptide is an oligopeptide which is specifically recognized by the free prostate specific antigen (PSA) and is capable of being proteolytically cleaved by the enzymatic activity of the free prostate specific antigen;
$X_L$ is absent or is an amino acid selected from:
a) phenylalanine,
b) leucine,
c) valine, d) isoleucine,
e) (2-naphthyl)alanine,
f) cyclohexylalanine,
g) diphenylalanine,
h) norvaline, and
i) norleucine, and
j) 1,2,3,4-tetrahydroisoquinoline-3-carboxylic acid; or $X_L$ is —NH—$(CH_2)_n$—NH—

R is hydrogen or —(C=O)$R^1$;

$R^1$ is $C_1$–$C_6$-alkyl or aryl;

$R^{19}$ is hydrogen or acetyl; and n is 1, 2, 3, 4 or 5, or the pharmaceutically acceptable salt thereof.

The following compounds are specific examples of the oligopeptide-desacetylvinblastine conjugate utilized in the method of treatment of the instant invention:

Compound 14

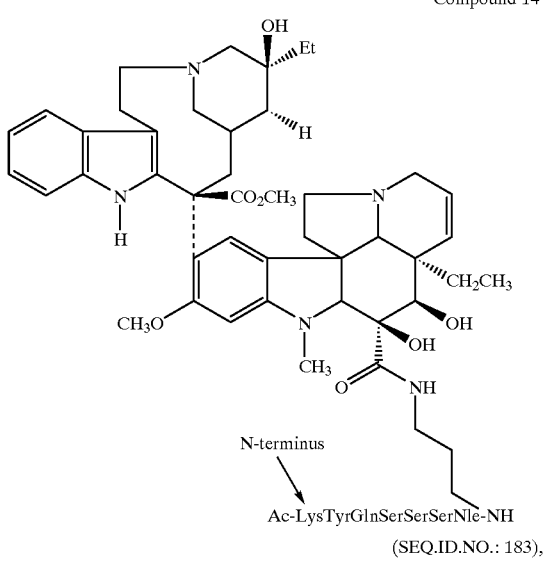

Ac-LysTyrGlnSerSerSerNle-NH
(SEQ.ID.NO.: 183),

Compound 5

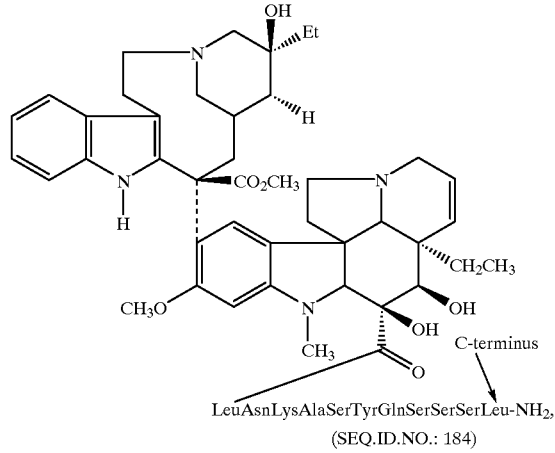

LeuAsnLysAlaSerTyrGlnSerSerSerLeu-NH$_2$,
(SEQ.ID.NO.: 184)

or the pharmaceutically acceptable salt thereof.

The following compounds is a specific example of the polycytotoxic agent conjugates utilized in the method of treatment of the instant invention:

Compound 10

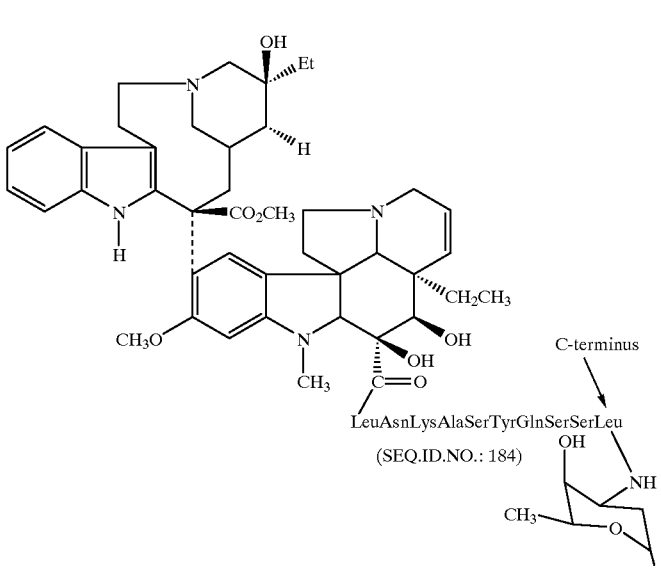

LeuAsnLysAlaSerTyrGlnSerSerSerLeu
(SEQ.ID.NO.: 184)

-continued

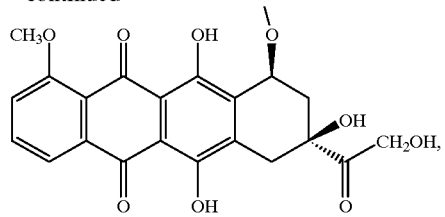

or the pharmaceutically acceptable salt thereof.

It is well known in the art, and understood in the instant invention, that peptidyl therapeutic agents such as the oligopeptide-cytotoxic agent conjugates preferably have the terminal amino moiety of any oligopeptide substituent protected with a suitable protecting group, such as acetyl, benzoyl, pivaloyl and the like. Such protection of the terminal amino group reduces or eliminates the enzymatic degradation of such peptidyl therapeutic agents by the action of exogenous amino peptidases which are present in the blood plasma of warm blooded animals.

The oligopeptide-cytotoxic agent conjugates utilized in the method of treatment of the instant invention are administered to the patient in the form of a pharmaceutical composition which comprises a conjugate of Formula (I) and a pharmaceutically acceptable carrier, excipient or diluent therefor. As used, "pharmaceutically acceptable" refers to those agents which are useful in the treatment or diagnosis of a warm-blooded animal including, for example, a human, equine, procine, bovine, murine, canine, feline, or other mammal, as well as an avian or other warm-blooded animal. The preferred mode of administration is parenterally, particularly by the intravenous, intramuscular, subcutaneous, intraperitoneal, or intralymphatic route. Such formulations can be prepared using carriers, diluents or excipients familiar to one skilled in the art. In this regard, See, e.g. *Remington's Pharmaceutical Sciences*, 16th ed., 1980, Mack Publishing Company, edited by Osol et al. Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The compositions may contain preservatives such as phenethyl alcohol, methyl and propyl parabens, thimerosal, and the like. If desired, the composition can include about 0.05 to about 0.20 percent by weight of an antioxidant such as sodium metabisulfite or sodium bisulfite.

For intravenous administration, the composition preferably will be prepared so that the amount administered to the patient will be from about 0.01 to about 1 g of the conjugate. Preferably, the amount administered will be in the range of about 0.2 g to about 1 g of the conjugate. The conjugates of the invention are effective over a wide dosage range depending on factors such as the disease state to be treated or the biological effect to be modified, the manner in which the conjugate is administered, the age, weight and condition of the patient as well as other factors to be determined by the treating physician. Thus, the amount administered to any given patient must be determined on an individual basis.

One skilled in the art will appreciate that although specific reagents and reaction conditions are outlined in the following examples, modification can be made which are meant to be encompassed by the spirit and scope of the invention. The following preparations and examples, therefore, are provided to further illustrate the invention, and are not limiting.

EXAMPLES

Example 1

Identification of the Semenogelin PSA Mediated Cleavage Site:

Liquefaction of the seminal gel parallels proteolytic fragmentation of semenogelin I [Lilja, H., Laurell, C. B., (1984) Scand. J. Clin. Lab. Inves. 44, 447–452]. It is believed that the proteolytic fragmentation of semenogelin is mainly due to the proteolytic activity of prostate-specific antigen [Lilja, H., (1985) J. Clin. Invest. 76, 1899–1903]. Utilizing the published sequence of semenogelin I [Lilja, H., Abrahamsson, P. A., Lundwall, A., (1989) J. of Biol. Chem. 264, 1894–1900] (FIG. 1) we designed polymerase chain reaction primers to clone the semenogelin cDNA from a commercially available prostatic cDNA library (Clone-tech, Palo Alto, Calif.). The purified semenogelin cDNA was placed into the bacterial expression vector pTAC [Linemeyer, D. L., Kelly, L. J., Minke, J. G., Gimenez-Gallego, G., DeSalvo, J. and Thomas, K. A., (1987) Bio/Technology 5, 960–965]. The semenogelin cDNA was designed so that a tubulin epitope was placed at the carboxyl end of semenogelin protein. The bacterially expressed semenogelin protein was purified on an anti-tubulin antibody column. The purified semenogelin I protein was mixed with commercially prepared prostate-specific antigen (PSA) (York Biologicals International, Stony Brook, N.Y.) in an 100 to 1 molar ratio (semenogelin I/PSA) in 12 mM Tris pH 8.0, 25 mM NaCl, 0.5 mM $CaCl_2$, and incubated for various times. The digest was fractionated by polyacrylarnide gel electrophoresis and transferred by electrophoresis to ProBlott filter paper (Applied Biosystems, Inc., Foster City, Calif.) in CAPS buffer [Matsudaira, P., (1987) J. Biol. Chem. 252, 10035–10038]. The ProBlott filter paper was stained with coomassie blue to identify the novel PSA generated semenogelin I protein fragments.

The novel fragments were cut out of the filter with a scalpel and submitted for sequence determination. After the proteolytic fragments were identified by variable time digestion, a 10 minute digestion reaction was performed. The affinity of PSA for the 5 potential cleavage sites in semenogelin I was determined to be as follows: site 349/350>site 375/376>site 289/290=site 315/316>site 159/160. The relative affinities were derived from the comassie blue staining intensity of each PSA generated peptide fragment. These intensities had approximate ratios of 3:1:0.6:0.3.

Example 2

Preparation of Oligopeptides which Comprise the PSA Mediated Cleavage Site:

Oligopeptides were prepared by solid-phase synthesis, using a double coupling protocol for the introduction of amino acids on the Applied Biosystems model 430A automated peptide synthesizer. Deprotection and removal of the oligopeptide from the resin support were achieved by treatment with liquid hydrofluoric acid. The oligopeptides were purified by preparative high pressure liquid chromatography on reverse phase C18 silica columns using an aqueous 0.1% trifluoroacetic acid/acetonitrile gradient. Identity and homogeneity of the oligopeptides were confirmed by amino acid composition analysis, high pressure liquid chromatography, and fast atom bombardment mass spectral analysis. The oligopeptides that were prepared by this method are shown in FIG. 2.

Example 3
Assessment of the Recognition of Oligopeptides by Free PSA:

The oligopeptides prepared as described in Example 2 were individually dissolved in PSA digestion buffer (12 mM tris(hydroxymethyl)-aminomethane pH8.0, 25 mM NaCl, 0.5 mM $CaCl_2$) and the solution added to PSA at a molar ration of 100 to 1. Alternatively, the PSA digestion buffer utilized is 50 mM tris(hydroxymethyl)-aminomethane pH7.4, 140 mM NaCl. The reaction is quenched after various reaction times by the addition of trifluoroacetic acid (TFA) to a final 1% (volume/volume). Alternatively the reaction is quenched with 10 nM $ZnCl_2$. The quenched reaction was analyzed by HPLC on a reversed-phase C18 column using an aqueous 0.1% TFA/acetonitrile gradient. The results of the assessment are shown in FIG. 2. Other oligopeptides prepared as described in Example 2 were tested in the same assay wherein the reaction was quenched at 4 hours. Those results of the assessment are shown in FIG. 3. The removal of an asparagine residue from the amino terminus of the oligopeptide results in a significant loss of PSA mediated peptide hydrolysis, while the presence of a glutamic acid residue at the carboxyl end of the peptide appears not to be essential to recognition by PSA.

Example 4
Preparation of Non-cleavable Oligopeptide-Doxorubicin Conjugates:

The derivatives of doxorubicin shown in Table 3 were prepared using the following general reaction: To a mixture of doxorubicin (Sigma) and the corresponding peptide (prepared by solid phase synthesis or commercially available (Sigma)) in DMSO was added HBTU and HOBT along with diisopropylethylamine and the reaction mixture was stirred overnight. The crude reaction mixture was purified directly by preparative HPLC on a reversed-phase C-18 column using a 0.1% trifluoroacetic acid (TFA) in acetonitrile/0.1% TFA in water gradient.

TABLE 3

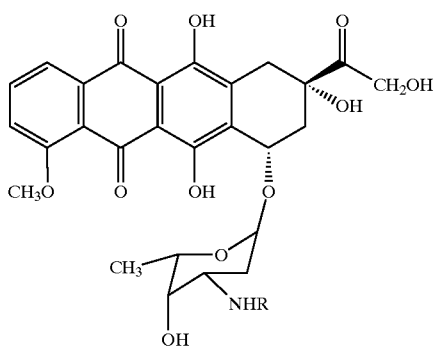

| Compound | R | MS (parent ion) |
|---|---|---|
| 12a | H-Ala- | 615 |
| 12b | N-Ac-Ala- | 657 |
| 12c | N-Ac-Ala-Ala-Ala- | 799.5 |
| 12d | N-Ac-Ala-Gly-Pro-Thr-Gly-Ala-Ser-Ala- (SEQ. ID. NO.: 12) | 1199 |

Example 5
In vitro Assay of Cytotoxicity of Peptidyl Derivatives of Doxorubicin:

The cytotoxicities of the non-cleaveable oligopeptide-doxorubicin conjugates, prepared as described in Example 4, against a line of cells which is known to be killed by unmodified doxorubicin were assessed with an Alamar Blue assay. Specifically, cell cultures of LNCaP prostate tumor cells, which are a human metastatic prostate adenocarcinoma isolated from a needle biopsy of a lymph node (LNCaP.FGC: American Type Culture Collection, ATCC CRL 1740), or DuPRO cells in 96 well plates were diluted with medium containing various concentrations of a given conjugate (final plate well volume of 200 $\mu$l). The cells were incubated for 3 days at 37° C. and then 20 $\mu$l of Alamar Blue was added to the assay well. The cells were further incubated and the assay plates were read on a EL-310 ELISA reader at the dual wavelengths of 570 and 600 nm at 4 and 7 hours after addition of Alamar Blue. Relative percentage viability at the various concentration of conjugate tested was then calculated versus control (no conjugate) cultures. Cytotoxicities of unmodified doxorubicin and unmodified oligopeptide were also assessed. FIG. 3 shows the cytotoxicity data for a representative compound (Compound 12d).

Example 6
Assessment of Enzymatically Active PSA from LNCaP Cells

Enzymatic activity was demonstrated by incubating LNCaP serum free media (concentrated approximately 200 fold) with recombinant Sememogelin I protein. Approximately 0.5 $\mu$g of immunologically reactive PSA in concentrated conditioned media [determined by HYBRIDTECH (Tandem E) elisa] was mixed with approximately 3 $\mu$g of recombinant Semenogelin I and incubated for 4 hours at 37° C. At the end of the incubation, the digest mixture was analyzed by Western blot procedures. The results show that purified PSA from semen and PSA from LNCaP conditioned media generate identical proteolytic maps of the recombinant Semenogelin I protein. Thus, LNCaP cells produce enzymatically active PSA. LNCaP are tumorigenic in nude mice and produce detectable levels of circulating PSA.

Example 7
Preparation of Cleavable Oligopeptide-Doxorubicin Conjugates:

The derivatives of doxorubicin wherein an oligopeptide which is proteolytically cleaved by free PSA is covalently attached to the amine of the sugar moiety of the doxorubicin were prepared using the following general reaction: To a mixture of doxorubicin (Sigma) and the corresponding peptide (prepared by solid phase synthesis as described in Example 2) in DMSO was added HBTU and HOBT along with diisopropylethylamine and the reaction mixture stirred overnight. The crude reaction mixture was purified directly by preparative HPLC on a reversed-phase C-18 column using a 0.1% trifluoroacetic acid (TFA) in acetonitrile/0.1% TFA in water gradient. When reactive amine moieties were present on the peptide, such a functionality was typically protected as the fluorenylmethyloxycarbonyl adduct, which was removed by treatment with a secondary amine, such as piperidine and the like, subsequent to conjugation with doxirubicin. The instant conjugates have a structure of the general formula

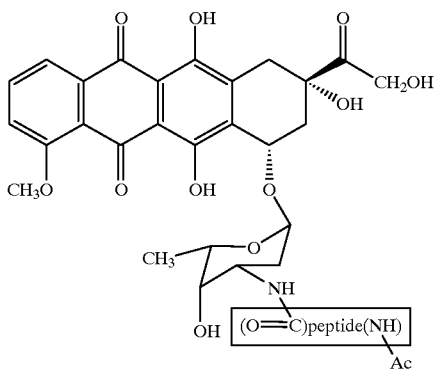

and may be represented by the phrase "Ac-peptide-DOX (3')." Conjugates which were prepared by the above general method or by the synthetic route described in Example 8, but utilizing the appropriate starting amino acid residues which are readily available commercially or by synthetic techniques well known in the art, are listed in Tables 5, 5a and 7 in FIGS. 5, 5A and 7.

Example 8
Ac-Lys-Tyr-Gln-Ser-Ser-Ser-Leu-Dox•Acetate

Step A: Ac-Lys(Fmoc)-Gln-Ser(Bzl)-Ser(Bzl)-Ser(Bzl)-Leu-PAM Resin (1).

Starting with 0.5 mmol (0.67 g) Boc-Leu-PAM resin, the protected peptide was synthesized on a 430A ABI peptide synthesizer. The protocol used a 4 fold excess (2 mmol) of each of the following protected amino acids: Boc-Ser (OBzl), Boc-Gln, Boc-Tyr(BrZ), Boc-Lys(Fmoc). Coupling was achieved using DCC and HOBT activation in methyl-2-pyrrolidinone. Acetic acid was used for the introduction of the N terminal acetyl group. Removal of the Boc group was performed using 50% TFA in methylene chloride and the TFA salt neutralized with diisopropylethylamine. At the completion of the synthesis, the peptide resin was dried to yield 1.3 g of (1).

Step B: Ac-Lys(Fmoc)-Tyr-Gln-Ser-Ser-Ser-Leu-OH (2)

The protected peptide resin (1), 1.3 g, was treated with HF (20 ml) for 2 hrs at 0° C. in the presence of anisole (2 ml). After evaporation of the HF, the residue was washed with ether, filtered and extracted with DMF. The DMF filtrate (75 ml) was concentrated to dryness and triturated with $H_2O$. The insoluble product (2) was filtered and dried (0.46 g).

Step C: Ac-Lys(Fmoc)-Tyr-Gln-Ser-Ser-Ser-Leu-Dox (3)

The above prepared intermediate (2), 0.46 g, (0.43 mmol) was dissolved in DMF (15 ml) and doxorubicin hydrochloride, 125 mg (0.215 mmol), added followed by 60 μl of triethylamine (0.430 mmol). The stirred solution was cooled (0° C.) and 92 μl of diphenylphosphoryl azide (0.43 mmol) added. After 5 minutes, an additional 92 μl of DPPA was added and the pH adjusted to ~7.5 (pH paper) with TEA. After 1 hour, an additional 92 μl of DPPA was added, pH adjusted to ~7.5, and the reaction stirred at 0°–5° C. overnight. After 18 hours, the reaction (found to be complete by analytical HPLC) was concentrated to an oil (3).

Step D: Ac-Lys-Gln-Tyr-Ser-Ser-Ser-Leu-Dox (4).

The above product (3) was dissolved in DMF (20 ml), cooled (0° C.) and 10 ml of piperidine added. The solution was concentrated to dryness and purified by preparative HPLC. Buffer A=15% acetic acid-$H_2O$; B=15% acetic acid-methanol. The crude product was dissolved in 300 ml of 10% B/90% A buffer, filtered and purified on a C-18 reverse phase HPLC radial compression column (Waters, Delta-Pak 15 μm, 300 Å). A step gradient of 10% B to 60% B was used at a flow rate of 75 ml/min (uv=260 nm). Homogeneous product fractions were pooled, concentrated and freeze-dried from $H_2O$ to yield 125 mg of purified product (4).

Example 9
Deacetylvinblastinyl-Leu-Asn-Lys-Ala-Ser-Try-Gln-Ser-Ser-Ser-Leu-$NH_2$•Acetate (5) (SEQ.ID.NO. 184)

Step A: $NH_2$-Leu-Asn-Lys(Fmoc)-Ala-Ser-Tyr-Gln-Ser-Ser-Ser-Leu-Amide (6)

Starting with 0.5 mmol of p-methylbenzhydrylamine resin (MBHA), the protected peptide, $NH_2$-Leu-Asn-Lys (Fmoc)-Ala-Ser(OBzl)-Tyr(BrZ)-Gln-Ser(OBzl)-Ser (OBzl)-Ser(OBzl)-Leu-MBHA, intermediate was synthesized on a 430A ABI peptide synthesizer. The protocol used a 4 fold excess (2 mmol) of each of the following protected amino acids: Boc-Leu, Boc-Asn, Boc-Lys (Fmoc), Boc-Ala, Boc-Ser(OBzl), Boc-Tyr(BrZ), Boc-Gln. Coupling was achieved using DCC and HOBT activation in N-methyl-2-pyrrolidinone (NMP).

Removal of the Boc group was performed using 50% TFA in methylene chloride and the TFA salt neutralized with diisopropylethylamine. The dried protected peptide resin (1.80 g) was treated with HF (20 ml) for 2 hrs at 0° C. in the presence of anisole (2 ml). After evaporation, the residue was extracted with DMF. The DMF filtrate (75 ml) was concentrated to dryness, dissolved in a 1:1 mixture of acetonitrile-$H_2O$ and freeze-dried to give 750 mg of crude product. A portion (200 mg) was purified by preparative HPLC on a C-18 reverse phase support (Waters, μ-Bondapak). Buffer A=15% acetic acid-$H_2O$; B=15% acetic acid-methanol. For the purification, the crude product was suspended in 400 ml of 10% B/90% A buffer, filtered and the filtrate loaded onto the column. A step gradient of 10% B to 55% B was used at a flow rate of 75 ml/min. Homogeneous product fractions were pooled, concentrated and freeze-dried from $H_2O$ to yield (6).

Step B: Deacetylvinblastin Monohydrazide (7)

1 g of vinblastine sulfate was converted to the amine form by extraction in methylene chloride and saturated sodium bicarbonate. The methylene chloride layer was washed with $H_2O$, dried over anhydrous $MgSO_4$ and concentrated to dryness. The vinblastine was then dissolved in anhydrous ethanol (20 ml) and anhydrous hydrazine added (20 ml). The solution was heated (60° C.) under an $N_2$ atmosphere for 17 hrs. The reaction was concentrated to an oil, dissolved in methylene chloride, extracted with $H_2O$ and dried over $MgSO_4$. After evaporation compound (7) was isolated. [Ref: K. S. P. Bhushana Rao et al., J. Med. Chem. (1985), 28:1079.]

Step C: Deacetylvinblastine Acid Azide (8).

Deacetylvinblastine monohydrazide (7) (48 mg, 0.0624 mmol) was dissolved in DMF (3 ml), cooled (−15° C.) and acidified to ~2.5 (pH paper) with HCl/dioxane. Isoamylnitrite (10 μl) was added followed by an additional 10 μl after 10 min. HPLC analysis indicated complete conversion of the hydrazide to azide after 5 min. The azide was maintained in solution at −15° C. until ready for use.

Step D: Deacetylvinblastinyl-Leu-Asn-Lys-Ala-Ser-Try-Gln-Ser-Ser-Ser-Leu-$NH_2$•Acetate (5)

The oligopeptide product (6) from Step A, 32 mg (0.0225 mmol), was dissolved in DMF (1 ml) and cooled (−15° C.). To this solution was added a 1.5 ml DMF solution (0.031 mmol) of desacetylvinblastine acid azide (8). The pH was adjusted to ~7.5 (pH paper) with triethylamine and the reaction stirred at −5° C. (2 hr), and 0° C. for 18 hr. To the reaction was added $H_2O$ (2 ml) and the solution evaporated to dryness. The intermediate was dissolved in DMF (4 ml), cooled (0° C.) and 2 ml of piperidine added. The solution was concentrated to dryness and purified by preparative HPLC as described in Step A. The homogeneous fractions were pooled, concentrated and freeze-dried from H$_2$O to yield (5).

Example 10
Deacetylvinblastinyl-Leu-Asn-Lys-Ala-Ser-Try-Gln-Ser-Ser-Ser-Leu—Dox•Acetate (10).

Step A: Deacetylvinblastinyl-Leu-Asn-Lys(Fmoc)-Ala-Ser-Try-Gln-Ser-Ser-Ser-Leu-Dox•Acetate (9)

The oligopeptide product (6) prepared as described in Example 9, Step A, (166 mg, 0.125 mmol), was dissolved in DMSO (3 ml) and cooled to −15° C. To this solution was added a DMF solution (0.125 mmol) of desacetylvinblastine acid azide (8) prepared as described in Example 9, Step C. The pH was adjusted to ~7.5 (pH paper) with triethylamine and the reaction stirred at −15° C. for 90 mins.

After stirring 18 hours at 0–5° C., the reaction was concentrated to dryness and the crude residue was dissolved in DMF (10 ml) and filtered. Doxorubicin hydrochloride, 62 mg (0.106 mmol), was added to the filtrate followed by 30 μl of triethylamine. The stirred solution was cooled (0° C.) and 27 μl of diphenylphosphoryl azide (DPPA, 0.134 mmol) added. After 5 minutes, an additional 27 μl of DPPA was added and the pH adjusted to ~7.5 (pH paper) with TEA. After 1 hour, an additional 27 μl of DPPA was added, pH adjusted to ~7.5, and the reaction stirred at 0°–5° C. overnight. After 18 hours, the reaction (found to be complete by analytical HPLC) was concentrated to an oil (9).

Step B: Deacetylvinblastinyl-Leu-Asn-Lys-Ala-Ser-Try-Gln-Ser-Ser-Ser-Leu—Dox•Acetate (10).

The above intermediate product (9) was dissolved in DMF (20 ml), cooled (0° C.) and 10 ml of piperidine added. The solution was concentrated to dryness and purified by preparative HPLC. Buffer A=15% acetic acid-H$_2$O; B=15% acetic acid-methanol. The crude product was dissolved in 300 ml of 10% B/90% A buffer, filtered and purified on a C-18 reverse phase HPLC radial compression column (Waters, μ-Bondapak). A step gradient of 10% B to 60% B was used at a flow rate of 75 ml/min (uv=260 nm). Semi-pure product was further purified on C-18 (Waters, Prep Pak) using Buffer A=0.13M pH 3.0 triethylammonium phosphate and Buffer B=acetonitrile. A step gradient of 10% B to 40% B was used at a flow rate of 75 ml/min. (uv=214 nm). Pure product fractions were pooled, diluted with H$_2$O and desalted by applying the product onto the same column and eluting the product as the actetate salt with 90% acetonitrile/ 10% H$_2$O (1% acetic acid). The product fractions were concentrated and freeze dried from H$_2$O to yield the purified product (10).

Example 11
Ac-Lys-Tyr-Gln-Ser-Ser-Ser-Nle-NH-(CH$_2$)$_3$NH-deacetylvinblastine amide (14)

Step A: Deacetylvinblastine-3-aminopropyl amide (11)

To a cooled (−15° C.) a DMF solution (3 ml, 0.0624 mmol) of deacetylvinblastine acid azide (synthesis described in Example 9, Step C) was added 120 μl of 1,3-diaminopropane in DMF (2 ml). The reaction was stirred at −10° C. for 1 hr, filtered and concentrated to dryness to yield (11).

Step B: Deacetylvinblastine-3-aminopropylamide-norleucine amide (12)

To a DMF solution (1 ml) of Boc-Nle (22 mg, 0.095 mmol) was added 318 μl of a 1M solution of HOBT (in NMP) followed by 280 μl of a 1M solution of DCC (in NMP). After 30 min., intermediate (11) (0.0624 mmol) was added in a 3.5 ml DMF. The pH of the reaction was adjusted ~7.5 with diisopropylethylamine. After stirring for 18 hrs the reaction was concentrated to an oil and the Boc protecting group removed by treating the oil with a 1:1 solution of TFA: CH$_2$Cl$_2$ (20 ml). After 5 min. the reaction was concentrated to dryness. Purification was achieved by preparative HPLC on a C-18 reverse phase support (Waters, Delta Pak). Buffer A=0.1% TFA-H$_2$O; B=0.1% TFA-CH$_3$CN. The crude product was loaded in 100% A buffer (100 ml) and a step gradient of 100% A to 30% A was used at a flow rate of 75 ml/min. Homogeneous product fractions were pooled and freeze-dried to yield (12).

Step C: Ac-Lys(Fmoc)-Tyr-Gln-Ser-Ser-Ser-Nle-OH (13)

The above intermediate was prepared as described in Example 9, Step A for the preparation of Ac-Lys(Fmoc)-Tyr-Gln-Ser-Ser-Ser-Leu-OH.

Step D: Ac-Lys-Tyr-Gln-Ser-Ser-Ser-Nle-NH-(CH$_2$)3 NH-deacetylvinblastine amide (14)

The oligopeptide product (13), (70 mg, 0.065 mmol) in DMF (1 ml) was combined with (41 mg, 0.05 mmol) of (12) in DMF (4 ml). The solution was cooled (0° C.) and 17 μl of diphenylphosphoryl azide (0.08 mmol) added. After 5 min. an additional 17 μl of DPPA was added and the pH adjusted to ~7.5 (pH paper) with triethylamine. After 2 hr. additional (13), 35 mg, was added in DMF (0.5 ml) and 17 μl of DPPA. The pH was maintained at ~7.5 with TEA and after 3 hr. an additional 35 mg of (13) was added in DMF (0.5 ml). The reaction was stirred at 0–5° C. After 18 hrs, the reaction was concentrated to dryness, redissolved in DMF (9 ml), cooled (0° C.) and 3 ml of piperidine added. The solution was concentrated to dryness and purified by preparative HPLC. Buffer A=0.1% TFA-H$_2$O; B=0.1% TFA-CH$_3$ CN. The crude product was dissolved in 30% acetic acid –H$_2$O (100 ml) and purified on a C-18 reverse phase HPLC radial compression column (Waters, Delta Pak). A step gradient of 100% A to 70% A was used at a flow rate of 75 ml/min. Semi-pure product fractions were pooled and freeze-dried. Purification to homogeneity was achieved by repurification on a C-4 support (Waters, Delta Pak) as described above. Product fractions were pooled and freeze dried to yield pure (14).

Example 12
Assessment of the Recognition of Oligopeptide-Doxorubicin Conjugates by Free PSA:

The conjugates prepared as described in Examples 7–9 were individually dissolved in PSA digestion buffer (12 mM tris(hydroxymethyl)-aminomethane pH8.0, 25 mM NaCl, 0.5 mM CaCl$_2$) and the solution added to PSA at a molar ration of 100 to 1. Alternatively, the PSA digestion buffer utilized is 50 mM tris(hydroxymethyl)-aminomethane pH7.4, 140 mM NaCl. The reaction is quenched after various reaction times by the addition of trifluoroacetic acid (TFA) to a final 1% (volume/volume). Alternatively the reaction is quenched with 10 mM ZnCl$_2$. The quenched reaction was analyzed by HPLC on a reversed-phase C18 column using an aqueous 0.1%TFA/acetonitrile gradient. The results of the assessment are shown in Tables 5 and 5a of FIG. 5.

Example 13
Assessment of the Cleavage of Oligopeptide-Doxorubicin Conjugates in Cell Conditioned Media:

Cell conditioned serum-free α-MEM media (phenol red minus) was collected 3 days after the addition of the media to either LNCaP or DuPRO (prepared as described in J. Urology, 146:915–919 (1991)) cell lines. The media was concentrated 20 fold using an Amicon® Centriprep™ concentrator with a 10,000 molecular weight cutoff. The LNCaP conditioned media contained free PSA protein at, on average, approximately 100 ng/mL concentration as determined by the Tandem®-E PSA immunodetection kit (Hybritech®). There was no detectable free PSA in the DuPRO cell conditioned media. 100 μL portions of concentrated conditioned media was mixed with 35 μg of a oligopeptide-doxorubicin conjugate prepared as described in Example 7 and the mixture was incubated at 37° C. for 0, 4 and 24 hour time points. The reactions were stopped by the addition of $ZnCl_2$ (to a 0.01M final concentration) and analyzed by HPLC on a reversed-phase C18 column using an aqueous 0.1%TFA/acetonitrile gradient to determine the percentage of peptide-cytotoxic agent conjugate that had been digested. The results of the assessment are shown in Table 6 of FIG. 6.

Example 14
In vitro Assay of Cytotoxicity of Peptidyl Derivatives of Doxorubicin:

The cytotoxicities of the cleaveable oligopeptide-doxorubicin conjugates, prepared as described in Example 7, against a line of cells which is known to be killed by unmodified doxorubicin was assessed with an Alamar Blue assay as described in Example 5. Specifically, cell cultures of LNCaP prostate tumor cells or DuPRO cells in 96 well plates was diluted with medium containing various concentrations of a given conjugate (final plate well volume of 200 μl). The cells were incubated for 3 days at 37° C., 20 μl of Alamar Blue is added to the assay well. The cells were further incubated and the assay plates were read on a EL-310 ELISA reader at the dual wavelengths of 570 and 600 nm at 4 and 7 hours after addition of Alamar Blue. Relative percentage viability at the various concentration of conjugate tested was then calculated versus control (no conjugate) cultures. Cytotoxicities of the conjugates were also compared to the cytotoxicity of unmodified doxorubicin and unmodified oligopeptide assessed in the same assay. Results of this assay are shown in Table 7 of FIG. 7.

Example 15
In vivo Efficacy of Peptidyl-Cytotoxic Agent Conjugates

LNCAP.FGC or DuPRO-1 cells are trypsinized, resuspended in the growth medium and centifuged for 6 mins. at 200×g. The cells are resuspended in serum-free α-MEM and counted. The appropriate volume of this solution containing the desired number of cells is then transferred to a conical centrifuge tube, centrifuged as before and resuspended in the appropriate volume of a cold 1:1 mixture of α-MEM-Matrigel. The suspension is kept on ice until the animals are inoculated.

Male nude mice (10–12 weeks old) are restrained without anesthesia and are inoculated with 0.5 mL of cell suspension on the left flank by subcutaneous injection using a 22G needle. Mice are either given approximately $5 \times 10^5$ DuPRO cells or $1.5 \times 10^7$ LNCaP.FGC cells.

Following inoculation with the tumor cells the mice are treated under one of two protocols:

Protocol A:

One day after cell inoculation the animals are dosed with a 0.1–0.5 mL volume of test conjugate, doxorubicin or vehicle control (sterile water). Dosages of the conjugate and doxorubicin are initially the maximum non-lethal amount, but may be subsequently titrated lower. Identical doses are administered at 24 hour intervals for 5 days. After 10 days, blood samples are removed from the mice and the serum level of PSA is determined. Similar serum PSA levels are determined at 5–10 day intervals. At the end of 5.5 weeks the mice are sacrificed and weights of any tumors present are measured and serum PSA again determined. The animals' weights are determined at the beginning and end of the assay.

Protocol B:

Ten days after cell inoculation,blood samples are removed from the animals and serum levels of PSA are determined. Animals are then grouped according to their PSA serum levels. At 14–15 days after cell inoculation, the animals are dosed with a 0.1–0.5 mL volume of test conjugate, doxorubicin or vehicle control (sterile water). Dosages of the conjugate and doxorubicin are initially the maximum non-lethal amount, but may be subsequently titrated lower. Identical doses are administered at 24 hour intervals for 5 days. Serum PSA levels are determined at 5–10 day intervals. At the end of 5.5 weeks the mice are sacrificed, weights of any tumors present are measured and serum PSA again determined. The animals' weights are determined at the beginning and end of the assay.

What is claimed is:

1. A method of treating benign prostatic hyperplasia which comprises administering to a mammal in need of said treatment a conjugate, said conjugate which comprises a cytotoxic agent attached to an oligopeptide, wherein the oligopeptide is a sequence of amino acids that is recognized and selectively proteolytically cleaved by free prostate specific antigen, wherein the means of attachment is directly through a covalent bond or via a linker unit, and wherein the cytotoxic agent is a member of a class of cytotoxic agents selected from the following classes:

a) anthracycline family of drugs, b) the vinca alkaloid drugs, c) the mitomycins, d) the bleomycins, e) the cytotoxic nucleosides, f) the pteridine family of drugs, g) diynenes, h) estramustine, i) cyclophosphamide, j) the podophyllotoxins, and k) the taxanes;

or a pharmaceutically acceptable salt thereof.

2. A method of treating benign prostatic hyperplasia which comprises administering to a mammal in need of said treatment a conjugate, said conjugate which comprises a cytotoxic agent attached to an oligopeptide, wherein the oligopeptide is a sequence of amino acids that is recognized and selectively proteolytically cleaved by free prostate specific antigen, wherein the means of attachment is directly through a covalent bond or via a linker unit, and wherein the cytotoxic agent is selected from the group consisting of:

a) doxorubicin,
b) carminomycin,
c) daunorubicin,
d) aminopterin,
e) methotrexate,
f) methopterin,
g) dichloro-methotrexate,
h) mitomycin C,
i) porfiromycin,
j) 5-fluorouracil,
k) 6-mercaptopurine,
l) cytosine arabinoside,
m) podophyllotoxin,
n) etoposide,
o) etoposide phosphate,
p) melphalan,
q) vinblastine,
r) vincristine,
s) leurosidine,
t) vindesine,
u) estramustine,
v) cisplatin,
w) cyclophosphamide,
x) leurosine, and
y) taxol;

or the pharmaceutically acceptable salt thereof.

3. The method of treatment according to claim 1 wherein the cytotoxic agent is selected from the group consisting of doxorubicin, vinblastine and desacetylvinblastine or a cytotoxic derivative thereof.

4. The method of treatment according to claim 1 wherein the cytotoxic agent is selected from the group consisting of vinblastine and desacetylvinblastine or a cytotoxic derivative thereof.

5. The method of treatment according to claim 3 wherein the conjugate is of the formula I:

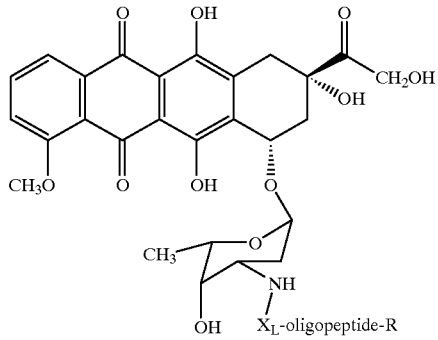

wherein:
oligopeptide is an oligopeptide which is specifically recognized by the free prostate specific antigen (PSA) and is capable of being proteolytically cleaved by the enzymatic activity of the free prostate specific antigen;

$X_L$ is absent or is an amino acid selected from:
a) phenylalanine,
b) leucine,
c) valine,
d) isoleucine,
e) (2-naphthyl)alanine,
f) cyclohexylalanine,
g) diphenylalanine,
h) norvaline, and
i) norleucine, and
j) 1,2,3,4-tetrahydroisoquinoline-3-carboxylic acid;

R is hydrogen or —(C=O)$R^1$; and
$R^1$ is $C_1$–$C_6$-alkyl or aryl;
or the pharmaceutically acceptable salt thereof.

6. The method of treatment according to claim 5 wherein:
oligopeptide is an oligomer of from about 6 to about 100 amino acid residues which include in their amino aicd sequence an amino acid sequence selected from the group consisting of:
a) AsnLysIleSerTyrGln|Ser (SEQ.ID.NO.: 13),
b) LysIleSerTyrGln|Ser (SEQ.ID.NO.: 14),
c) GlyGluAsnGlyValGlnLysAspValSerGlnXaaSerIle Tyr|SerGlnThrGlu (SEQ.ID.NO.: 15),
d) GlyLysGlyIleSerSerGlnTyr|SerAsnThrGluGluArgLeu (SEQ.ID.NO.: 2),
e) AsnLysIleSerTyrTyr|Ser (SEQ.ID.NO.: 127),
f) AsnLysAlaSerTyrGln|Ser (SEQ.ID.NO.: 128),
g) SerTyrGln|SerSer (SEQ.ID.NO.: 129),
h) LysTyrGln|SerSer (SEQ.ID.NO.: 140);
i) hArgTyrGln|SerSer (SEQ.ID.NO.: 141);
j) hArgChaGln|SerSer (SEQ.ID.NO.: 185); and
k) TyrGln|SerSer (SEQ.ID.NO.: 186);

wherein hArg is homoarginine and Xaa is any natural amino acid;

$X_L$ is absent or is an amino acid selected from:
a) leucine,
b) isoleucine,
c) norleucine and
d) valine; and R is acetyl, pivaloyl or benzoyl,
or the pharmaceutically acceptable salt thereof.

7. The method of treatment according to claim 5 wherein the conjugate is:

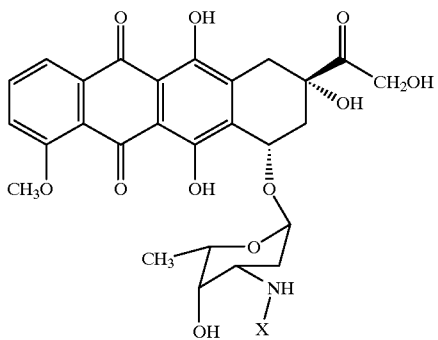

wherein X is:
AsnLysIleSerTyrGlnSer- (SEQ.ID.NO.: 13),
AsnLysIleSerTyrGlnSerSer- (SEQ.ID.NO.: 16),
AsnLysIleSerTyrGlnSerSerSer- (SEQ.ID.NO.: 17),
AsnLysIleSerTyrGlnSerSerSerThr- (SEQ.ID.NO.: 10),
AsnLysIleSerTyrGlnSerSerSerThrGlu- (SEQ.ID.NO.: 3), AlaAsnLysIleSerTyrGlnSerSerSerThrGlu- (SEQ. ID. NO. : 11),
↑
N-terminus Ac-AlaAsnLysIleSerTyrGlnSerSerSerThr- (SEQ.ID.NO.: 117),
Ac-AlaAsnLysIleSerTyrGlnSerSerSerThrLeu- (SEQ.ID.NO.: 70),
Ac-AlaAsnLysAlaSerTyrGlnSerAlaSerThrLeu- (SEQ.ID.NO.: 118),
Ac-AlaAsnLysAlaSerTyrGlnSerAlaSerLeu- (SEQ.ID.NO.: 119),
Ac-AlaAsnLysAlaSerTyrGlnSerSerSerLeu- (SEQ.ID.NO.: 120),
Ac-AlaAsnLysAlaSerTyrGlnSerSerLeu- (SEQ.ID.NO.: 121),
Ac-SerTyrGlnSerSerSerLeu- (SEQ.ID.NO.: 144),
Ac-hArgTyrGlnSerSerSerLeu- (SEQ.ID.NO.: 145),
Ac-LysTyrGlnSerSerSerLeu- (SEQ.ID.NO.: 124), or Ac——LysTyrGlnSerSerNle——— (SEQ.ID.NO.: 146),
↗
N-terminus or the pharmaceutically acceptable salt thereof.

8. The method of treatment according to claim 5 wherein the conjugate is:
Ac-hArgTyrGln-SerSerPro-dox(3') (SEQ.ID.NO.: 151)
Ac-hArgTyrGln-SerPro-dox(3') (SEQ.ID.NO.: 177)
Ac-hArgTyrGln-SerSerSerNle-dox(3') (SEQ.ID.NO.: 154)
Ac-AmfTyrGln-SerSerSerNle-dox(3') (SEQ.ID.NO.: 155)
H$_2$NCO-hArgTyrGln-SerSerSerLeu-dox(3') (SEQ.ID.NO.: 156)
Ac-LysTyrGln-SerSerNle-dox(3') (SEQ.ID.NO.: 146)
Ac-LysTyrGln-SerLysNle-dox(3') (SEQ.ID.NO.: 178)
Ac(cis-p-NH$_2$Cha)TyrGlnSerSerNledox(3') (SEQ.ID.NO.: 161)
Ac-AlaAspLysAla(hArg)TyrGln-SerSerLeu-dox(3') (SEQ.ID.NO.: 160)
Ac-hArgTyrGln-SerAsn-dox(3') (SEQ.ID.NO.: 153)
Ac-hArgTyrGln-SerSerHis-dox(3') (SEQ.ID.NO.: 152)
Ac-(imidazolyl)LysTyrGln-SerSerLeu-dox(3') (SEQ.ID.NO.: 159)
Ac-(imidazolyl)LysTyrGlnSerSerSerNle-dox(3') (SEQ.ID.NO.: 162)
Ac-hArg(Cha)Gln-SerSerSerNle-dox(3') (SEQ.ID.NO.: 163)
Ac-hArg(Me$_2$PO$_3$Tyr)Gln-SerSerSerNle-dox(3') (SEQ.ID.NO.: 167)
Ac-hArgTyrGln-SerSerSerhArg-dox(3') (SEQ.ID.NO.: 164)
Ac-hArg(3-Iodo-Tyr)Gln-SerSerSerNle-dox(3') (SEQ.ID.NO.: 166)
Ac-hArg(O-Me-Tyr)Gln-SerSerSerNle-dox(3') (SEQ.ID.NO.: 169)
Ac-hArg(p-NH$_2$-Phe)Gln-SerSerSerNle-dox(3') (SEQ.ID.NO.: 179)
Ac-hArg(Cha)Gln-SerSerNle-dox(3') (SEQ.ID.NO.: 174)
Ac-hArg(Cha)Gln-SerProNle-dox(3') (SEQ.ID.NO.: 175)
Ac(imidazolyl)Lys(Cha)GlnSerSerSerNle-dox(3') (SEQ.ID.NO.: 172)
Ac-hArg(7-HO-TIC)Gln-SerSerSerNle-dox(3') (SEQ.ID.NO.: 180)
Ac-hArg(3-Fluoro)TyrGlnSerSerSerNle-dox(3') (SEQ.ID.NO.: 176)
Ac-(ornithine)TyrGln-SerSerSerNle-dox(3') (SEQ.ID.NO.: 181)
Ac-LysAlaAlaSerSerSerLeu-dox(3') (SEQ.ID.NO.: 183)
Ac-hArgh(Cha)Gln-SerSerNle-dox(3') (SEQ.ID.NO.: 149)
Ac-AlaArgLysAlaSerTyrGln-SerLeu-dox(3') (SEQ.ID.NO.: 193) and
Ac-(Orn)TyrGln-SerSerSerLeu-dox(3') (SEQ.ID.NO.: 194)
or the pharmaceutically acceptable salt thereof.

9. The method of treatment according to claim 4 wherein the conjugate is of the formula II:

II

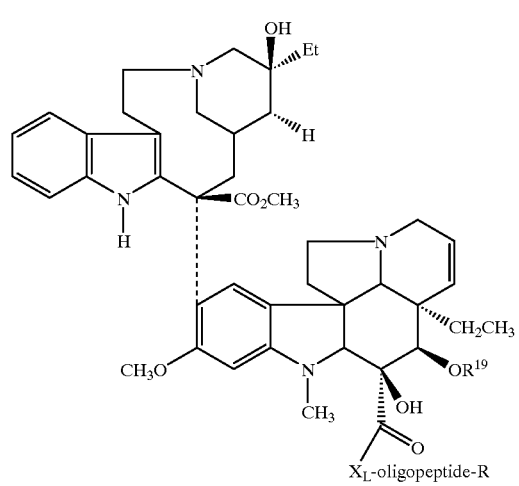

wherein:
oligopeptide is an oligopeptide which is specifically recognized by the free prostate specific antigen (PSA) and is capable of being proteolytically cleaved by the enzymatic activity of the free prostate specific antigen;
$X_L$ is absent or is an amino acid selected from the group consisting of:
a) phenylalanine,
b) leucine,
c) valine,
d) isoleucine, e) (2-naphthyl)alanine,
f) cyclohexylalanine,
g) diphenylalanine,
h) norvaline,
i) norleucine, and
j) 1,2,3,4-tetrahydroisoquinoline-3-carboxylic acid; or $X_L$ is —NH—(CH$_2$)$_n$—NH—

R is hydrogen or —(C=O)R$^1$;

R$^1$ is C$_1$–C$_6$-alkyl or aryl;

R$^{19}$ is hydrogen or acetyl; and n is 1, 2, 3, 4 or 5, or the pharmaceutically acceptable salt thereof.

10. A method of treating benign prostatic hyperplasia which comprises administering to a mammal in need of said treatment a conjugate, said conjugate which comprises two cytotoxic agents attached to an oligopeptide, wherein the oligopeptide is a sequence of amino acids that is recognized and selectively proteolytically cleaved by free prostate specific antigen, wherein the means of attachment is directly through a covalent bond or via a linker unit, and wherein the cytotoxic agents are members of classes of cytotoxic agents independently selected from the following classes:

a) anthracycline family of drugs,
b) the vinca alkaloid drugs,
c) the mitomycins,
d) the bleomycins,
e) the cytotoxic nucleosides,
f) the pteridine family of drugs,
g) diynenes,
h) estramustine,
i) cyclophosphamide,
j) the podophyllotoxins, and
k) the taxanes;

or the pharmaceutically acceptable salt thereof.

11. A pharmaceutical composition useful for treating benign prostatic hyperplasia comprising a pharmaceutical carrier, and dispersed therein, a therapeutically effective amount of a conjugate, said conjugate which comprises a cytotoxic agent attached to an oligopeptide, wherein the oligopeptide is a sequence of amino acids that is recognized and selectively proteolytically cleaved by free prostate specific antigen, wherein the means of attachment is directly through a covalent bond or via a linker unit, and wherein the cytotoxic agent is a member of a class of cytotoxic agents selected from the following classes:

a) anthracycline family of drugs,
b) the vinca alkaloid drugs,
c) the mitomycins,
d) the bleomycins,
e) the cytotoxic nucleosides,
f) the pteridine family of drugs,
g) diynenes,
h) estramustine,
i) cyclophosphamide,
j) the podophyllotoxins, and
k) the taxanes;

or the pharmaceutically acceptable salt thereof.

12. The composition according to claim 11 wherein the conjugate is of the formula I:

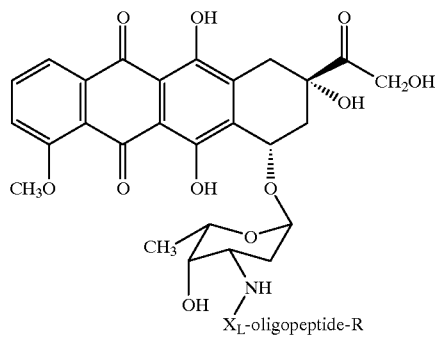

wherein:

oligopeptide is an oligopeptide which is specifically recognized by the free prostate specific antigen (PSA) and is capable of being proteolytically cleaved by the enzymatic activity of the free prostate specific antigen;

$X_L$ is absent or is an amino acid selected from the group consisting of:

a) phenylalanine,
b) leucine,
c) valine,
d) isoleucine,
e) (2-naphthyl)alanine,
f) cyclohexylalanine,
g) diphenylalanine,
h) norvaline,
i) norleucine, and
j) 1,2,3,4-tetrahydroisoquinoline-3-carboxylic acid;

R is hydrogen or —(C=O)R$^1$; and

R$^1$ is C$_1$–C$_6$-alkyl or aryl, or the pharmaceutically acceptable salt thereof.

13. A pharmaceutical composition useful for treating benign prostatic hyperplasia comprising a pharmaceutical carrier, and dispersed therein, a therapeutically effective amount of a conjugate, said conjugate which comprises two cytotoxic agents attached to an oligopeptide, wherein the oligopeptide is a sequence of amino acids that is recognized and selectively proteolytically cleaved by free prostate specific antigen, wherein the means of attachment is a covalent bond or a chemical linker, and wherein cytotoxic agents are members of a class of cytotoxic agents independently selected from the following classes:

a) anthracycline family of drugs,
b) the vinca alkaloid drugs,
c) the mitomycins,
d) the bleomycins,
e) the cytotoxic nucleosides,
f) the pteridine family of drugs,
g) diynenes,
h) estramustine,
i) cyclophosphamide, j) the podophyllotoxins, and k) the taxanes;

or the pharmaceutically acceptable salt thereof.

14. The method of treatment according to claim 9 wherein the conjugate is of the formula IIa:

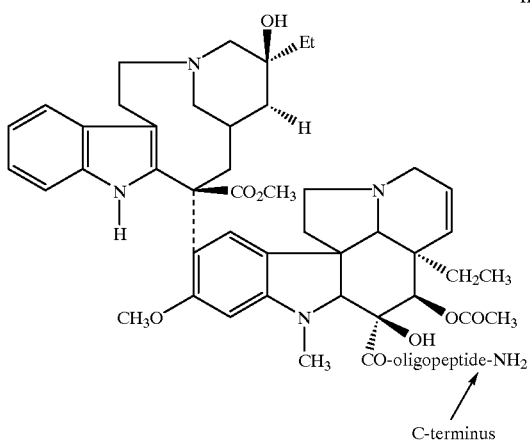

IIa wherein:

oligopeptide is an oligopeptide which is specifically recognized by the free prostate specific antigen (PSA) and is capable of being proteolytically cleaved by the enzymatic activity of the free prostate specific antigen, or the pharmaceutically acceptable salt thereof.

15. The method of treatment according to claim 9 wherein the conjugate is selected from:

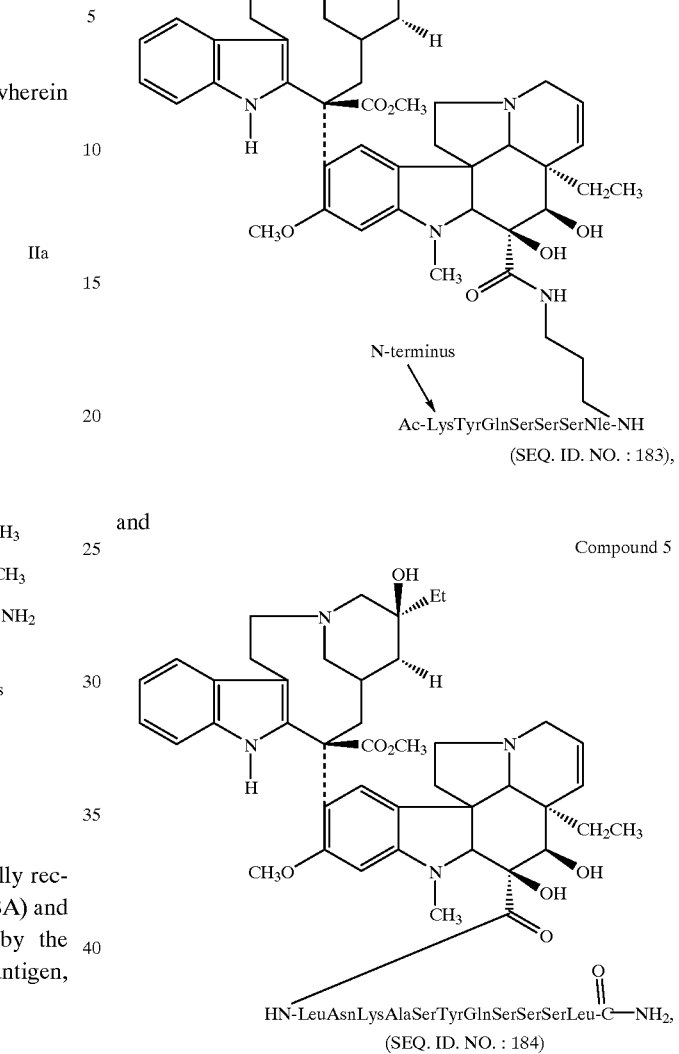

Compound 14

Ac-LysTyrGlnSerSerSerNle-NH
(SEQ. ID. NO. : 183), and

Compound 5

HN-LeuAsnLysAlaSerTyrGlnSerSerSerLeu-C(=O)—NH$_2$,
(SEQ. ID. NO. : 184)

or the pharmaceutically acceptable salt thereof.

16. The method of treatment according to claim 10 wherein the conjugate is

Compound 10

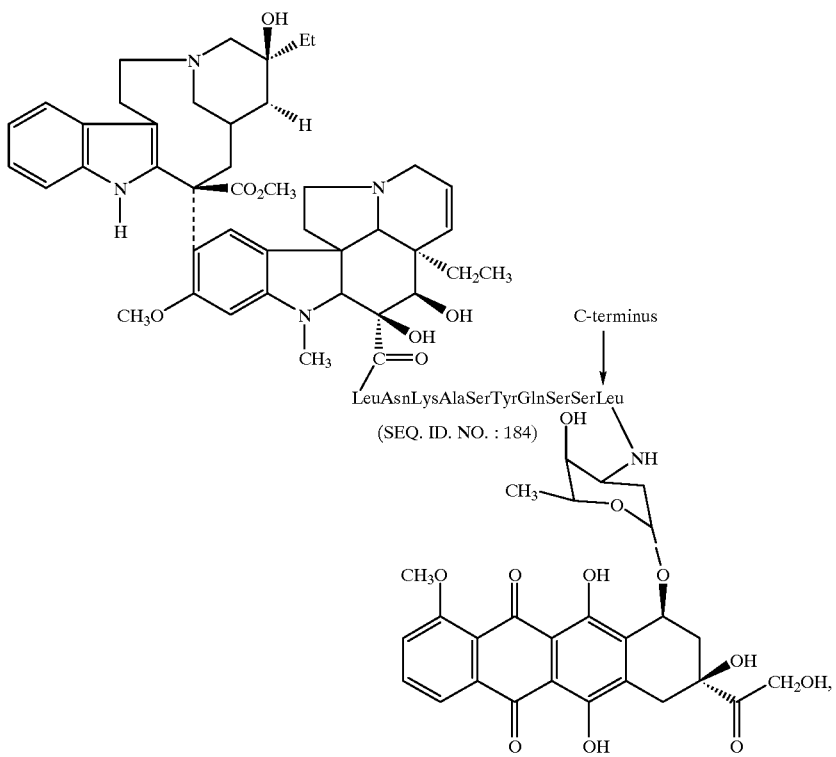

or the pharmaceutically acceptable salt thereof.

17. The composition according to claim 11 wherein the conjugate is:

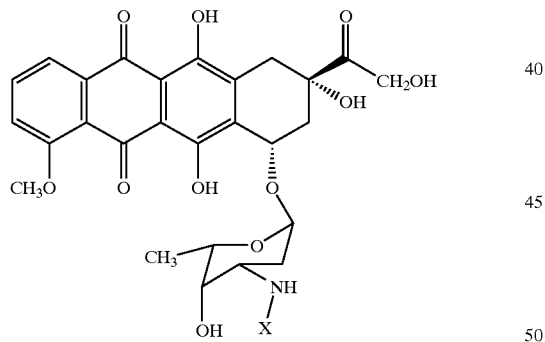

wherein X is:
AsnLysIleSerTyrGlnSer- (SEQ.ID.NO.: 13),
AsnLysIleSerTyrGlnSerSer- (SEQ.ID.NO.: 16),
AsnLysIleSerTyrGlnSerSerSer- (SEQ.ID.NO.: 17),
AsnLysIleSerTyrGlnSerSerThr- (SEQ.ID.NO.: 10),
AsnLysIleSerTyrGlnSerSerThrGlu- (SEQ.ID.NO.: 3), AlaAsnLysIleSerTyrGlnSerSerThrGlu- (SEQ. ID. NO. : 11),
↑
N-terminus Ac-AlaAsnLysIleSerTyrGlnSerSerSerThr- (SEQ.ID.NO.: 117), Ac-AlaAsnLysIleSerTyrGlnSerSerSerThrLeu- (SEQ.ID.NO.: 70),
Ac-AlaAsnLysAlaSerTyrGlnSerAlaSerThrLeu- (SEQ.ID.NO.: 118),
Ac-AlaAsnLysAlaSerTyrGlnSerAlaSerLeu- (SEQ.ID.NO.: 119),
Ac-AlaAsnLysAlaSerTyrGlnSerSerSerLeu- (SEQ.ID.NO.: 120),
Ac-AlaAsnLysAlaSerTyrGlnSerSerLeu- (SEQ.ID.NO.: 121),
Ac-SerTyrGlnSerSerSerLeu- (SEQ.ID.NO.: 144),
Ac-hArgTyrGlnSerSerSerLeu- (SEQ.ID.NO.: 145),
Ac-LysTyrGlnSerSerSerLeu- (SEQ.ID.NO.: 124), or Ac-LysTyrGlnSerSerNle- (SEQ. ID. NO. : 146).
↑
N-terminus or the pharmaceutically acceptable salt thereof.

18. The composition according to claim 11 wherein the conjugate is selected from the group consisting of:
Ac-hArgTyrGln-SerSerPro-dox(3') (SEQ.ID.NO.: 151)
Ac-hArgTyrGln-SerPro-dox(3') (SEQ.ID.NO.: 177)
Ac-hArgTyrGln-SerSerSerNle-dox(3') (SEQ.ID.NO.: 154)
Ac-AmfTyrGln-SerSerSerNle-dox(3') (SEQ.ID.NO.: 155)
H$_2$NCO-hArgTyrGln-SerSerSerLeu-dox(3') (SEQ.ID.NO.: 156)
Ac-LysTyrGln-SerSerNle-dox(3') (SEQ.ID.NO.: 146)
Ac-LysTyrGln-SerLysNle-dox(3') (SEQ.ID.NO.: 178)
Ac(cis-p-NH$_2$Cha)TyrGlnSerSerNledox(3') (SEQ.ID.NO.: 161)

Ac-AlaAspLysAla(hArg)TyrGln-SerSerLeu-dox(3') (SEQ.ID.NO.: 160)
Ac-hArgTyrGln-SerAsn-dox(3') (SEQ.ID.NO.: 153)
Ac-hArgTyrGln-SerSerHis-dox(3') (SEQ.ID.NO.: 152)
Ac-(imidazolyl)LysTyrGln-SerSerLeu-dox(3') (SEQ.ID.NO.: 159)
Ac-(imidazolyl)LysTyrGlnSerSerSerNle-dox(3') (SEQ.ID.NO.: 162)
Ac-hArg(Cha)Gln-SerSerSerNle-dox(3') (SEQ.ID.NO.: 163)
Ac-hArg(Me$_2$PO$_3$Tyr)Gln-SerSerSerNle-dox(3') (SEQ.ID.NO.: 167)
Ac-hArgTyrGln-SerSerSerhArg-dox(3') (SEQ.ID.NO.: 164)
Ac-hArg(3-Iodo-Tyr)Gln-SerSerSerNle-dox(3') (SEQ.ID.NO.: 166)
Ac-hArg(O-Me-Tyr)Gln-SerSerSerNle-dox(3') (SEQ.ID.NO.: 169)
Ac-hArg(p-NH$_2$-Phe)Gln-SerSerSerNle-dox(3') (SEQ.ID.NO.: 179)
Ac-hArg(Cha)Gln-SerSerNle-dox(3') (SEQ.ID.NO.: 174)
Ac-hArg(Cha)Gln-SerProNle-dox(3') (SEQ.ID.NO.: 175)
Ac(imidazolyl)Lys(Cha)GlnSerSerSerNle-dox(3') (SEQ.ID.NO.: 172)
Ac-hArg(7-HO-TIC)Gln-SerSerSerNle-dox(3') (SEQ.ID.NO.: 180)
Ac-hArg(3-Fluoro)TyrGlnSerSerSerNle-dox(3') (SEQ.ID.NO.: 176)
Ac-(ornithine)TyrGln-SerSerSerNle-dox(3') (SEQ.ID.NO.: 181)
Ac-LysAlaAlaSerSerSerLeu-dox(3') (SEQ.ID.NO.: 183)
Ac-hArgh(Cha)Gln-SerSerNle-dox(3') (SEQ.ID.NO.: 149)
Ac-AlaArgLysAlaSerTyrGln-SerLeu-dox(3') (SEQ.ID.NO.: 193) and
Ac-(Orn)TyrGln-SerSerSerLeu-dox(3') (SEQ.ID.NO.: 194)
or the pharmaceutically acceptable salt thereof.

19. The composition according to claim 11 wherein the conjugate is of the formula II:

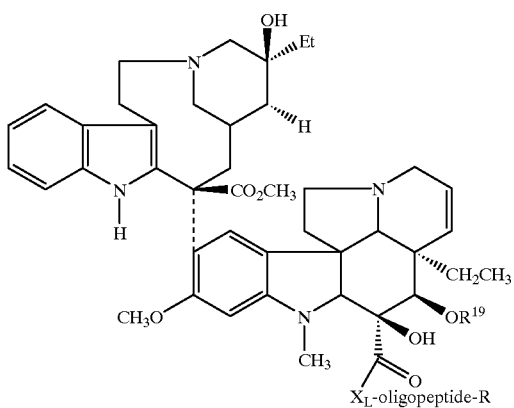

wherein:
oligopeptide is an oligopeptide which is specifically recognized by the free prostate specific antigen (PSA) and is capable of being proteolytically cleaved by the enzymatic activity of the free prostate specific antigen;
X$_L$ is absent or is an amino acid selected from:
a) phenylalanine,
b) leucine,
c) valine,
d) isoleucine,
e) (2-naphthyl)alanine,
f) cyclohexylalanine,
g) diphenylalanine,
h) norvaline, and
i) norleucine, and
j) 1,2,3,4-tetrahydroisoquinoline-3-carboxylic acid; or
X$_L$ is —NH—(CH$_2$)$_n$—NH—
R is hydrogen or —(C=O)R$^1$;
R$^1$ is C$_1$–C$_6$-alkyl or aryl;
R$^{19}$ is hydrogen or acetyl; and
n is 1, 2, 3, 4 or 5,
or the pharmaceutically acceptable salt thereof.

20. The composition according to claim 19 wherein the conjugate is:

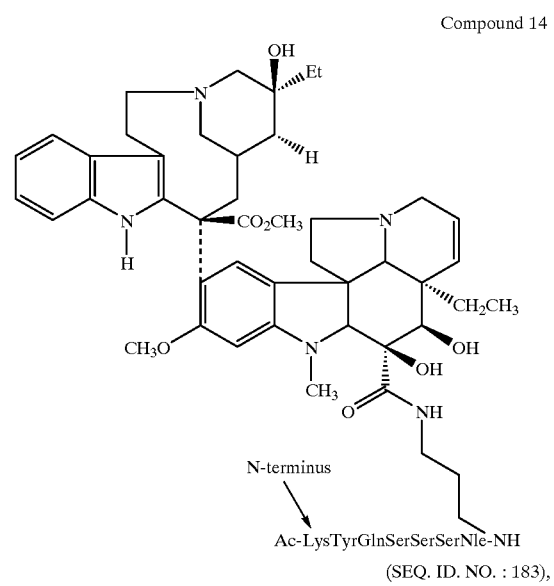

or the pharmaceutically acceptable salt thereof.

21. The composition according to claim 11 wherein the conjugate is of the formula II:

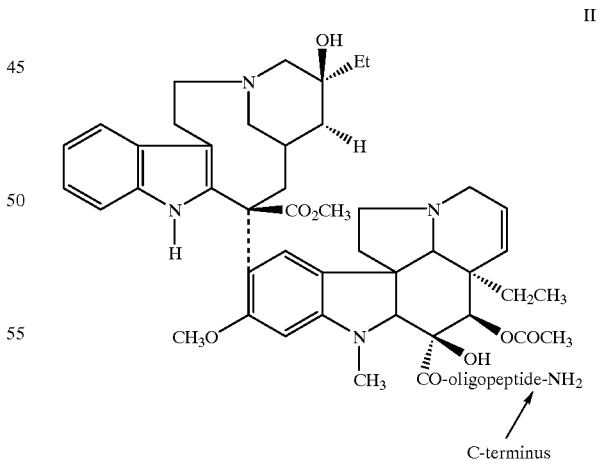

wherein:
oligopeptide is an oligopeptide which is specifically recognized by the free prostate specific antigen (PSA) and is capable of being proteolytically cleaved by the enzymatic activity of the free prostate specific antigen,
or the pharmaceutically acceptable salt thereof.

22. The composition according to claim 21 wherein the conjugate is:
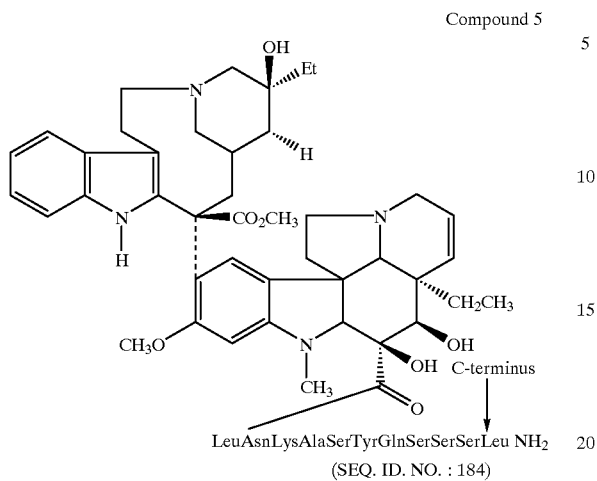
Compound 5
or the pharmaceutically acceptable salt thereof.
23. The composition according to claim 13 wherein the conjugate is:
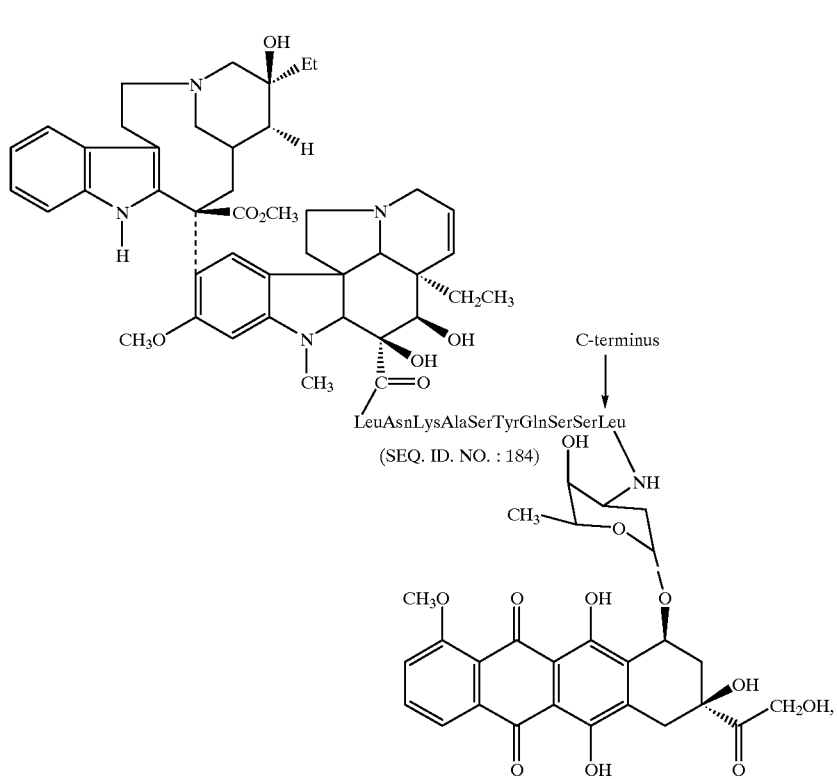
Compound 10
or the pharmaceutically acceptable salt thereof.
* * * * *

SEQUENCE LISTING

<160> NUMBER OF SEQ ID NOS: 194

<210> SEQ ID NO 1
<211> LENGTH: 462
<212> TYPE: PRT
<213> ORGANISM: human

<400> SEQUENCE: 1

Met Lys Pro Asn Ile Ile Phe Val Leu Ser Leu Leu Leu Ile Leu Glu
1               5                   10                  15

Lys Gln Ala Ala Val Met Gly Gln Lys Gly Gly Ser Lys Gly Arg Leu
            20                  25                  30

Pro Ser Glu Phe Ser Gln Phe Pro His Gly Gln Lys Gly Gln His Tyr
        35                  40                  45

Ser Gly Gln Lys Gly Lys Gln Gln Thr Glu Ser Lys Gly Ser Phe Ser
    50                  55                  60

-continued

```
Ile Gln Tyr Thr Tyr His Val Asp Ala Asn Asp His Asp Gln Ser Arg
 65                  70                  75                  80

Lys Ser Gln Gln Tyr Asp Leu Asn Ala Leu His Lys Thr Thr Lys Ser
                 85                  90                  95

Gln Arg His Leu Gly Ser Gln Gln Leu Leu His Asn Lys Gln Glu
            100                 105                 110

Gly Arg Asp His Asp Lys Ser Lys Gly His Phe His Arg Val Val Ile
            115                 120                 125

His His Lys Gly Gly Lys Ala His Arg Gly Thr Gln Asn Pro Ser Gln
    130                 135                 140

Asp Gln Gly Asn Ser Pro Ser Gly Lys Gly Ile Ser Gln Tyr Ser
145                 150                 155                 160

Asn Thr Glu Glu Arg Leu Trp Val His Gly Leu Ser Lys Glu Gln Thr
                165                 170                 175

Ser Val Ser Gly Ala Gln Lys Gly Arg Lys Gln Gly Gly Ser Gln Ser
            180                 185                 190

Ser Tyr Val Leu Gln Thr Glu Glu Leu Val Ala Asn Lys Gln Gln Arg
            195                 200                 205

Glu Thr Lys Asn Ser His Gln Asn Lys Gly His Tyr Gln Asn Val Val
    210                 215                 220

Glu Val Arg Glu Glu His Ser Ser Lys Val Gln Thr Ser Leu Cys Pro
225                 230                 235                 240

Ala His Gln Asp Lys Leu Gln His Gly Ser Lys Asp Ile Phe Ser Thr
                245                 250                 255

Gln Asp Glu Leu Leu Val Tyr Asn Lys Asn Gln His Gln Thr Lys Asn
            260                 265                 270

Leu Asn Gln Asp Gln Gln His Gly Arg Lys Ala Asn Lys Ile Ser Tyr
            275                 280                 285

Gln Ser Ser Thr Glu Glu Arg Arg Leu His Tyr Gly Glu Asn Gly
    290                 295                 300

Val Gln Lys Asp Val Ser Gln Ser Ser Ile Tyr Ser Gln Thr Glu Glu
305                 310                 315                 320

Lys Ala Gln Gly Lys Ser Gln Lys Gln Ile Thr Ile Pro Ser Gln Glu
                325                 330                 335

Gln Glu His Ser Gln Lys Ala Asn Lys Ile Ser Tyr Gln Ser Ser Ser
            340                 345                 350

Thr Glu Glu Arg Arg Leu His Tyr Gly Glu Asn Gly Val Gln Lys Asp
            355                 360                 365

Val Ser Gln Arg Ser Ile Tyr Ser Gln Thr Glu Lys Leu Val Ala Gly
    370                 375                 380

Lys Ser Gln Ile Gln Ala Pro Asn Pro Lys Gln Glu Pro Trp His Gly
385                 390                 395                 400

Glu Asn Ala Lys Gly Glu Ser Gly Gln Ser Thr Asn Arg Glu Gln Asp
                405                 410                 415

Leu Leu Ser His Glu Gln Lys Gly Arg His Gln His Gly Ser His Gly
            420                 425                 430

Gly Leu Asp Ile Val Ile Ile Glu Gln Glu Asp Asp Ser Asp Arg His
    435                 440                 445

Leu Ala Gln His Leu Asn Asn Asp Arg Asn Pro Leu Phe Thr
450                 455                 460
```

<210> SEQ ID NO 2
<211> LENGTH: 15

```
<212> TYPE: PRT
<213> ORGANISM: Artificial Sequence
<220> FEATURE:
<223> OTHER INFORMATION: completely synthetic amino acid sequence

<400> SEQUENCE: 2

Gly Lys Gly Ile Ser Ser Gln Tyr Ser Asn Thr Glu Glu Arg Leu
 1               5                  10                  15

<210> SEQ ID NO 3
<211> LENGTH: 11
<212> TYPE: PRT
<213> ORGANISM: Artificial Sequence
<220> FEATURE:
<223> OTHER INFORMATION: completely synthetic amino acid sequence

<400> SEQUENCE: 3

Asn Lys Ile Ser Tyr Gln Ser Ser Ser Thr Glu
 1               5                  10

<210> SEQ ID NO 4
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 4

Gly Glu Asn Gly Val Gln Lys Asp Val Ser Gln Arg Ser Ile Tyr Ser
 1               5                  10                  15

Gln Thr Glu

<210> SEQ ID NO 5
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 5

Gly Glu Asn Gly Val Gln Lys Asp Val Ser Gln Ser Ser Ile Tyr Ser
 1               5                  10                  15

Gln Thr Glu

<210> SEQ ID NO 6
<211> LENGTH: 25
<212> TYPE: PRT
<213> ORGANISM: Artificial Sequence
<220> FEATURE:
<223> OTHER INFORMATION: completely synthetic amino acid sequence

<400> SEQUENCE: 6

Gly Arg Lys Ala Asn Lys Ile Ser Tyr Gln Ser Ser Ser Thr Glu Glu
 1               5                  10                  15

Arg Arg Leu His Tyr Gly Glu Asn Gly
             20                  25

<210> SEQ ID NO 7
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 7
```

-continued

Ser Tyr Gln Ser Ser Ser Thr Glu
1               5

<210> SEQ ID NO 8
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 8

Ile Ser Tyr Gln Ser Ser Ser Thr Glu
1               5

<210> SEQ ID NO 9
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 9

Lys Ile Ser Tyr Gln Ser Ser Ser Thr Glu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 10

Asn Lys Ile Ser Tyr Gln Ser Ser Ser Thr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 11

Ala Asn Lys Ile Ser Tyr Gln Ser Ser Ser Thr Glu
1               5                   10

<210> SEQ ID NO 12
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 12

Ala Gly Pro Thr Gly Ala Ser Ala
1               5

<210> SEQ ID NO 13
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 13

Asn Lys Ile Ser Tyr Gln Ser

```
                                        1               5

<210> SEQ ID NO 14
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 14

Lys Ile Ser Tyr Gln Ser
  1               5

<210> SEQ ID NO 15
<211> LENGTH: 19
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (12)...(12)
<223> OTHER INFORMATION: Xaa = any natural amino acid

<400> SEQUENCE: 15

Gly Glu Asn Gly Val Gln Lys Asp Val Ser Gln Xaa Ser Ile Tyr Ser
  1               5                  10                  15

Gln Thr Glu

<210> SEQ ID NO 16
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 16

Asn Lys Ile Ser Tyr Gln Ser Ser
  1               5

<210> SEQ ID NO 17
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 17

Asn Lys Ile Ser Tyr Gln Ser Ser Ser
  1               5

<210> SEQ ID NO 18
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 18

Ala Asn Lys Ile Ser Tyr Gln Ser Ser Ser
  1               5                  10

<210> SEQ ID NO 19
<211> LENGTH: 10
<212> TYPE: PRT
<213> ORGANISM: Artificial Sequence
<220> FEATURE:
<223> OTHER INFORMATION: completely synthetic amino acid sequence
```

<400> SEQUENCE: 19

Lys Ile Ser Tyr Gln Ser Ser Ser Thr Glu
1               5                   10

<210> SEQ ID NO 20
<211> LENGTH: 17
<212> TYPE: PRT
<213> ORGANISM: Artificial Sequence
<220> FEATURE:
<223> OTHER INFORMATION: completely synthetic amino acid sequence

<400> SEQUENCE: 20

Gln Leu Asp Asn Lys Ile Ser Tyr Gln Ser Ser Ser Thr His Gln Ser
1               5                   10                  15

Ser

<210> SEQ ID NO 21
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 21

Asn Arg Ile Ser Tyr Gln Ser
1               5

<210> SEQ ID NO 22
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 22

Asn Lys Val Ser Tyr Gln Ser
1               5

<210> SEQ ID NO 23
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 23

Asn Lys Met Ser Tyr Gln Ser Ser
1               5

<210> SEQ ID NO 24
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 24

Asn Lys Leu Ser Tyr Gln Ser Ser
1               5

<210> SEQ ID NO 25
<211> LENGTH: 9
<212> TYPE: PRT
<213> ORGANISM: Artificial Sequence
<220> FEATURE:

-continued

<223> OTHER INFORMATION: completely synthetic amino acid sequence

<400> SEQUENCE: 25

Asn Lys Ile Thr Tyr Gln Ser Ser Ser
 1               5

<210> SEQ ID NO 26
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 26

Asn Lys Ile Ser Phe Gln Ser Ser Ser
 1               5

<210> SEQ ID NO 27
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 27

Asn Lys Ile Ser Trp Gln Ser Ser Ser Thr
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 28

Asn Lys Ile Ser Tyr Asn Ser Ser Ser Thr
 1               5                  10

<210> SEQ ID NO 29
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 29

Asn Lys Ile Ser Tyr Gln Thr Ser Ser Thr
 1               5                  10

<210> SEQ ID NO 30
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 30

Asn Lys Ile Ser Tyr Gln Ser
 1               5

<210> SEQ ID NO 31
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 31

Gln Lys Ile Ser Tyr Gln Ser Ser
1               5

<210> SEQ ID NO 32
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 32

Asn Arg Ile Thr Tyr Gln Ser Ser Ser
1               5

<210> SEQ ID NO 33
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 33

Asn Arg Ile Ser Phe Gln Ser Ser Ser Thr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 34

Gln Lys Ile Ser Tyr Gln Thr Ser Ser Thr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 35

Asn Arg Ile Ser Trp Gln Ser Ser Ser Thr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 36

Asn Arg Ile Ser Tyr Gln Thr Ser Ser Thr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: completely synthetic amino acid sequence

```
<400> SEQUENCE: 37

Asn Lys Ile Thr Tyr Gln Thr Ser Ser Thr
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 38

Asn Lys Leu Ser Tyr Gln Thr Ser Ser Thr
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 39

Gln Lys Leu Ser Tyr Gln Ser Ser Ser Thr
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 40

Asn Arg Leu Ser Tyr Gln Thr Ser Ser Thr
 1               5                  10

<210> SEQ ID NO 41
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 41

Asn Lys Val Ser Phe Gln Ser Ser Ser Thr
 1               5                  10

<210> SEQ ID NO 42
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 42

Asn Arg Val Ser Trp Gln Ser Ser Ser Thr
 1               5                  10

<210> SEQ ID NO 43
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 43
```

Gln Lys Val Ser Tyr Gln Ser Ser Ser Thr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 44

Asn Lys Ile Ser Tyr Gln Ser Ser Ser Thr
1               5                   10

<210> SEQ ID NO 45
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 45

Gly Glu Gln Gly Val Gln Lys Asp Val Ser Gln Ser Ser Ile Tyr Ser
1               5                   10                  15

Gln Thr Glu

<210> SEQ ID NO 46
<211> LENGTH: 15
<212> TYPE: PRT
<213> ORGANISM: Artificial Sequence
<220> FEATURE:
<223> OTHER INFORMATION: completely synthetic amino acid sequence

<400> SEQUENCE: 46

Gly Lys Gly Ile Ser Ser Gln Tyr Ser Asn Thr Asp Glu Arg Leu
1               5                   10                  15

<210> SEQ ID NO 47
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 47

Gly Glu Asn Gly Leu Gln Lys Asp Val Ser Gln Ser Ser Ile Tyr Ser
1               5                   10                  15

Gln Thr Glu

<210> SEQ ID NO 48
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 48

Gly Glu Asn Gly Val Asn Lys Asp Val Ser Gln Ser Ser Ile Tyr Ser
1               5                   10                  15

Gln Thr Glu

<210> SEQ ID NO 49
<211> LENGTH: 19
<212> TYPE: PRT

```
<213> ORGANISM: Artificial Sequence
<220> FEATURE:
<223> OTHER INFORMATION: completely synthetic amino acid sequence

<400> SEQUENCE: 49

Gly Glu Asn Gly Val Gln Arg Asp Val Ser Gln Arg Ser Ile Tyr Ser
 1               5                  10                  15

Gln Thr Glu

<210> SEQ ID NO 50
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 50

Gly Glu Asn Gly Val Gln Lys Asp Val Ser Gln Lys Ser Ile Tyr Ser
 1               5                  10                  15

Gln Thr Glu

<210> SEQ ID NO 51
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 51

Gly Glu Asn Gly Val Gln Lys Asp Leu Ser Gln Thr Ser Ile Tyr Ser
 1               5                  10                  15

Gln Thr Glu

<210> SEQ ID NO 52
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 52

Gly Glu Asn Gly Val Gln Lys Asp Val Ser Gln Ser Ser Ile Phe Ser
 1               5                  10                  15

Gln Thr Glu

<210> SEQ ID NO 53
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 53

Gly Glu Asn Gly Val Gln Lys Asp Met Ser Gln Ser Ser Ile Tyr Thr
 1               5                  10                  15

Gln Thr Glu

<210> SEQ ID NO 54
<211> LENGTH: 19
<212> TYPE: PRT
<213> ORGANISM: Artificial Sequence
<220> FEATURE:
<223> OTHER INFORMATION: completely synthetic amino acid sequence
```

-continued

<400> SEQUENCE: 54

Gly Glu Asn Gly Val Gln Lys Asp Val Ser Gln Arg Ser Ile Tyr Thr
1               5                   10                  15

Gln Thr Glu

<210> SEQ ID NO 55
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 55

Gly Glu Asn Gly Val Gln Lys Asp Val Ser Gln Ser Ser Ile Tyr Ser
1               5                   10                  15

Gln Ser Glu

<210> SEQ ID NO 56
<211> LENGTH: 19
<212> TYPE: PRT
<213> ORGANISM: Artificial Sequence
<220> FEATURE:
<223> OTHER INFORMATION: completely synthetic amino acid sequence

<400> SEQUENCE: 56

Gly Glu Asn Gly Val Gln Lys Asp Val Ser Gln Arg Ser Ile Tyr Ser
1               5                   10                  15

Asn Thr Glu

<210> SEQ ID NO 57
<211> LENGTH: 15
<212> TYPE: PRT
<213> ORGANISM: Artificial Sequence
<220> FEATURE:
<223> OTHER INFORMATION: completely synthetic amino acid sequence

<400> SEQUENCE: 57

Gly Lys Ala Ile Ser Ser Gln Tyr Ser Asn Thr Glu Glu Arg Leu
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: completely synthetic amino acid sequence

<400> SEQUENCE: 58

Gly Lys Gly Ile Ser Ser Gln Tyr Ser Asn Ser Glu Glu Arg Leu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: completely synthetic amino acid sequence

<400> SEQUENCE: 59

Gly Arg Gly Ile Ser Ser Gln Tyr Ser Asn Thr Glu Glu Arg Leu
1               5                   10                  15

<210> SEQ ID NO 60
<211> LENGTH: 15

```
<212> TYPE: PRT
<213> ORGANISM: Artificial Sequence
<220> FEATURE:
<223> OTHER INFORMATION: completely synthetic amino acid sequence

<400> SEQUENCE: 60

Gly Lys Gly Ile Thr Ser Gln Tyr Ser Asn Thr Glu Glu Arg Leu
 1               5                  10                  15

<210> SEQ ID NO 61
<211> LENGTH: 15
<212> TYPE: PRT
<213> ORGANISM: Artificial Sequence
<220> FEATURE:
<223> OTHER INFORMATION: completely synthetic amino acid sequence

<400> SEQUENCE: 61

Gly Lys Gly Ile Ser Thr Gln Tyr Ser Asn Thr Glu Glu Arg Leu
 1               5                  10                  15

<210> SEQ ID NO 62
<211> LENGTH: 15
<212> TYPE: PRT
<213> ORGANISM: Artificial Sequence
<220> FEATURE:
<223> OTHER INFORMATION: completely synthetic amino acid sequence

<400> SEQUENCE: 62

Gly Lys Gly Ile Ser Ser Asn Tyr Ser Asn Thr Glu Glu Arg Leu
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: completely synthetic amino acid sequence

<400> SEQUENCE: 63

Ala Lys Gly Ile Ser Ser Gln Tyr Ser Asn Thr Glu Glu Arg Leu
 1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: completely synthetic amino acid sequence

<400> SEQUENCE: 64

Gly Lys Gly Ile Ser Ser Gln Phe Ser Asn Thr Glu Glu Arg Leu
 1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: completely synthetic amino acid sequence

<400> SEQUENCE: 65

Gly Lys Gly Ile Ser Ser Gln Tyr Thr Asn Ser Glu Glu Arg Leu
 1               5                  10                  15

<210> SEQ ID NO 66
<211> LENGTH: 15
<212> TYPE: PRT
```

```
<213> ORGANISM: Artificial Sequence
<220> FEATURE:
<223> OTHER INFORMATION: completely synthetic amino acid sequence

<400> SEQUENCE: 66

Gly Lys Gly Ile Ser Ser Gln Tyr Ser Asn Ser Glu Glu Arg Leu
 1               5                  10                  15

<210> SEQ ID NO 67
<211> LENGTH: 25
<212> TYPE: PRT
<213> ORGANISM: Artificial Sequence
<220> FEATURE:
<223> OTHER INFORMATION: completely synthetic amino acid sequence

<400> SEQUENCE: 67

Ser Gln Lys Ala Asn Lys Ile Ser Tyr Gln Ser Ser Ser Thr Glu Glu
 1               5                  10                  15
        Arg Arg Leu His Tyr Gly Glu Asn Gly
                    20                  25

<210> SEQ ID NO 68
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 68

Ile Ser Tyr Gln Ser Ser Ser Thr
 1               5

<210> SEQ ID NO 69
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 69

Ala Asn Lys Ile Ser Tyr Gln Ser Ser
 1               5

<210> SEQ ID NO 70
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 70

Ala Asn Lys Ile Ser Tyr Gln Ser Ser Ser Thr Leu
 1               5                  10

<210> SEQ ID NO 71
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 71

Ala Asn Gly Ile Ser Tyr Gln Ser Ser Ser Thr Glu
 1               5                  10

<210> SEQ ID NO 72
<211> LENGTH: 12
```

```
<212> TYPE: PRT
<213> ORGANISM: Artificial Sequence
<220> FEATURE:
<223> OTHER INFORMATION: completely synthetic amino acid sequence

<400> SEQUENCE: 72

Ala Asn Pro Ile Ser Tyr Gln Ser Ser Ser Thr Glu
 1               5                  10

<210> SEQ ID NO 73
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 73

Ala Asn Lys Ile Ser Tyr Gln Ser Ala Ser Thr Glu
 1               5                  10

<210> SEQ ID NO 74
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 74

Ala Asn Lys Ile Ser Tyr Gln Ser Ser Lys Thr Glu
 1               5                  10

<210> SEQ ID NO 75
<211> LENGTH: 11
<212> TYPE: PRT
<213> ORGANISM: Artificial Sequence
<220> FEATURE:
<223> OTHER INFORMATION: completely synthetic amino acid sequence

<400> SEQUENCE: 75

Ala Asn Lys Ile Ser Tyr Gln Ser Ser Thr Glu
 1               5                  10

<210> SEQ ID NO 76
<211> LENGTH: 12
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (5)...(5)
<223> OTHER INFORMATION: Ser = d-serine

<400> SEQUENCE: 76

Ala Asn Lys Ile Ser Tyr Gln Ser Ser Ser Thr Glu
 1               5                  10

<210> SEQ ID NO 77
<211> LENGTH: 12
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (4)...(4)
<223> OTHER INFORMATION: Ile = D-isoleucine

<400> SEQUENCE: 77

Ala Asn Lys Ile Ser Tyr Gln Ser Ser Ser Thr Glu
```

<210> SEQ ID NO 78
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 78

Ala Asn Lys Ile Ser Tyr Gln Ser Ser Gln Thr Glu
 1               5                  10

<210> SEQ ID NO 79
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 79

Ala Asn Lys Ile Ser Tyr Gln Ser Ala Lys Thr Glu
 1               5                  10

<210> SEQ ID NO 80
<211> LENGTH: 12
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (3)...(3)
<223> OTHER INFORMATION: Lys = D-Lysine

<400> SEQUENCE: 80

Ala Asn Lys Ile Ser Tyr Gln Ser Ser Ser Thr Glu
 1               5                  10

<210> SEQ ID NO 81
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 81

Ala Asn Lys Ile Ser Tyr Gln Ser Thr Glu
 1               5                  10

<210> SEQ ID NO 82
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 82

Ala Asn Lys Ser Tyr Gln Ser Ser Thr Glu
 1               5                  10

<210> SEQ ID NO 83
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 83

```
Ala Asn Lys Ile Tyr Gln Ser Ser Thr Glu
 1               5                   10
```

<210> SEQ ID NO 84
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 84

```
Ala Asn Lys Ala Ser Tyr Gln Ser Ala Ser Thr Glu
 1               5                   10
```

<210> SEQ ID NO 85
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 85

```
Ala Asn Glu Ile Ser Tyr Gln Ser Ala Ser Thr Glu
 1               5                   10
```

<210> SEQ ID NO 86
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 86

```
Lys Ile Ser Tyr Gln Ser Ser
 1               5
```

<210> SEQ ID NO 87
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 87

```
Ser Tyr Gln Ser Ser Thr Glu
 1               5
```

<210> SEQ ID NO 88
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 88

```
Ser Tyr Gln Ser Ser Thr Leu
 1               5
```

<210> SEQ ID NO 89
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 89

Ala Ser Tyr Gln Ser Ser Thr Glu
1               5

<210> SEQ ID NO 90
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 90

Glu Ile Ser Tyr Gln Ser Ser Ser Thr Glu
1               5                   10

<210> SEQ ID NO 91
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 91

Ala Asn Glu Ile Ser Tyr Gln Ser Ser Ser Thr Glu
1               5                   10

<210> SEQ ID NO 92
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 92

Ala Asn Lys Ile Ser Tyr Tyr Ser Ser Ser Thr Glu
1               5                   10

<210> SEQ ID NO 93
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 93

Ala Asn Lys Ile Ser Tyr Tyr Ser Ala Ser Thr Glu
1               5                   10

<210> SEQ ID NO 94
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 94

Ala Ser Tyr Gln Ser Ser Leu
1               5

<210> SEQ ID NO 95
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 95

Ala Asn Ser Tyr Gln Ser Ser Ser Thr Glu

-continued

```
1               5                    10

<210> SEQ ID NO 96
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 96

Ala Ser Tyr Gln Ser Ser Ser Thr Glu
 1               5

<210> SEQ ID NO 97
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 97

Ser Tyr Gln Ser Ser Ser Thr Glu
 1               5

<210> SEQ ID NO 98
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 98

Ala Asn Lys Ala Ser Tyr Gln Ser Ala Ser Thr Cys
 1               5                   10

<210> SEQ ID NO 99
<211> LENGTH: 5
<212> TYPE: PRT
<213> ORGANISM: Artificial Sequence
<220> FEATURE:
<223> OTHER INFORMATION: completely synthetic amino acid sequence

<400> SEQUENCE: 99

Gln Ser Ser Thr Glu
 1               5

<210> SEQ ID NO 100
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 100

Tyr Gln Ser Ser Thr Glu
 1               5

<210> SEQ ID NO 101
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 101

Ser Gln Ser Ser Thr Glu
 1               5
```

```
<210> SEQ ID NO 102
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 102

Ala Asn Lys Ile Ser Gln Ser Ser Thr Glu
 1               5                  10

<210> SEQ ID NO 103
<211> LENGTH: 11
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (3)...(3)
<223> OTHER INFORMATION: Xaa = ornithine

<400> SEQUENCE: 103

Ala Asn Xaa Ile Ser Tyr Gln Ser Ser Thr Glu
 1               5                  10

<210> SEQ ID NO 104
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (2)...(2)
<223> OTHER INFORMATION: Xaa = 3,4-dichlorophenalanine

<400> SEQUENCE: 104

Ser Xaa Gln Ser Ser Thr Glu
 1               5

<210> SEQ ID NO 105
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (2)...(2)
<223> OTHER INFORMATION: Xaa = (3-pyridinyl)alanine

<400> SEQUENCE: 105

Ser Xaa Gln Ser Ser Thr Glu
 1               5

<210> SEQ ID NO 106
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 106

Ser Lys Gln Ser Ser Thr Glu
 1               5

<210> SEQ ID NO 107
<211> LENGTH: 7
<212> TYPE: PRT
```

```
<213> ORGANISM: Artificial Sequence
<220> FEATURE:
<223> OTHER INFORMATION: completely synthetic amino acid sequence

<400> SEQUENCE: 107

Ser Tyr Gln Ser Ser Ser Leu
 1               5

<210> SEQ ID NO 108
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = epsilon aminocaproic acid

<400> SEQUENCE: 108

Xaa Tyr Gln Ser Ser Ser Leu
 1               5

<210> SEQ ID NO 109
<211> LENGTH: 11
<212> TYPE: PRT
<213> ORGANISM: Artificial Sequence
<220> FEATURE:
<223> OTHER INFORMATION: completely synthetic amino acid sequence
<221> NAME/KEY: METHYLATION
<222> LOCATION: (4)...(4)
<223> OTHER INFORMATION: Xaa = N-methylisoleucine

<400> SEQUENCE: 109

Ala Asn Lys Xaa Ser Tyr Gln Ser Ser Thr Glu
 1               5                  10

<210> SEQ ID NO 110
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 110

Ser Tyr Gln Ser Ser Thr Glu
 1               5

<210> SEQ ID NO 111
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 111

Tyr Gln Ser Ser Thr Glu
 1               5

<210> SEQ ID NO 112
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 112

Ser Tyr Lys Ser Ser Thr Glu
 1               5
```

<210> SEQ ID NO 113
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 113

Ser Tyr Tyr Ser Ser Thr Glu
 1               5

<210> SEQ ID NO 114
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 114

Ser Tyr Gln Ser Ser Leu
 1               5

<210> SEQ ID NO 115
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 115

Ser Tyr Gln Ser Ser Leu
 1               5

<210> SEQ ID NO 116
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = 2,3-diaminopropionicacid

<400> SEQUENCE: 116

Xaa Tyr Gln Ser Ser Ser Leu
 1               5

<210> SEQ ID NO 117
<211> LENGTH: 11
<212> TYPE: PRT
<213> ORGANISM: Artificial Sequence
<220> FEATURE:
<223> OTHER INFORMATION: completely synthetic amino acid sequence

<400> SEQUENCE: 117

Ala Asn Lys Ile Ser Tyr Gln Ser Ser Ser Thr
 1               5                  10

<210> SEQ ID NO 118
<211> LENGTH: 12
<212> TYPE: PRT
<213> ORGANISM: Artificial Sequence
<220> FEATURE:
<223> OTHER INFORMATION: completely synthetic amino acid sequence

<400> SEQUENCE: 118

```
Ala Asn Lys Ala Ser Tyr Gln Ser Ala Ser Thr Leu
1               5                   10
```

<210> SEQ ID NO 119
<211> LENGTH: 11
<212> TYPE: PRT
<213> ORGANISM: Artificial Sequence
<220> FEATURE:
<223> OTHER INFORMATION: completely synthetic amino acid sequence

<400> SEQUENCE: 119

```
Ala Asn Lys Ala Ser Tyr Gln Ser Ala Ser Leu
1               5                   10
```

<210> SEQ ID NO 120
<211> LENGTH: 11
<212> TYPE: PRT
<213> ORGANISM: Artificial Sequence
<220> FEATURE:
<223> OTHER INFORMATION: completely synthetic amino acid sequence

<400> SEQUENCE: 120

```
Ala Asn Lys Ala Ser Tyr Gln Ser Ser Ser Leu
1               5                   10
```

<210> SEQ ID NO 121
<211> LENGTH: 10
<212> TYPE: PRT
<213> ORGANISM: Artificial Sequence
<220> FEATURE:
<223> OTHER INFORMATION: completely synthetic amino acid sequence

<400> SEQUENCE: 121

```
Ala Asn Lys Ala Ser Tyr Gln Ser Ser Leu
1               5                   10
```

<210> SEQ ID NO 122
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (7)...(7)
<223> OTHER INFORMATION: Leu = D-leucine

<400> SEQUENCE: 122

```
Ser Tyr Gln Ser Ser Thr Leu
1               5
```

<210> SEQ ID NO 123
<211> LENGTH: 11
<212> TYPE: PRT
<213> ORGANISM: Artificial Sequence
<220> FEATURE:
<223> OTHER INFORMATION: completely synthetic amino acid sequence

<400> SEQUENCE: 123

```
Ala Asn Lys Ala Ser Tyr Ala Ser Ser Ser Leu
1               5                   10
```

<210> SEQ ID NO 124
<211> LENGTH: 7
<212> TYPE: PRT
<213> ORGANISM: Artificial Sequence
<220> FEATURE:
<223> OTHER INFORMATION: completely synthetic amino acid sequence -continued

```
<400> SEQUENCE: 124

Lys Tyr Gln Ser Ser Ser Leu
 1               5

<210> SEQ ID NO 125
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 125

Ser Tyr Gln Ser Ser Lys Leu
 1               5

<210> SEQ ID NO 126
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (7)...(7)
<223> OTHER INFORMATION: Leu = D-leucine

<400> SEQUENCE: 126

Ser Tyr Gln Ser Ser Lys Leu
 1               5

<210> SEQ ID NO 127
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 127

Asn Lys Ile Ser Tyr Tyr Ser
 1               5

<210> SEQ ID NO 128
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 128

Asn Lys Ala Ser Tyr Gln Ser
 1               5

<210> SEQ ID NO 129
<211> LENGTH: 5
<212> TYPE: PRT
<213> ORGANISM: Artificial Sequence
<220> FEATURE:
<223> OTHER INFORMATION: completely synthetic amino acid sequence

<400> SEQUENCE: 129

Ser Tyr Gln Ser Ser
 1               5

<210> SEQ ID NO 130
<211> LENGTH: 8
<212> TYPE: PRT
<213> ORGANISM: Artificial Sequence
<220> FEATURE:
```

-continued

<223> OTHER INFORMATION: completely synthetic amino acid sequence

<400> SEQUENCE: 130

Asn Lys Ile Ser Tyr Gln Ser Ala
 1               5

<210> SEQ ID NO 131
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 131

Ala Asn Lys Ile Ser Tyr Tyr Ser
 1               5

<210> SEQ ID NO 132
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 132

Ala Asn Lys Ala Ser Tyr Gln Ser
 1               5

<210> SEQ ID NO 133
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 133

Ser Tyr Gln Ser Ser Thr
 1               5

<210> SEQ ID NO 134
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 134

Ser Tyr Gln Ser Ser Ser
 1               5

<210> SEQ ID NO 135
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 135

Ser Tyr Gln Ser Ser Leu
 1               5

<210> SEQ ID NO 136
<211> LENGTH: 9
<212> TYPE: PRT
<213> ORGANISM: Artificial Sequence
<220> FEATURE:
<223> OTHER INFORMATION: completely synthetic amino acid sequence

```
<400> SEQUENCE: 136

Ala Asn Lys Ile Ser Tyr Gln Ser Ala
 1               5

<210> SEQ ID NO 137
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 137

Ala Asn Lys Ile Ser Tyr Tyr Ser Ser
 1               5

<210> SEQ ID NO 138
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 138

Ala Asn Lys Ile Ser Tyr Tyr Ser Ala
 1               5

<210> SEQ ID NO 139
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 139

Ala Asn Lys Ala Ser Tyr Gln Ser Ala
 1               5

<210> SEQ ID NO 140
<211> LENGTH: 5
<212> TYPE: PRT
<213> ORGANISM: Artificial Sequence
<220> FEATURE:
<223> OTHER INFORMATION: completely synthetic amino acid sequence

<400> SEQUENCE: 140

Lys Tyr Gln Ser Ser
 1               5

<210> SEQ ID NO 141
<211> LENGTH: 5
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 141

Xaa Tyr Gln Ser Ser
 1               5

<210> SEQ ID NO 142
<211> LENGTH: 6
<212> TYPE: PRT
<213> ORGANISM: Artificial Sequence
```

```
<220> FEATURE:
<223> OTHER INFORMATION: completely synthetic amino acid sequence

<400> SEQUENCE: 142

Lys Tyr Gln Ser Ser Ser
 1               5

<210> SEQ ID NO 143
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 143

Xaa Tyr Gln Ser Ser Ser
 1               5

<210> SEQ ID NO 144
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 144

Ser Tyr Gln Ser Ser Ser Leu
 1               5

<210> SEQ ID NO 145
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 145

Xaa Tyr Gln Ser Ser Ser Leu
 1               5

<210> SEQ ID NO 146
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (7)...(7)
<223> OTHER INFORMATION: Leu = norleucine

<400> SEQUENCE: 146

Lys Tyr Gln Ser Ser Ser Leu
 1               5

<210> SEQ ID NO 147
<211> LENGTH: 5
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (2)...(2)
<223> OTHER INFORMATION: Xaa = cyclohexylalanine
```

```
<221> NAME/KEY: VARIANT
<222> LOCATION: (1)...(1)
<223> OTHER INFORMATION: Xaa = homoarginine
<221> NAME/KEY: VARIANT
<222> LOCATION: (5)...(5)
<223> OTHER INFORMATION: Leu = norleucine

<400> SEQUENCE: 147

Xaa Xaa Gln Ser Leu
 1               5

<210> SEQ ID NO 148
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = homotyrosine
<221> NAME/KEY: VARIANT
<222> LOCATION: (6)...(6)
<223> OTHER INFORMATION: Leu = norleucine

<400> SEQUENCE: 148

Xaa Xaa Gln Ser Ser Leu
 1               5

<210> SEQ ID NO 149
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = cyclohexylhomoalanine
<221> NAME/KEY: VARIANT
<222> LOCATION: (6)...(6)
<223> OTHER INFORMATION: Leu = norleucine

<400> SEQUENCE: 149

Xaa Xaa Gln Ser Ser Leu
 1               5

<210> SEQ ID NO 150
<211> LENGTH: 10
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (10)...(10)
<223> OTHER INFORMATION: Xaa = cyclohexylalanine

<400> SEQUENCE: 150

Ala Asn Lys Ala Ser Tyr Gln Ser Ser Xaa
 1               5                  10

<210> SEQ ID NO 151
<211> LENGTH: 6
<212> TYPE: PRT
<213> ORGANISM: Artificial Sequence
<220> FEATURE:
<223> OTHER INFORMATION: completely synthetic amino acid sequence
```

```
<221> NAME/KEY: VARIANT
<222> LOCATION: (1)...(1)
<223> OTHER INFORMATION: Xaa = homoarginine

<400> SEQUENCE: 151

Xaa Tyr Gln Ser Ser Pro
 1               5

<210> SEQ ID NO 152
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 152

Xaa Tyr Gln Ser Ser His
 1               5

<210> SEQ ID NO 153
<211> LENGTH: 5
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 153

Xaa Tyr Gln Ser Asn
 1               5

<210> SEQ ID NO 154
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (7)...(7)
<223> OTHER INFORMATION: Leu = norleucine

<400> SEQUENCE: 154

Xaa Tyr Gln Ser Ser Ser Leu
 1               5

<210> SEQ ID NO 155
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = 4-aminomethylphenylalanine
<221> NAME/KEY: VARIANT
<222> LOCATION: (7)...(7)
<223> OTHER INFORMATION: Leu = norleucine

<400> SEQUENCE: 155

Xaa Tyr Gln Ser Ser Ser Leu
 1               5
```

<210> SEQ ID NO 156
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 156

Xaa Tyr Gln Ser Ser Ser Leu
 1               5

<210> SEQ ID NO 157
<211> LENGTH: 10
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (10)...(10)
<223> OTHER INFORMATION: Xaa = cyclohexylalanine

<400> SEQUENCE: 157

Ala Asn Lys Ala Lys Tyr Gln Ser Ser Xaa
 1               5                  10

<210> SEQ ID NO 158
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = 2(4,6-dimethylpyrimidine)lysine
<221> NAME/KEY: VARIANT
<222> LOCATION: (7)...(7)
<223> OTHER INFORMATION: Leu = norleucine

<400> SEQUENCE: 158

Xaa Tyr Gln Ser Ser Ser Leu
 1               5

<210> SEQ ID NO 159
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = N'-(2-imidazolyl)lysine

<400> SEQUENCE: 159

Xaa Tyr Gln Ser Ser Leu
 1               5

<210> SEQ ID NO 160
<211> LENGTH: 10
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (5)...(5)
<223> OTHER INFORMATION: Xaa = homoarginine

<400> SEQUENCE: 160

Ala Asn Lys Ala Xaa Tyr Gln Ser Ser Leu
1               5                   10

<210> SEQ ID NO 161
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = (4-aminocyclohexl)alanine
<221> NAME/KEY: VARIANT
<222> LOCATION: (7)...(7)
<223> OTHER INFORMATION: Leu = norleucine

<400> SEQUENCE: 161

Xaa Tyr Gln Ser Ser Ser Leu
1               5

<210> SEQ ID NO 162
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = N' - (2-imidazolyl)lysine
<221> NAME/KEY: VARIANT
<222> LOCATION: (7)...(7)
<223> OTHER INFORMATION: Leu - norleucine

<400> SEQUENCE: 162

Xaa Tyr Gln Ser Ser Ser Leu
1               5

<210> SEQ ID NO 163
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = cyclohexylalanine
<221> NAME/KEY: VARIANT
<222> LOCATION: (7)...(7)
<223> OTHER INFORMATION: Leu - norleucine

<400> SEQUENCE: 163

Xaa Xaa Gln Ser Ser Ser Leu
1               5

<210> SEQ ID NO 164
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(7)
<223> OTHER INFORMATION: Xaa = homoarginine
<221> NAME/KEY: VARIANT
<222> LOCATION: (7)...(7)
<223> OTHER INFORMATION: Xaa = homoarginine

<400> SEQUENCE: 164

```
Xaa Tyr Gln Ser Ser Ser Xaa
 1               5
```

<210> SEQ ID NO 165
<211> LENGTH: 10
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (5)...(5)
<223> OTHER INFORMATION: Xaa = N'-(2-imidazolyl)lysine
<221> NAME/KEY: VARIANT
<222> LOCATION: (10)...(10)
<223> OTHER INFORMATION: Leu = norleucine

<400> SEQUENCE: 165

```
Ala Asn Lys Ala Xaa Tyr Gln Ser Ser Leu
 1               5                  10
```

<210> SEQ ID NO 166
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = 3-iodotyrosine
<221> NAME/KEY: VARIANT
<222> LOCATION: (7)...(7)
<223> OTHER INFORMATION: Leu = norleucine

<400> SEQUENCE: 166

```
Xaa Xaa Gln Ser Ser Ser Leu
 1               5
```

<210> SEQ ID NO 167
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = O-dimethylphosphotyrosine
<221> NAME/KEY: VARIANT
<222> LOCATION: (7)...(7)
<223> OTHER INFORMATION: Leu = norleucine

<400> SEQUENCE: 167

```
Xaa Xaa Gln Ser Ser Ser Leu
 1               5
```

<210> SEQ ID NO 168
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 168

Xaa Tyr Gln Ser Ser Asp
1               5

<210> SEQ ID NO 169
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = O-methyltyrosine
<221> NAME/KEY: VARIANT
<222> LOCATION: (7)...(7)
<223> OTHER INFORMATION: Leu - norleucine

<400> SEQUENCE: 169

Xaa Xaa Gln Ser Ser Ser Leu
1               5

<210> SEQ ID NO 170
<211> LENGTH: 10
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (10)...(10)
<223> OTHER INFORMATION: Leu = norleucine

<400> SEQUENCE: 170

Ala Asn Lys Ala Lys Tyr Gln Ser Ser Leu
1               5                   10

<210> SEQ ID NO 171
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = cyclohexylalanine

<400> SEQUENCE: 171

Xaa Xaa Gln Ser Ser Ser Leu
1               5

<210> SEQ ID NO 172
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = N' - (2-imidazolyl)lysine
<221> NAME/KEY: VARIANT
<222> LOCATION: (2)...(2)
<223> OTHER INFORMATION: Xaa = cyclohexylalanine
<221> NAME/KEY: VARIANT
<222> LOCATION: (7)...(7)
<223> OTHER INFORMATION: Leu = norleucine

<400> SEQUENCE: 172

Xaa Xaa Gln Ser Ser Ser Leu
1               5

<210> SEQ ID NO 173
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = cyclohexylalanine

<400> SEQUENCE: 173

Xaa Xaa Gln Ser Ser Ser
1               5

<210> SEQ ID NO 174
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = cyclohexylalanine
<221> NAME/KEY: VARIANT
<222> LOCATION: (6)...(6)
<223> OTHER INFORMATION: Leu = norleucine

<400> SEQUENCE: 174

Xaa Xaa Gln Ser Ser Leu
1               5

<210> SEQ ID NO 175
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = cyclohexylalanine
<221> NAME/KEY: VARIANT
<222> LOCATION: (6)...(6)
<223> OTHER INFORMATION: Leu = norleucine

<400> SEQUENCE: 175

Xaa Xaa Gln Ser Pro Leu
1               5

<210> SEQ ID NO 176
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)

```
<223> OTHER INFORMATION: Xaa = 3-fluorotyrosine
<221> NAME/KEY: VARIANT
<222> LOCATION: (7)...(7)
<223> OTHER INFORMATION: Leu = norleucine

<400> SEQUENCE: 176

Xaa Xaa Gln Ser Ser Ser Leu
 1               5

<210> SEQ ID NO 177
<211> LENGTH: 5
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 177

Xaa Tyr Gln Ser Pro
 1               5

<210> SEQ ID NO 178
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (6)...(6)
<223> OTHER INFORMATION: Leu = norleucine

<400> SEQUENCE: 178

Lys Tyr Gln Ser Lys Leu
 1               5

<210> SEQ ID NO 179
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = 4-aminophenylalanine
<221> NAME/KEY: VARIANT
<222> LOCATION: (7)...(7)
<223> OTHER INFORMATION: Leu = norleucine

<400> SEQUENCE: 179

Xaa Xaa Gln Ser Ser Ser Leu
 1               5

<210> SEQ ID NO 180
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (2)...(2)
<223> OTHER INFORMATION: Xaa = 7-HO-tetrahydroisoquinoline CO2H
<221> NAME/KEY: VARIANT
<222> LOCATION: (7)...(7)
```

<223> OTHER INFORMATION: Leu = norleucine

<400> SEQUENCE: 180

Xaa Xaa Gln Ser Ser Ser Leu
 1               5

<210> SEQ ID NO 181
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = ornithine
<221> NAME/KEY: VARIANT
<222> LOCATION: (7)...(7)
<223> OTHER INFORMATION: Leu = norleucine

<400> SEQUENCE: 181

Xaa Tyr Gln Ser Ser Ser Leu
 1               5

<210> SEQ ID NO 182
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 182

Lys Ala Ala Ser Ser Ser Leu
 1               5

<210> SEQ ID NO 183
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (7)...(7)
<223> OTHER INFORMATION: Leu = norleucine

<400> SEQUENCE: 183

Lys Tyr Gln Ser Ser Ser Leu
 1               5

<210> SEQ ID NO 184
<211> LENGTH: 11
<212> TYPE: PRT
<213> ORGANISM: Artificial Sequence
<220> FEATURE:
<223> OTHER INFORMATION: completely synthetic amino acid sequence

<400> SEQUENCE: 184

Leu Asn Lys Ala Ser Tyr Gln Ser Ser Ser Leu
 1               5                  10

<210> SEQ ID NO 185
<211> LENGTH: 5
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine
<221> NAME/KEY: VARIANT

```
<222> LOCATION: (2)...(2)
<223> OTHER INFORMATION: Xaa = cyclohexylalanine

<400> SEQUENCE: 185

Xaa Xaa Gln Ser Ser
 1               5

<210> SEQ ID NO 186
<211> LENGTH: 4
<212> TYPE: PRT
<213> ORGANISM: Artificial Sequence
<220> FEATURE:
<223> OTHER INFORMATION: completely synthetic amino acid sequence

<400> SEQUENCE: 186

Tyr Gln Ser Ser
 1

<210> SEQ ID NO 187
<211> LENGTH: 4
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 187

Xaa Tyr Gln Ser
 1

<210> SEQ ID NO 188
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = homoarginine

<400> SEQUENCE: 188

Xaa Tyr Gln Ser Ser Ser
 1               5

<210> SEQ ID NO 189
<211> LENGTH: 5
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (5)...(5)
<223> OTHER INFORMATION: Leu = norleucine

<400> SEQUENCE: 189

Gln Ser Ser Ser Leu
 1               5

<210> SEQ ID NO 190
<211> LENGTH: 6
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = 7-HO-tetrahydro-3-isoquinoline CO2H
```

```
<221> NAME/KEY: VARIANT
<222> LOCATION: (6)...(6)
<223> OTHER INFORMATION: Leu = norleucine

<400> SEQUENCE: 190

Xaa Gln Ser Ser Ser Leu
 1               5

<210> SEQ ID NO 191
<211> LENGTH: 11
<212> TYPE: PRT
<213> ORGANISM: Artificial Sequence
<220> FEATURE:
<223> OTHER INFORMATION: completely synthetic amino acid sequence

<400> SEQUENCE: 191

Ala Asn Lys Ala Ser Tyr Ala Ser Ser Ser Leu
 1               5                  10

<210> SEQ ID NO 192
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 192

Ser Tyr Gln Ser Ser Lys Leu
 1               5

<210> SEQ ID NO 193
<211> LENGTH: 9
<212> TYPE: PRT
<213> ORGANISM: Artificial Sequence
<220> FEATURE:
<223> OTHER INFORMATION: completely synthetic amino acid sequence

<400> SEQUENCE: 193

Ala Asn Lys Ala Ser Tyr Gln Ser Leu
 1               5

<210> SEQ ID NO 194
<211> LENGTH: 7
<212> TYPE: PRT
<213> ORGANISM: Artificial Sequence
<220> FEATURE:
<223> OTHER INFORMATION: completely synthetic amino acid sequence
<221> NAME/KEY: VARIANT
<222> LOCATION: (1)...(1)
<223> OTHER INFORMATION: Xaa = ornithine

<400> SEQUENCE: 194

Xaa Tyr Gln Ser Ser Ser Leu
 1               5
```